United States Patent [19]

Theodore et al.

[11] Patent Number: 6,015,897
[45] Date of Patent: Jan. 18, 2000

[54] BIOTINAMIDO-N-METHYLGLYCYL-SERYL-O-SUCCINAMIDO-BENZYL DOTA

[75] Inventors: Louis J. Theodore, Lynnwood; Sudhakar Kasina, Kirkland; John M. Reno, Brier; Linda M. Gustavson, Seattle, all of Wash.

[73] Assignee: NeoRx Corporation, Seattle, Wash.

[21] Appl. No.: 08/645,211

[22] Filed: May 13, 1996

Related U.S. Application Data

[60] Division of application No. 08/351,005, Dec. 7, 1994, abandoned, which is a continuation-in-part of application No. 08/163,188, Dec. 7, 1993, abandoned, which is a continuation-in-part of application No. PCT/US93/05406, Jun. 7, 1993, which is a continuation-in-part of application No. 07/995,381, Dec. 23, 1992, abandoned, which is a continuation-in-part of application No. 07/895,588, Jun. 9, 1992, Pat. No. 5,283,342.

[51] Int. Cl.$^7$ .................................................. C07D 257/02
[52] U.S. Cl. ............................................................ 540/474
[58] Field of Search ........................... 435/7.5; 424/1.11, 424/1.53, 1.69, 9.1, 152.1, 155.1, 178.1; 530/391.5, 391.1, 391.3; P10J 540/474

[56] References Cited

U.S. PATENT DOCUMENTS

| | | |
|---|---|---|
| 4,179,337 | 12/1979 | Davis et al. . |
| 4,732,863 | 3/1988 | Tomasi et al. . |
| 4,863,713 | 9/1989 | Goodwin et al. .......................... 424/1.1 |
| 4,867,962 | 9/1989 | Abrams . |
| 4,902,502 | 2/1990 | Nitecki et al. . |
| 5,089,261 | 2/1992 | Nitecki et al. . |
| 5,171,563 | 12/1992 | Abrams et al. . |
| 5,183,660 | 2/1993 | Ikeda et al. . |
| 5,281,698 | 1/1994 | Nitecki . |
| 5,342,940 | 8/1994 | Ono et al. . |
| 5,556,982 | 9/1996 | Fritzber et al. . |

FOREIGN PATENT DOCUMENTS

| | | |
|---|---|---|
| 0251494 | 1/1988 | European Pat. Off. . |
| 0496074 | 7/1992 | European Pat. Off. . |
| WO 89/10140 | 11/1989 | WIPO . |
| WO 92/12730 | 8/1992 | WIPO . |
| WO 93/15210 | 8/1993 | WIPO . |
| WO 93/25240 | 12/1993 | WIPO . |
| WO 94/04702 | 3/1994 | WIPO . |
| WO 94/26297 | 11/1994 | WIPO . |

OTHER PUBLICATIONS

J. Haensler et al, "Synthesis and Characterization of a Trigalactosylated Bisacridine Compound to Target DNA to Hepatocytes", *Bioconjugate Chem.* vol. 4, No. 1, pp. 85–93 (1993).

Mauk et al, "Targeting of Lipid vesicles: Specificity of carbohydrate receptor analogues for leukocytes in mice", *Proc. Natl. Acad. Sci. USA*, vol. 77, pp. 4430–4434 (1980).

Ponpipom et al, "Cell–Specific Ligands for Selective Drug Delivery to Tissues and Organs", *J. Med. Chem.*, vol. 24, No. 12, pp. 1388–1395 (1981).

Schnaar et al, "Adhesion of Chicken Hepatocytes to Polyacrylamide Gels Derivatized with N–Acetylglucosamine", *Journal of Biological Chemistry*, vol. 253, No. 21, Nov. 10, 1978, pp. 7940–7951.

Ponpipom et al, "Cell surface carbohydrates for targeting studies", *Can. J. Chem.*, 58, 214 (1980).

Weigel, "GlycoConjugates Composition, Structure and Function", "Chapter 14, Mechanisms and Control of Glycoconjugates Turnover", edited by Allen et al, Marcel Dekker, Inc., NY, pp. 421–497 (1992).

Weigel, "Endocytic Components: Identification and Characterization", *Subcellular Biochemistry*, vol. 19, Chapter 5, Endocytosis and Function of the Hepatic Asialoglycoprotein Receptor, edited by Bergeron et al, New York, pp. 125–161 (1993).

Hubbard et al, "Suppression of the Anti–DNP IgE Response with Tolerogenic Conjugates of DNP with Polyvinyl Alcohol", *J. of Immunology*, vol. 126, No. 2, Feb. 1981 pp. 407–413.

Chen et al, "Properties of Two Urate Oxidases Modified by the Covalent Attachment of Poly(ethylene Glycol)", *Biochimica et Biophysica Acta.*, 660 pp. 293–298 (1981).

Savoca et al, "Preparation of a Non–Immunogenic Arginase by the Covalent Attachment of Polyethylene Glycol", *Biochimica et Biophysica Acta*, 578, pp. 47–53 (1979).

Lee et al, "Abrogation of the Antibenzylpenicilloyl (BPO) IgE Response with BPO–Polyvinyl Alcohol Conjugates", *Int. Archs Allergy appl. Immun.*, vol. 63, pp. 1–13 (1980).

Lee et al, "Suppression of Reaginic Antibodies with Modified Allergens", *Int. Archs Allergy appl. Immun.*, vol. 56, pp. 159–170 (1978).

Davis et al, "Alteration of the circulating life and antigenic properties of bovine adenosine deaminase in mice by attachment of polyethylene glycol", *Clin. exp. Immunol.*, vol. 46, pp. 649–652 (1981).

Ling et al, "A General Study of the Binding and Separation in Partition Affinity Ligand Assay. Immunoassay of $\beta_2$–Microglobulin", *J. Immunological Methods*, vol. 59, pp. 327–337 (1983).

Abuchowski et al, "Alteration of Immunological Properties of Bovine Serum Albumin by Covalent Attachment of Polyethylene Glycol", *J. of Biological Chem.*, vol. 252, No. 11, pp. 3578–3581 (1977).

Abuchowski et al, "Cancer Therapy with Chemically Modified Enzymes. I. Antitumor Properties of Polyethylene Glycol–Asparaginase Conjugates", *Can. Biochem Biophys.*, vol. 7, pp. 175–186 (1984).

(List continued on next page.)

*Primary Examiner*—Christina Y. Chan
*Assistant Examiner*—Phillip Gambel
*Attorney, Agent, or Firm*—Seed and Berry LLP

[57] ABSTRACT

Methods, compounds, compositions and kits that relate to pretargeted delivery of diagnostic and therapeutic agents are disclosed. Biotinamido-N-methylglycyl-seryl-O-succinamido-benzyl DOTA is disclosed.

1 Claim, 7 Drawing Sheets

OTHER PUBLICATIONS

Beauchamp et al, "A New Procedure for the Synthesis of Polyethylene Glycol–Protein Adducts; Effects on Function, Receptor Recognition, and Clearance of Superoxide Dismutase, Lactoferrin, and $\alpha_2$–Macroglobulin", *Analytical Biochem.*, vol. 131, pp. 25–33 (1983).

Leonard et al, "Synthesis of monomethoxypolyoxyethylene–Bound haemoglobins", *Tetrahedron*, vol. 40, No. 9, pp. 1581–1584 (1984).

Mauk et al, "Vesicle Targeting: Timed Release and Specificity for Leukocytes in Mice by Subcutaneous Injection", *Science*, vol. 207, No. 18, Jan. 1980 pp. 309–311.

J. Mattes, *J. Natl. Canc. Instit.*, "Biodistribution of Antibodies After Intraperitoneal or Intravenous Injection and Effect of Carbohydrate Modifications", vol. 79, No. 4, Oct. 1, 1987, pp. 855–863.

Peter van der Sluijs et al, *Hepatology*, "Drug Targeting to the Liver and Lactosylated Albumins: Does the Glycoprotein Target the Drug or is the Drug Targeting the Glycoprotein?", vol. 6, No. 4, (1986), pp. 723–728.

G. Paganelli, *Nucl. Med. Comm.*, "Monoclonal Antibody Pretargetting Techniques for Tumor Localization: The Avidin–Biotin System", vol. 12, (1991), pp. 211–234.

F. Virzi et al, *Nucl. Med. Biol.*, "New Indium–111 Labeled Biotin Derivatives for Improved Immunotargeting", vol. 18, No. 7, pp. 719–726 (1991).

R. T. Lee et al, *Glycoconjugate*, "Preparation of Cluster Glycosides of N–Acetylgalactosamine That Have Subnanomolar Binding Constants Towards the Mammalian Hepatic Gal/GalNAc–specific Receptor", vol. 4, (1987), pp. 317–328.

R. T. Lee et al, *Biochemistry*, "New Synthetic Cluster Ligands for Galactose/N–Acetylgalactosamine–Specific Lectin of Mammalian Liver", vol. 23, (1984), pp. 4255–4261.

J. R. Merwin et al, *Bioconjugate Chem.*, "Targeted Delivery of DNA Using YEE(GalNAcAH)$_3$, a Synthetic Glycopeptide Ligand for the Asialoglycoprotein Receptor", vol. 5 (1994), pp. 612–620.

M. A. Findeis, *Int. J. Peptide Protein Res.*, "Stepwise synthesis of a GalNAc–containing cluster glycoside ligand of the asialoglycoprotein receptor", vol. 43, (1994), pp. 477–485.

T. D. McKee et al, *Bioconjugate Chem.*, "Preparation of Asialoorosomucoid–Polylysine Conjugates", vol. 5, (1994), pp. 306–311.

E. A. L. Biessen et al, *J. Med. Chem.*, "Synthesis of Cluster Galactosides with High Affinity for the Hepatic Asialoglycoprotein Receptor", vol. 38, No. 9, (1995), pp. 1538–1546.

Marshall et al, *British Journal of Cancer*, "Galactosylated streptavidin for improved clearance of biotinylated intact and F(ab')$_2$ fragments of an anti–tumour antibody", 71:18–24 (1995).

Marshall et al, *British Journal of Cancer*, "Clearance of circulating radio–antibodies using streptavidin or secone antibodies in a xenograft model", 69:502–507 (1994).

Marshall et al, *British Journal of Cancer*, "Polyethylene glycol modification of a galactosylated streptavidin clearing agent: effects on immunogenicity and clearance of a biotinylated anti–tumour antibody", 73:565–572 (1996).

Samuel Zalipsky, "Functionalized Poly(ethylene glycol) for Preparation of Biologically Relevant Conjugates", Reviews, American Chemical Society, *Bioconjugate Chem.*, 1995, vol. 6, pp. 150–165.

I.S. Krull et al, *J. of Chromatography B: Biomedical Applications*, "Solid–phase derivatization reactions for biomedical liquid chromatography" pp. 19–50 (1994).

Merriam–Webster's Collegiate Dictionary, Tenth Edition, Merriam–Webster, Inc., Springfield, MA, p. 95, 1996.

Paganelli, G. et al. Nuclear Medicine Comm. 12: 211–234, 1991.

Richey, H. G. Fundamentals of Organic Chemistry, Prentice–Hall, Inc., Engelwood NJ, p. 324, 1983.

Axworthy et al., "Antibody Pretargeting For Radioimmunotherapy: A Three–Step Approach In Tumored Nude Mice," *The Journal Of Nuclear Medicine;* Proceedings Of The 39$^{th}$ Annual Meeting 33: p. 880, Abstract No. 234, 1992.

Galli et al., "A Radiopharmaceutical For The Study Of The Liver: $^{99m}$Tc–DTPA–ASIALO–OROSOMUCOID. II: Human Dynamic and Imaging Studies," *The Journal Of Nuclear Medicine And Allied Sciences 32:* 117–126, 1988.

Goodwin, "New Methods for Localizing Infection: A Role for Avidin–Biotin," *The Journal of Nuclear Medicine 33*(10): 1816–1818, 1992.

Sanderson et al., "Preparation And Characterization Of Biotin Conjugates Of Anti–Pan–Carcinoma NR–LU–10 Monoclonal Antibody For A Three Step Radioimmunotherapy," *The Journal Of Nuclear Medicine;* Proceedings Of The 39$^{th}$ Annual Meeting 33: p. 880, Abstract No. 233, 1992.

| | +PBS | SD | +NON-BT | SD | %ID +10:1 | SD | +5:1 | SD | BT-SAT'D | SD |
|---|---|---|---|---|---|---|---|---|---|---|
| BLOOD | 31.05 | 5.08 | 29.94 | 1.35 | 8.54 | 0.91 | 7.03 | 0.18 | 24.58 | 0.68 |
| TAIL | 2.34 | 0.70 | 1.80 | 0.09 | 1.46 | 0.09 | 1.76 | 0.04 | 1.96 | 0.40 |
| LUNG | 1.47 | 0.26 | 1.09 | 0.22 | 0.54 | 0.10 | 0.48 | 0.07 | 0.76 | 0.01 |
| LIVER | 5.42 | 0.69 | 4.66 | 0.36 | 9.60 | 1.20 | 9.11 | 0.41 | 6.76 | 0.06 |
| SPLEEN | 0.25 | 0.05 | 0.34 | 0.03 | 0.17 | 0.03 | 0.18 | 0.00 | 0.38 | 0.02 |
| STOMACH | 0.28 | 0.02 | 0.33 | 0.03 | 0.53 | 0.34 | 0.49 | 0.00 | 0.29 | 0.04 |
| KIDNEY | 1.72 | 0.24 | 1.38 | 0.08 | 2.76 | 0.00 | 3.28 | 0.32 | 1.58 | 0.08 |
| INTESTINE | 3.40 | 0.73 | 3.44 | 0.10 | 4.22 | 0.02 | 6.62 | 0.14 | 2.83 | 0.13 |
| | 46.02 | | 42.98 | | 27.83 | | 28.95 | | 39.13 | |
| | Group 1 | | Group 2 | | Group 3 | | Group 4 | | Group 5 | |

Fig. 8

BIOTINAMIDO-N-METHYLGLYCYL-SERYL-O-SUCCINAMIDO-BENZYL DOTA

CROSS-REFERENCE TO RELATED APPLICATIONS

This application is a divisional of application Ser. No. 08/351,005, filed Dec. 7, 1994 now abandoned, which is a continuation-in-part of U.S. Ser. No. 08/163,188 filed on Dec. 7, 1995, now abandoned which is a continuation-in-part of pending PCT Patent Application No. PCT/US93/05406, filed Jun. 7, 1993 and designating the United States, which, in turn, is a continuation-in-part of pending U.S. patent application Ser. No. 07/995,381, filed Dec. 23, 1992, now abandoned which is, in turn, a continuation-in-part of pending U.S. patent application Ser. No. 07/895,588, filed Jun. 9, 1992, now U.S. Pat. No. 5,283,342. These applications are incorporated by reference herein.

TECHNICAL FIELD

The present invention relates to methods, compounds, compositions and kits useful for delivering to a target site a targeting moiety that is conjugated to one member of a ligand/anti-ligand pair. After localization and clearance of the targeting moiety conjugate, direct or indirect binding of a diagnostic or therapeutic agent conjugate at the target site occurs.

BACKGROUND OF THE INVENTION

Conventional cancer therapy is plagued by two problems. The generally attainable targeting ratio (ratio of administered dose localizing to tumor versus administered dose circulating in blood or ratio of administered dose localizing to tumor versus administered dose migrating to bone marrow) is low. Also, the absolute dose of radiation or therapeutic agent delivered to the tumor is insufficient in many cases to elicit a significant tumor response. Improvement in targeting ratio or absolute dose to tumor is sought.

SUMMARY OF THE INVENTION

The present invention is directed to diagnostic and therapeutic pretargeting methods, moieties useful therein and methods of making those moieties. Such pretargeting methods are characterized by an improved targeting ratio or increased absolute dose to the target cell sites in comparison to conventional cancer therapy.

The present invention provides for effective delivery of cytotoxic active agents such as toxins, bacterial toxins and fungal metabolites, including highly toxic moieties such as palytoxins. The decoupling of the pharmacokinetics of the targeting moiety (generally slow) and the active agent (generally rapid for low molecular weight active agents and generally somewhat slower for higher molecular weight active agents when administered alone) and the high affinity binding of ligand-anti-ligand pairs provide for this improvement. When the active agents or active agent-ligand or active agent-anti-ligand conjugates to be administered are not themselves generally rapidly cleared (preferably via the renal pathway), conjugates containing such active agents are constructed to impart relatively rapid, and preferably renal, clearance thereto or lower, therapeutically effective, doses of active agent are administered. Thus, the protocol recipient's non-target tissue does not suffer prolonged exposure to the active agent.

The present invention provides two-step and three-step pretargeting methods, employing the steps set forth below:

administering to the recipient a first conjugate including an antibody targeting moiety of a first antibody species having a first pattern of cross-reactivity and a member of a ligand-anti-ligand binding pair; and administering to the recipient one or more additional targeting conjugates, each such conjugate including an antibody targeting moiety of a different species from the species of the first conjugate and each other having a substantially non-overlapping pattern of cross reactivity from that of other additional targeting conjugates and from each other and from the first pattern of cross-reactivity and the member of the ligand-anti-ligand pair bound to the first conjugate.

In the practice of these aspects of the present invention, target site accretion of active agent conjugate receptor (i.e., the ligand or anti-ligand conjugated to the first antibody species and additional targeting antibody species) is improved, because each antibody species recognizes a different epitope associated with the target site. This alternative epitope approach provides a target site that is more densely populated with the anti-ligand or ligand antigen to which the subsequently administered active agent-containing conjugate may bind via high affinity ligand-anti-ligand interactions. This increased target site antigen density facilitates increased active agent accretion thereto.

The present invention also provides pretargeting photodynamic therapy protocols as set forth below.

The two-step approach involves:

administering to the recipient a first conjugate comprising a targeting moiety and a member of a ligand-anti-ligand binding pair, wherein the first conjugate localizes to a target site;

optionally administering to the recipient a clearing agent capable of directing the clearance of circulating conjugate from the recipient or optionally treating the recipient with a clearing device or an alternative clearing procedure to substantially remove circulating conjugate from the recipient; and administering to the recipient a second conjugate comprising a photosensitizing agent and a ligand/anti-ligand binding pair member, wherein the second conjugate binding pair member is complementary to that of the first conjugate and wherein the photosensitizing agent or the second conjugate is chemically modified to induce rapid and, preferably, renal clearance thereof from the recipient.

One alternative to the optional clearance step set forth above is simply to allow an amount of time to pass that is sufficient to permit the recipient's native clearance mechanisms to substantially remove circulating first conjugate.

The three-step approach involves:

administering to the recipient a first conjugate comprising a targeting moiety and a ligand, wherein the targeting moiety-ligand conjugate localizes to a target site;

administering to the recipient an anti-ligand; and administering to the recipient a second conjugate comprising the ligand and a photosensitive agent, wherein the photosensitizing agent or the second conjugate is chemically modified to induce rapid and, preferably, renal clearance thereof from the recipient and wherein second conjugate localization at the target site is enhanced as a result of prior localization of the first conjugate.

While the two-step and three-step pretargeting methods of the present invention may be conducted despite the presence of recipient endogenous biotin, the present invention also provides methods of decreasing the endogenous biotin level or the impact thereof. One method is to overwhelm the endogenous biotin with a high dose of targeting moiety-streptavidin or -avidin conjugate. Another method is a pretreatment with an amount of avidin sufficient to bind substantially all of a recipient's endogenous biotin. In conducting this method, avidin may be administered intravenously, orally or by enema. Alternatively, the recipient may be placed on a biotin-free diet prior to conducting a two-step or three-step pretargeting protocol. Another method to address endogenous biotin employs oral, non-absorbable antibiotics.

Cytokines, such as interleukins (e.g., IL-2 and IL-4), colony stimulating factors (e.g., GM-CSF), interferons, (e.g., interferon-gamma), and tumor necrosis factor (TNF), may be employed as anti-tumor active agents in the practice of two-step or three-step pretargeting protocols of the present invention. In addition, the pretargeting protocols of the present invention have applications with respect to additional conditions. Immunosuppressive cytokines, such as TGF-beta, may be employed, for example, in the treatment of autoimmune diseases; such as rheumatoid arthritis, systemic lupus erythematosus, insulin-dependent diabetes mellitus, multiple sclerosis, pulmonary fibrosis and the like; tissue transplantation facilitation in liver and kidney tissues, for example; obviation or prevention of graft-versus-host reaction; and the like.

BRIEF DESCRIPTION OF THE DRAWINGS

FIG. 8 shows limited biodistribution data for LU-10-StrAv conjugate upon administration of three controls (Groups 1, 2 and 5) and two doses of clearing agent (Groups 3 and 4) at two hours post-clearing agent administration.

DETAILED DESCRIPTION OF THE INVENTION

Figure 1:
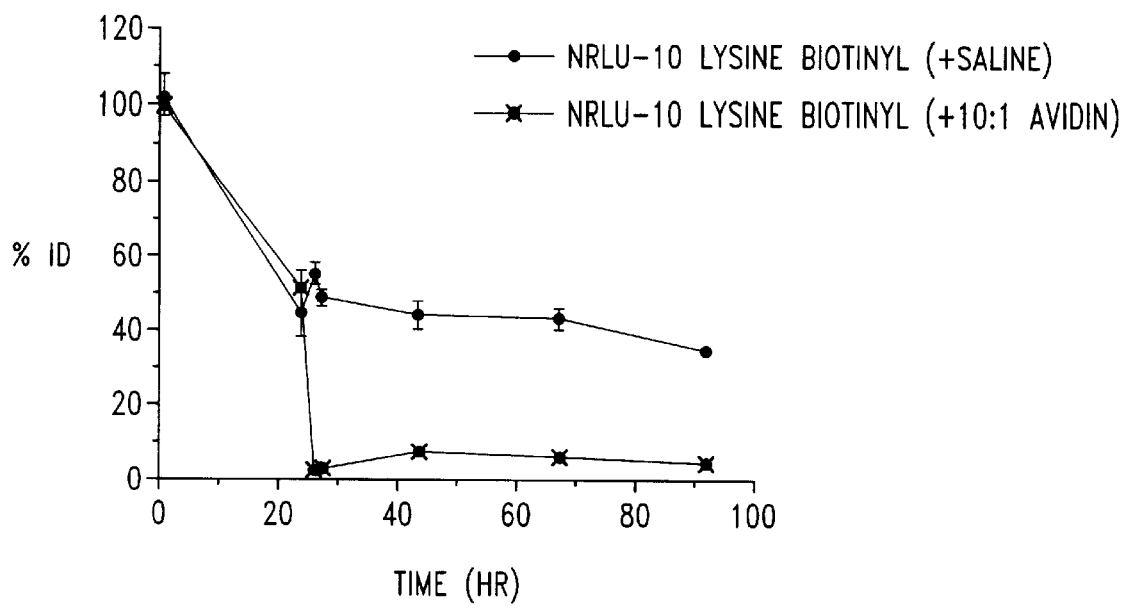
FIG. 1 illustrates blood clearance of biotinylated antibody following intravenous administration of avidin.

Prior to setting forth the invention, it may be helpful to set forth definitions of certain terms to be used within the disclosure.

Targeting moiety: A molecule that binds to a defined population of cells. The targeting moiety may bind a receptor, an oligonucleotide, an enzymatic substrate, an antigenic determinant, or other binding site present on or in the target cell population. Antibody is used throughout the specification as a prototypical example of a targeting moiety. Antibody fragments and small peptide sequences capable of recognizing expressed antigen are also contemplated targeting moieties within the present invention. Tumor is used as a prototypical example of a target in describing the present invention.

Ligand/anti-ligand pair: A complementary/anti-complementary set of molecules that demonstrate specific binding, generally of relatively high affinity. Exemplary ligand/anti-ligand pairs include zinc finger protein/dsDNA fragment, enzyme/inhibitor, hapten/antibody, lectin/carbohydrate, ligand/receptor, and biotin/avidin. Lower molecular weight forms of the ligand or anti-ligand molecules that bind with complementary anti-ligands or ligands are also contemplated by the present invention. Biotin/avidin is used throughout the specification as a prototypical example of a ligand/anti-ligand pair.

Anti-ligand: As defined herein, an "anti-ligand" demonstrates high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Anti-ligands of the present invention may exhibit or be derivatized to exhibit structural features that direct the uptake thereof, e.g., galactose residues that direct liver uptake. Avidin and streptavidin are used herein as prototypical anti-ligands.

Avidin: As defined herein, "avidin" includes avidin, streptavidin and derivatives and analogs thereof that are capable of high affinity, multivalent or univalent binding of biotin.

Ligand: As defined herein, a "ligand" is a relatively small, soluble molecule that exhibits rapid serum, blood and/or whole body clearance when administered intravenously in an animal or human. Biotin is used as the prototypical ligand.

Active Agent: A diagnostic or therapeutic agent ("the payload"), including radionuclides, drugs, anti-tumor agents, toxins and the like. Radionuclide therapeutic agents are used as prototypical active agents.

$N_xS_y$ Chelates: As defined herein, the term "$N_xS_y$ chelates" includes buoy chelators that are capable of (i) coordinately binding a metal or radiometal and (ii) covalently attaching to a targeting moiety, ligand or anti-ligand. Particularly preferred $N_xS_y$ chelates have $N_2S_2$ and $N_3S$ cores. Exemplary $N_xS_y$ chelates are described in Fritzberg et al., Proc. Natl. Acad. Sci. USA 85: 4024–29, 1988; in Weber et al., Bioconi. Chem. 1: 431–37, 1990; and in the references cited therein, for instance.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step and other related methods described herein are also encompassed.

Clearing Agent: An agent capable of binding, complexing or otherwise associating with an administered moiety (e.g., targeting moiety-ligand, targeting moiety-anti-ligand or anti-ligand alone) present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that limit clearing agent access to the population of target cells recognized by a targeting moiety used in the same treatment protocol as the clearing agent.

Target Cell Retention: The amount of time that a radionuclide or other therapeutic agent remains at the target cell surface or within the target cell. Catabolism of conjugates or molecules containing such therapeutic agents appears to be primarily responsible for the loss of target cell retention.

Conjugate: A conjugate encompasses chemical conjugates (covalently or non-covalently bound), fusion proteins and the like.

A recognized disadvantage associated with in vivo administration of targeting moiety-radioisotopic conjugates for imaging or therapy is localization of the attached radioactive agent at both non-target and target sites. Until the administered radiolabeled conjugate clears from the circulation, normal organs and tissues are transitorily exposed to the attached radioactive agent. For instance, radiolabeled whole antibodies that are administered in vivo exhibit relatively slow blood clearance; maximum target site localization generally occurs 1–3 days post-administration. Generally, the longer the clearance time of the conjugate from the circulation, the greater the radioexposure of non-target organs.

These characteristics are particularly problematic with human radioimmunotherapy. In human clinical trials, the long circulating half-life of radioisotope bound to whole antibody causes relatively large doses of radiation to be delivered to the whole body. In particular, the bone marrow, which is very radiosensitive, is the dose-limiting organ of non-specific toxicity.

In order to decrease radioisotope exposure of non-target tissue, potential targeting moieties generally have been screened to identify those that display minimal non-target reactivity, while retaining target specificity and reactivity. By reducing non-target exposure (and adverse non-target localization and/or toxicity), increased doses of a radiotherapeutic conjugate may be administered; moreover, decreased non-target accumulation of a radiodiagnostic conjugate leads to improved contrast between background and target.

Therapeutic drugs, administered alone or as targeted conjugates, are accompanied by similar disadvantages. Again, the goal is administration of the highest possible concentration of drug (to maximize exposure of target tissue), while remaining below the threshold of unacceptable normal organ toxicity (due to non-target tissue exposure). Unlike radioisotopes, however, therapeutic drugs need to be taken into a target cell to exert a cytotoxic effect. In the case of targeting moiety-therapeutic drug conjugates, it would be advantageous to combine the relative target specificity of a targeting moiety with a means for enhanced target cell internalization of the targeting moiety-drug conjugate.

In contrast, enhanced target cell internalization is disadvantageous if one administers diagnostic agent-targeting moiety conjugates. Internalization of diagnostic conjugates results in cellular catabolism and degradation of the conjugate. Upon degradation, small adducts of the diagnostic agent or the diagnostic agent per se may be released from the cell, thus eliminating the ability to detect the conjugate in a target-specific manner.

One method for reducing non-target tissue exposure to a diagnostic or therapeutic agent involves "pretargeting" the targeting moiety at a target site, and then subsequently administering a rapidly clearing diagnostic or therapeutic agent conjugate that is capable of binding to the "pretargeted" targeting moiety at the target site. A description of some embodiments of the pretargeting technique may be found in U.S. Pat. No. 4,863,713 (Goodwin et al.).

A typical pretargeting approach ("three-step") is schematically depicted below.

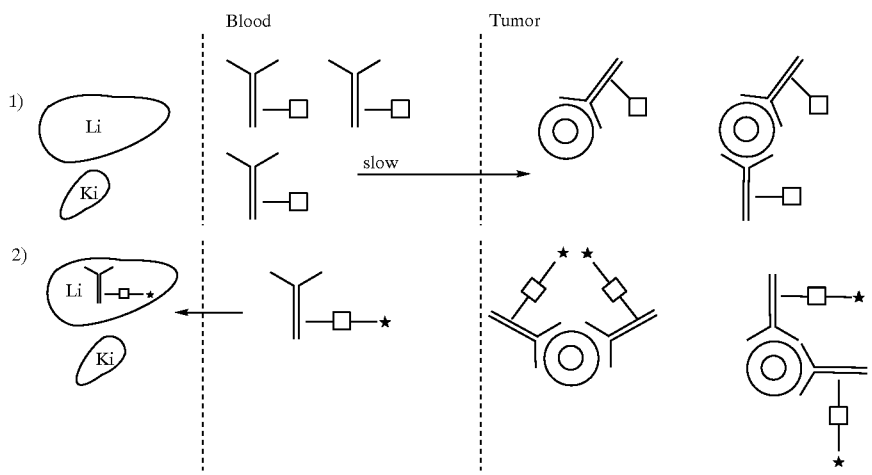

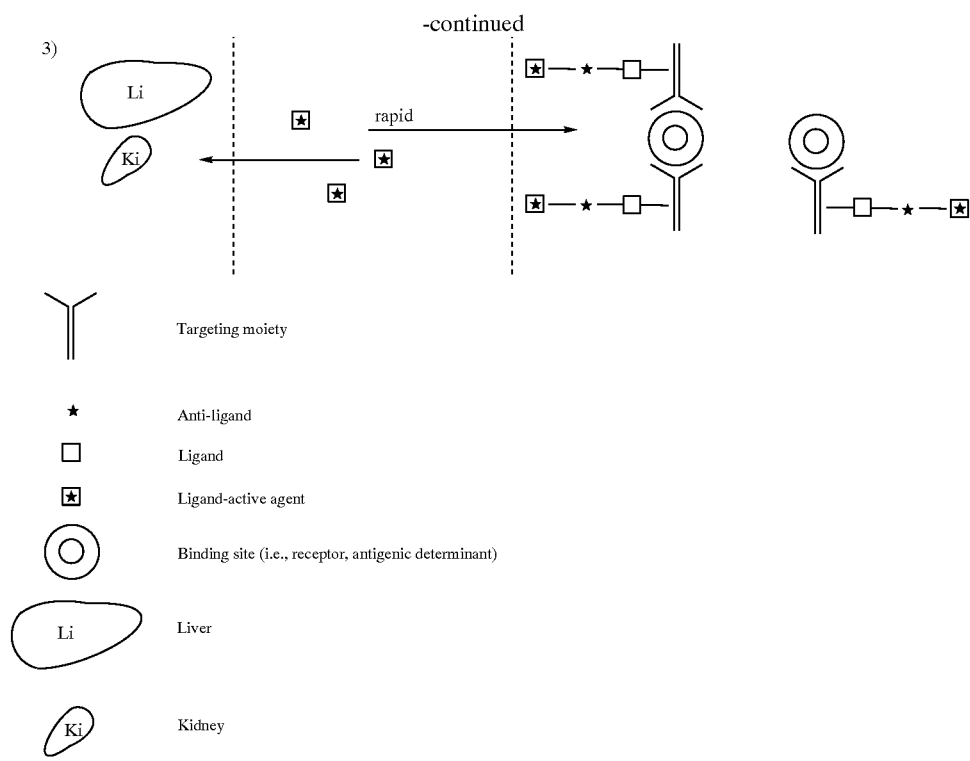

Briefly, this three-step pretargeting protocol features administration of an antibody-ligand conjugate, which is allowed to localize at a target site and to dilute in the circulation. Subsequently administered anti-ligand binds to the antibody-ligand conjugate and clears unbound antibody-ligand conjugate from the blood. Preferred anti-ligands are large and contain sufficient multivalency to accomplish crosslinking and aggregation of circulating antibody-ligand conjugates. The clearing by anti-ligand is probably attributable to anti-ligand crosslinking and/or aggregation of antibody-ligand conjugates that are circulating in the blood, which leads to complex/aggregate clearance by the recipient's RES (reticuloendothelial system). Anti-ligand clearance of this type is preferably accomplished with a multi-valent molecule; however, a univalent molecule of sufficient size to be cleared by the RES on its own could also be employed. Alternatively, receptor-based clearance mechanisms, e.g., Ashwell receptor or hexose residue, such as galactose or mannose residue, recognition mechanisms, may be responsible for anti-ligand clearance. Such clearance mechanisms are less dependent upon the valency of the anti-ligand with respect to the ligand than the RES complex/aggregate clearance mechanisms. It is preferred that the ligand-anti-ligand pair displays relatively high affinity binding.

A diagnostic or therapeutic agent-ligand conjugate that exhibits rapid whole body clearance is then administered. When the circulation brings the active agent-ligand conjugate in proximity to the target cell-bound antibody-ligand-anti-ligand complex, anti-ligand binds the circulating active agent-ligand conjugate and produces an antibody-ligand: anti-ligand: ligand-active agent "sandwich" at the target site. Because the diagnostic or therapeutic agent is attached to a rapidly clearing ligand (rather than antibody, antibody fragment or other slowly clearing targeting moiety), this technique promises decreased non-target exposure to the active agent.

Alternate pretargeting methods eliminate the step of parenterally administering an anti-ligand clearing agent. These "two-step" procedures feature targeting moiety-ligand or targeting moiety-anti-ligand administration, followed by administration of active agent conjugated to the opposite member of the ligand-anti-ligand pair. As an optional step "1.5", in the two-step pretargeting methods of the present invention, a clearing agent (preferably other than ligand or anti-ligand alone) is administered to facilitate the clearance of circulating targeting moiety-containing conjugate.

In the two-step pretargeting approach, the clearing agent preferably does not become bound to the target cell population, either directly or through the previously administered and target cell bound targeting moiety-anti-ligand or targeting moiety-ligand conjugate. An example of two-step pretargeting involves the use of biotinylated human transferrin as a clearing agent for avidin-targeting moiety conjugate, wherein the size of the clearing agent results in liver clearance of transferrin-biotin-circulating avidin-targeting moiety complexes and substantially precludes association with the avidin-targeting moiety conjugates bound at target cell sites. (See, Goodwin, D. A., *Antibod. Immunoconj. Radiopharm.*, 4: 427–34, 1991).

The two-step pretargeting approach overcomes certain disadvantages associated with the use of a clearing agent in a three-step pretargeted protocol. More specifically, data obtained in animal models demonstrate that in vivo anti-ligand binding to a pretargeted targeting moiety-ligand conjugate (i.e., the cell-bound conjugate) removes the targeting moiety-ligand conjugate from the target cell. One explanation for the observed phenomenon is that the multivalent anti-ligand crosslinks targeting moiety-ligand conjugates on the cell surface, thereby initiating or facilitating internalization of the resultant complex. The apparent loss of targeting moiety-ligand from the cell might result from internal degradation of the conjugate and/or release of active agent from the conjugate (either at the cell surface or intracellularly). An alternative explanation for the observed phenomenon is that permeability changes in the target cell's membrane allow increased passive diffusion of any molecule into the target cell Also, some loss of targeting moiety-ligand may result from alteration in the affinity by subsequent binding of another moiety to the targeting moiety-ligand, e.g., anti-idiotype monoclonal antibody binding causes removal of tumor bound monoclonal antibody.

The present invention recognizes that this phenomenon (apparent loss of the targeting moiety-ligand from the target cell) may be used to advantage with regard to in vivo delivery of therapeutic agents generally, or to drug delivery in particular. For instance, a targeting moiety may be covalently linked to both ligand and therapeutic agent and administered to a recipient. Subsequent administration of anti-ligand crosslinks targeting moiety-ligand-therapeutic agent tripartite conjugates bound at the surface, inducing internalization of the tripartite conjugate (and thus the active agent). Alternatively, targeting moiety-ligand may be delivered to the target cell surface, followed by administration of anti-ligand-therapeutic agent.

In one aspect of the present invention, a targeting moiety-anti-ligand conjugate is administered in vivo; upon target localization of the targeting moiety-anti-ligand conjugate (i.e., and clearance of this conjugate from the circulation), an active agent-ligand conjugate is parenterally administered. This method enhances retention of the targeting moiety-anti-ligand: ligand-active agent complex at the target cell (as compared with targeting moiety-ligand: anti-ligand: ligand-active agent complexes and targeting moiety-ligand: anti-ligand-active agent complexes). Although a variety of ligand/anti-ligand pairs may be suitable for use within the claimed invention, a preferred ligand/anti-ligand pair is biotin/avidin.

In a second aspect of the invention, radioiodinated biotin and related methods are disclosed. Previously, radioiodinated biotin derivatives were of high molecular weight and were difficult to characterize. The radioiodinated biotin described herein is a low molecular weight compound that has been easily and well characterized.

In a third aspect of the invention, a targeting moiety-ligand conjugate is administered in vivo; upon target localization of the targeting moiety-ligand conjugate (i.e., and clearance of this conjugate from the circulation), a drug-anti-ligand conjugate is parenterally administered. This two-step method not only provides pretargeting of the targeting moiety conjugate, but also induces internalization of the subsequent targeting moiety-ligand-anti-ligand-drug complex within the target cell. Alternatively, another embodiment provides a three-step protocol that produces a targeting moiety-ligand:anti-ligand:ligand-drug complex at the surface, wherein the ligand-drug conjugate is administered simultaneously or within a short period of time after administration of anti-ligand (i.e., before the targeting moiety-ligand-anti-ligand complex has been removed from the target cell surface).

In a fourth aspect of the invention, methods for radiolabeling biotin with technetium-99m, rhenium-186 and rhenium-188 are disclosed. Previously, biotin derivatives were radiolabeled with indium-111 for use in pretargeted immunoscintigraphy (for instance, Virzi et al., *Nucl. Med. Biol.* 18: 719–26, 1991; Kalofonos et al., *J. Nucl. Med.* 31: 1791–96, 1990; Paganelli et al., *Canc. Res.* 51: 5960–66, 1991). However, $^{99}$Tc is a particularly preferred radionuclide for immunoscintigraphy due to (i) low cost, (ii) convenient supply and (iii) favorable nuclear properties. Rhenium-186 displays chelating chemistry very similar to $^{99m}$Tc, and is considered to be an excellent therapeutic radionuclide (i.e., a 3.7 day half-life and 1.07 MeV maximum particle that is similar to $^{131}$I). Therefore, the claimed methods for technetium and rhenium radiolabeling of biotin provide numerous advantages.

The "targeting moiety" of the present invention binds to a defined target cell population, such as tumor cells. Preferred targeting moieties useful in this regard include antibody and antibody fragments, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, *Univ. Mich. Med. Bull.,* 20: 284–6, 1956), affinity-purified polyclonal or fragments thereof (Chao et al., *Res. Comm. in Chem. Path. & Pharm.,* 9: 749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, *Nature,* 256: 495–97, 1975; *Eur. J. Immunol.,* 6: 511–19, 1976.

Human monoclonal antibodies or "humanized" murine antibody are also useful as targeting moieties in accordance with the present invention. For example, murine monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region, e.g., in a manner similar to that disclosed in European Patent Application No. 0,411,893 A2. Some murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

Types of active agents (diagnostic or therapeutic) useful herein include toxins, anti-tumor agents, drugs and radionuclides. Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting protein. However, while elimination of the toxin B chain decreases non-specific cytotoxicity, it also generally leads to decreased potency of the toxin A chain-targeting protein conjugate, as compared to the corresponding holotoxin-targeting protein conjugate.

Preferred toxins in this regard include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability, are also suitable for use herein.

Extremely highly toxic toxins, such as palytoxin, blocked ricin (see U.S. Pat. No. 5,239,062), bacterial toxins such as pseudomonas exotoxin, diphtheria toxin, fungal secondary metabolite toxins such as trichothecenes (e.g., roridin A and verrucarin A) and other highly toxic agents, such as potent chemotherapeutic agents such as actinomycin D and the like, are also contemplated for use in the practice of the present invention. Such extremely highly toxic molecules exhibit toxicities at micromolar and picomolar concentrations.

For example, palytoxin molecules having a preserved free terminal amino group are approximately 500-fold more toxic than palytoxin derivatives lacking such a free amine. In monkeys, palytoxin was found to have a LD50 of approximately 80 ng/kg. Consequently, an amino-derivatized palytoxin molecule is expected to exhibit an i.v. LD50 of approximately 40 μg/kg. Palytoxin is set forth herein as a prototypical molecule characterized by extremely high toxicity. Palytoxin is also set forth herein as a prototype of a membrane active drug. Other examples of membrane active drugs are amphotericin B, polymyxin B and the like.

In conventional targeted therapy, an active agent is bound to an antibody or other targeting moiety to form the diagnostic or therapeutic conjugate to be administered. The accretion of active agent to target sites is therefore dictated by the pharmacokinetics of the targeting moiety. Whole monoclonal antibodies, for example, generally require about 20–72 hours to achieve optimal target site accretion, while antibody fragments such as Fab and Fab' fragments generally require about 0–8 hours and F(ab')$_2$ fragments generally require about 8–24 hours. Consequently, the conjugate recipient's normal tissues are exposed to the active agent for the accretion time, leading to undesirable normal tissue toxicity. As a result of this normal tissue exposure, extremely highly toxic moieties cannot generally be employed in targeted therapy.

In the pretargeting approach; however, the pharmacokinetics of the active agent is decoupled from that of the targeting moiety. The targeting moiety is permitted to accrete to target sites while conjugated to a member of a ligand-anti-ligand pair. After that accretion occurs and substantially all of the non-targeted conjugate is cleared from the recipient's circulation, the highly toxic active agent is administered as a conjugate to the complementary member of the ligand-anti-ligand pair. Preferably, the toxin-ligand or toxin-anti-ligand has a short serum half life and is excreted via the renal pathway. In this manner, the toxic active agent either accretes to the target site where exertion of its toxic capability is desired, or it is rapidly removed from the recipient. This biodistribution of active agent facilitates the protection of normal tissues of the recipient from undesired toxicity. To enhance renal excretion, conjugation to a renal excretion promoting biodistribution directing molecule as discussed below with regard to trichothecenes may be employed. Alternatively, lower, therapeutically effective doses of active agent may be employed.

Palytoxin, the prototypical extremely highly toxic active agent, is characterized by the following: non-proteinaceous structure having a 2681 dalton molecular weight which exerts activity extracellularly by binding to cell surface receptor and creating a pore in cell membranes. The palytoxin structure is known and is described in Bignami et al., *Cancer Research*, 52: 5759–5764, 1992.

Palytoxin exhibits the following functional characteristics: cytotoxicity against cultures of lymphocytes, fibroblasts and normal or virus transformed epithelial cells. Palytoxin also depolarizes and lyses mammalian erythrocytes. Palytoxin appears to kill cells that express the $Na^+$ $K^+$-ATPase-associated toxin receptor, in contrast anticancer agents which are selectively toxic to metabolically active cycling cells. Pharmacological studies indicate that palytoxin greatly perturbs the sodium, potassium and calcium fluxes in cells. This perturbation causes a cascade of events, including damage to mitochondria as well as release of protease and phospholipase enzymes, and, ultimately, results in damage to the ultrastructure of the cell membrane.

For use in pretargeting methods of the present invention, palytoxin is conjugated to a ligand or to an anti-ligand. For illustrative purposes, palytoxin-biotin and palytoxin-streptavidin conjugation are discussed below and in Example XVI.

One general strategy for preparing a biotin-palytoxin conjugate is as follows:

1) protect the terminal amine nitrogen of palytoxin; and 2) alkylate a palytoxin hydroxyl group with a biotin-bearing alkylating agent such as an iodoacetyl or a bromoacetyl biotin derivative. This strategy does not afford selective functionalization of palytoxin, however. That is, the specific palytoxin hydroxyl group(s) that participate in the reaction are not preselected.

Iodoacetyl-long chain (LC) biotin (available from Pierce Chemical Company) may be reacted with amine-protected palytoxin in DMF and NaH to form a biotin-palytoxin conjugate. The degree of biotin derivatization of palytoxin will depend, among other things, upon the offering ratio of iodoacetyl-LC-biotin:palytoxin. Generally, biotin derivatization ranging from 1 to about 5 biotins/palytoxin will be employed. Deprotection of the terminal palytoxin amine group may be conducted prior to administration to a recipient of the palytoxin-biotin conjugate. In these circumstances, it is preferred that an acid or base cleavable protecting group, such as BOC, TFA or the like, is used in the protection step. If in vivo deprotection is contemplated, functional groups that are susceptible to enzyme cleavage (such as those discussed below with regard to cleavable linkages) are preferred. Similar routes may be employed using alternative iodoacetyl-linker-biotin molecules.

Alternatively, a ligand or an anti-ligand may be linked to palytoxin selectively. That is, the linkage may be formed employing a unique functionality of the palytoxin molecule. For example, a COOH moiety may be liberated by treating a protected amine palytoxin derivative with peptidase. An active ester is then formed using that liberated COOH, and the active ester so formed is reacted with a derivatized biotin amino group. Still another possibility is derivatization at the C-55 position (unique acetal functionality) of the palytoxin structure. Following protection of the free palytoxin amine, the latent ketone in the ring structure may be derivatized with a biotin amine in the presence of $NaCNBH_3$. The product of the reductive animation may be represented as follows:

Biotin-Linker-$NH-CH_2$-palytoxin where the carbon atom is the C-55 atom in the palytoxin structure and the Linker is the non-amine portion of a homo- or hetero-bifunctional linker bearing at least one amine group.

Another general palytoxin-biotin conjugate useful in the practice of the present invention is coupled via the terminal amine of the palytoxin molecule. For example, an active ester biotin derivative such as N-hydroxysuccinimido-biotin, or a cleavable linker, may be coupled with palytoxin bearing a free, unprotected terminal amine group at pH 7.5.

Preferred cleavable linkers useful in the practice of the present invention are linkers characterized by a physiological half-life greater than the time necessary for accretion of the palytoxin-biotin conjugate to target sites. Preferably, the physiological stability half-life of the linker is from about 2 to about 5 times the serum clearance of the biotinylated palytoxin conjugate. In this manner, streptavidin is pretargeted to target sites and substantially removed from the recipient's circulation; biotin-cleavable linker-palytoxin is administered and localizes to the pretargeted streptavidin; and palytoxin is released from the conjugate and binds to a target site receptor. Consequently, the palytoxin delivered to the target site will be in its native, more highly toxic, free amine form. Exemplary cleavable linkers useful in the practice of the present invention are hydrazido thiourea linkers (formed, for example, by reaction of $NH_2$-derivatized palytoxin isothiocyanate and biotin hydrazide); long chain amide linkers susceptible to biotinidase (formed, for example, from free amine-bearing palytoxin and long chain-biotin-NHS ester available from Sigma Chemical Co., St. Louis, Mo.); ester linkers susceptible to esterases (formed, for example, from free-amine bearing palytoxin and an active ester form of the reaction product of biotin and HO—CO—$(CH_2)_n$—Br where n ranges from 2 to 5); or the like.

Palytoxin-streptavidin conjugates may be employed, for example, in two-step pretargeting protocols of the present invention. That is, a biotinylated targeting moiety may be administered and permitted to localize to target. Optionally, circulating biotin-targeting moiety conjugate may be cleared using a clearing agent (e.g., galactosylated-avidin or the like) or other clearance mechanism. Next, palytoxin-streptavidin conjugate is administered and binds to the pretargeted biotin-containing conjugate. The streptavidin component of the conjugate may also decrease the whole body toxicity of palytoxin by binding the free amine group of the palytoxin or by the folding of streptavidin relative to the palytoxin structure. Palytoxin-streptavidin conjugation may be conducted employing the COOH-liberated palytoxin derivative described above, for example.

Alternatively, a prodrug (i.e., inactive) form of palytoxin, such as N-(4'-hydroxyphenylacetyl)-palytoxin described in Bignami et al., *Cancer Research,* 52: 5759–5764, 1992, and activated by penicillin G amidase (PGA), may be employed in two-step or three-step pretargeting protocols of the present invention.

A two-step pretargeting embodiment of the present invention involves:

administering to the recipient a first conjugate comprising a targeting moiety; a member of a ligand-anti-ligand binding pair; and an enzyme capable of activating a prodrug, wherein the first conjugate localizes to a target site;

optionally administering to the recipient a clearing agent capable of directing the clearance of circulating conjugate from the recipient or optionally treating the recipient with a clearing device or an alternative clearing procedure to substantially remove circulating conjugate from the recipient; and administering to the recipient a second conjugate comprising a prodrug and a ligand/anti-ligand binding pair member, wherein the second conjugate binding pair member is complementary to that of the first conjugate and wherein the second conjugate is cleared from the recipient rapidly and, preferably, via the renal pathway.

For example, an non-internalizing, anti-carcinoma $IgG_{2a}$ antibody, such as L6, may be conjugated to streptavidin and PGA via techniques described herein as well as art-recognized methods therefor. This PGA-L6-streptavidin conjugate is administered and permitted to localize to target sites. Preferably, a clearing agent, such as galactose-HSA-biotin is administered at a later time point to facilitate clearance of circulating PGA-L6-streptavidin. A few hours later, N-(4'-hydroxyphenylacetyl)-palytoxin-biotin conjugate is administered and either accretes to pretargeted PGA-L6-streptavidin or is eliminated from the recipient's circulation by the recipient's endogenous mechanisms therefor.

In alternative two-step protocols, the ligand/anti-ligand interaction is one involving enzymes and enzyme inhibitors. Such a two-step pretargeting protocol includes:

administering to the recipient a first conjugate comprising a targeting moiety; and an enzyme capable of activating a prodrug, wherein the first conjugate localizes to a target site;

optionally administering to the recipient a clearing agent comprising an enzyme inhibitor capable of directing the clearance of circulating conjugate from the recipient or optionally treating the recipient with a clearing device or an alternative clearing procedure to substantially remove circulating conjugate from the recipient; and administering to the recipient a prodrug, wherein the prodrug is converted into active, cytotoxic form at the sites of pretargeted enzyme.

For example, an L6-PGA conjugate may be administered and permitted to localize to target sites. Preferably, a clearing agent, such as galactose-HSA-PGA irreversible inhibitor or a conjugate incorporating a reversible or irreversible PGA inhibitor and a large, non-extravascular permeating molecule is administered at a later time point to facilitate clearance of circulating PGA-L6-streptavidin.

An exemplary large, non-extravascular permeating molecule, is dextran. Other polymers, polymeric particulates or liposomes, as discussed elsewhere herein, may also be employed.

Exemplary irreversible inhibitors useful in the practice of the present invention may be designed by incorporating a reactive group, such as an iodoacetyl group or an amide group, in a molecule that resembles a substrate. Iodoacetamide, for example, is an irreversible inhibitor of many enzymes that contain a cysteine residue in the active site. Exemplary reversible inhibitors of PGA are other amide substrates, e.g., peptides such as triglycine or 4-hydroxyphenylacetylglycine and the like.

A few hours later, a prodrug form of an active agent is administered. For example, N-(4'-hydroxyphenyl-acetyl)-palytoxin is administered, which molecule either accretes to pretargeted PGA-L6 or is eliminated from the recipient's circulation by the recipient's endogenous mechanisms therefor.

One alternative to the optional clearance step set forth above is simply to allow an amount of time to pass that is sufficient to permit the recipient's native clearance mechanisms to substantially remove circulating first conjugate.

The three-step approach involves:

administering to the recipient a first conjugate comprising a targeting moiety; an enzyme; and a ligand, wherein the first conjugate localizes to a target site;

administering to the recipient an anti-ligand; or a anti-ligand-containing conjugate; and administering to the recipient a prodrug, wherein the prodrug is converted to active, cytotoxic form at sites of pretargeted enzyme.

While the methods set forth above have been described with regard to the N-(4'-hydroxyphenyl-acetyl)palytoxin/PGA prodrug/enzyme pair, those methods are amenable to other such pairs. An example of a prodrug/enzyme pair useful in the practice of the present invention is a phosphate form of a drug (e.g., phenol mustard phosphate, etoposide phosphate, mitomycin phosphate, doxorubicin phosphate and the like) and an alkaline phosphatase enzyme. See, for example, Wallace et al., *Bioconj. Chem.*, 2: 349–352, 1991. Another example is 5-fluorocytosine (5FC)/cytosine deaminase (CDase), described in Senter et al., *Bioconj. Chem.*, 2: 447–451, 1991. An additional example involves activation of beta-lactam prodrugs by beta-lactamase. See, for example, Meyer et al., *Bioconj. Chem.*, 3: 42–48, 1992.

Preferred drugs suitable for use herein include conventional chemotherapeutics, such as vinblastine, doxorubicin, bleomycin, methotrexate, 5-fluorouracil, 6-thioguanine, cytarabine, cyclophosphamide and cis-platinum, as well as other conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14. A particularly preferred drug within the present invention is a trichothecene.

Trichothecenes are drugs produced by soil fungi of the class *Fungi imperfecti* or isolated from *Baccharus megapotamica* (Bamburg, J. R. *Proc. Molec. Subcell. Biol.* 8: 41–110, 1983; Jarvis & Mazzola, *Acc. Chem. Res.* 15: 338–395, 1982). They appear to be the most toxic molecules that contain only carbon, hydrogen and oxygen (Tamm, C. *Fortschr. Chem. Org. Naturst.* 31: 61–117, 1974). They are all reported to act at the level of the ribosome as inhibitors of protein synthesis at the initiation, elongation, or termination phases.

There are two broad classes of trichothecenes: those that have only a central sesquiterpenoid structure and those that have an additional macrocyclic ring (simple and macrocyclic trichothecenes, respectively). The simple trichothecenes may be subdivided into three groups (i.e., Group A, B, and C) as described in U.S. Pat. Nos. 4,744,981 and 4,906,452 (incorporated herein by reference). Representative examples of Group A simple trichothecenes include: Scirpene, Roridin C, dihydrotrichothecene, Scirpen-4, 8-diol, Verrucarol, Scirpentriol, T-2 tetraol, pentahydroxyscirpene, 4-deacetylneosolaniol, trichodermin, deacetylcalonectrin, calonectrin, diacetylverrucarol, 4-monoacetoxyscirpenol, 4,15-diacetoxyscirpenol, 7-hydroxydiacetoxyscirpenol, 8-hydroxydiacetoxy-scirpenol (Neosolaniol), 7,8-dihydroxydiacetoxyscirpenol, 7-hydroxy-8-acetyldiacetoxyscirpenol, 8-acetylneosolaniol, NT-1, NT-2, HT-2, T-2, and acetyl T-2 toxin. Representative examples of Group B simple trichothecenes include: Trichothecolone, Trichothecin, deoxynivalenol, 3-acetyldeoxynivalenol, 5-acetyldeoxynivalenol, 3,15-diacetyldeoxynivalenol, Nivalenol, 4-acetylnivalenol (Fusarenon-X), 4,15-idacetylnivalenol, 4,7,15-triacetylnivalenol, and tetra-acetylnivalenol. Representative examples of Group C simple trichothecenes include: Crotocol and Crotocin. Representative macrocyclic trichothecenes include Verrucarin A, Verrucarin B, Verrucarin J (Satratoxin C), Roridin A, Roridin D, Roridin E (Satratoxin D), Roridin H, Satratoxin F, Satratoxin G, Satratoxin H, Vertisporin, Mytoxin A, Mytoxin C, Mytoxin B, Myrotoxin A, Myrotoxin B, Myrotoxin C, Myrotoxin D, Roritoxin A, Roritoxin B, and Roritoxin D. In addition, the general "trichothecene" sesquiterpenoid ring structure is also present in compounds termed "baccharins" isolated from the higher plant *Baccharis megapotamica*, and these are described in the literature, for instance as disclosed by Jarvis et al. (Chemistry of Alleopathy, ACS Symposium Series No. 268: ed. A. C. Thompson, 1984, pp. 149–159).

The present invention provides for effective delivery of active agents including toxins. The decoupling of the pharmacokinetics of the targeting moiety (generally slow), and the toxin (generally fast when administered intravenously, half-life less than about 5 minutes with longer lived metabolites) in combination with the high affinity interaction between a ligand-anti-ligand pair is responsible for this improvement. When the toxin active agents are not themselves generally rapidly cleared (typically via the hepatic pathway), conjugates containing such active agents are preferably constructed to impart relatively rapid, preferably renal, clearance thereto. Derivatization of the toxin with ligand or with anti-ligand may be insufficient to redirect the biodistribution of the toxin active agent. Alternatively, the active agent may be administered in a lower, but therapeutically effective, dose. In this manner, the non-target tissue of the recipient of the toxin active agent does not suffer prolonged exposure to the toxic active agent.

Toxin molecules, such as *Pseudomonas exotoxin* (PE) and trichothecenes, are primarily metabolized in the liver. Consequently, liver toxicity is associated with administration of PE. Also, administration of anti-tumor agents, such as IL-2 and TNF, has been shown to result in liver toxicity. Active agents characterized by such a biodistribution pattern may be accommodated in two-step or three-step pretargeting protocols of the present invention in two ways.

First, low doses of the active agent-ligand or active agent-anti-ligand may be given. Because of the high affinity of ligand for the complementary anti-ligand, a therapeutically effective dose may be delivered to the tumor, without the necessity for active agent-targeting moiety binding during targeting moiety accretion to target site. The active agent-ligand or active agent-anti-ligand are generally processed by the recipient's liver. Because of the lower dose of active agent administered to the recipient and the decreased circulation time of that active agent in the recipient (active agent circulation half-life is generally less than the time for maximum target site accretion of the targeting moiety a therapeutically effective dose may be delivered to the target site without an unmanageable level of toxicity being delivered to non-target sites. Doses of active agent, ranging from nanograms to about micrograms may be administered in this manner, with the attending physician being responsible for the dosing choice in light of the condition and treatment history of the particular recipient.

Alternatively, the active agent may be coupled to a polymeric molecule of sufficient size to direct the biodistribution of the conjugate to the kidneys. Suitable polymeric molecules preferably range in molecular weight between from about 5000 to about 50,000 daltons. Polymers of less than about 5000 daltons will not generally direct the biodistribution of large active agents. Polymers of greater than 50,000 daltons are likely to be metabolized in the liver. Exemplary polymers useful in this aspect of the present invention include dextran, polylysine, polyglytamate, oligosaccharides of defined size (e.g., from about 5 to about 50 kD) and the like. Methods for coupling dextran, for example, to ligands and anti-ligands are discussed in the examples below.

Active agent-polymer-ligand or -anti-ligand conjugates can be administered at high active agent doses, because such conjugates exhibit rapid renal clearance. Consequently, non-target tissues of the recipient are exposed to the active agent for only a short time until the active agent is either bound at the target site or processed via renal excretion As a result, doses of active agent, ranging from about micrograms to about milligrams ($10^{-6}$ to $10^{-3}$ M), may be administered in this manner.

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl)-3-(2,6-dioxo-3-piperidyl)-1-nitrosourea, N,N'-hexamethylene-bis-acetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, carboplatin, amsacrine, caracemide, iproplatin, misonidazole, dihydro-5-azacytidine, 4'-deoxy-doxorubicin, menogaril, triciribine phosphate, fazarabine, tiazofurin, teroxirone, ethiofos, N-(2-hydroxyethyl)-2-nitro-1H-imidazole-1-acetamide, mitoxantrone, acodazole, amonafide, fludarabine phosphate, pibenzimol, didemnin B, merbarone, dihydrolenperone, flavone-8-acetic acid, oxantrazole, ipomeanol, trimetrexate, deoxyspergualin, echinomycin, and dideoxycytidine (see *NCI Investigational Drugs, Pharmaceutical Data* 1987, NIH Publication No. 88-2141, Revised November 1987) are also preferred.

Radionuclides useful within the present invention include gamma-emitters, positron-emitters, Auger electron-emitters, X-ray emitters and fluorescence-emitters, with beta- or alpha-emitters preferred for therapeutic use. Radionuclides are well-known in the art and include $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Ga, $^{68}$Ga, $^{64}$Cu, $^{67}$Cu, $^{75}$Br, $^{76}$Br, $^{77}$Br, $^{99m}$Tc, $^{11}$C, $^{13}$N, $^{15}$O, $^{166}$Ho and $^{18}$F. Preferred therapeutic radionuclides include $^{188}$Re, $^{186}$Re, $^{203}$Pb $^{212}$Pb, $^{212}$Bi, $^{109}$Pd, $^{64}$Cu, $^{67}$Cu, $^{90}$Y, $^{125}$I, $^{131}$I, $^{77}$Br $^{211}$At, $^{97}$Ru, $^{105}$Rh, $^{198}$Au, $^{166}$Ho and $^{199}$Ag or $^{177}$Lu.

Other anti-tumor agents, e.g., agents active against proliferating cells, are administrable in accordance with the present invention. Exemplary anti-tumor agents include cytokines and other moieties, such as interleukins (e.g.,IL-2, IL-4, IL-6, IL-12 and the like), transforming growth factor-beta, lymphotoxin, tumor necrosis factor, interferons (e.g., gamma-interferon), colony stimulating factors (e.g., GM-CSF, M-CSF and the like), vascular permeability factor or the like, lectin inflammatory response promoters (selectins), such as L-selectin, E-selectin, P-selectin or the like, proteinaceous moieties such as C1q and NK receptor protein, and like molecules.

Also, suitable anti-tumor agents include compounds which inhibit angiogenesis and therefore inhibit metastasis. Examples of such moieties include protamine and platelet factor 4 (described in U.S. Pat. No. 5,284,827). These compounds are also useful for treatment of diseases involving angiogenic dysfunctions such as diabetic retinopathy, retrolental fibroplasia, neurovascular glaucoma, psoriasis, angiofibromas, immune and non-immune inflammation, capillary proliferation with atherosclerotic plaques, hemangiomas and Kaposi's Sarcoma.

Ligands suitable for use within the present invention include biotin, haptens, lectins, epitopes, dsDNA fragments, enzyme inhibitors and analogs and derivatives thereof. Useful complementary anti-ligands include avidin (for biotin), carbohydrates (for lectins) and antibody, fragments or analogs thereof, including mimetics (for haptens and epitopes) and zinc finger proteins (for dsDNA fragments) and enzymes (for enzyme inhibitors). Preferred ligands and anti-ligands bind to each other with an affinity of at least about $k_D \geq 10^9$ M.

One component to be administered in a preferred two-step pretargeting protocol is a targeting moiety-anti-ligand or a targeting moiety-ligand conjugate. In three-step pretargeting, a preferred component for administration is a targeting moiety-ligand conjugate.

A preferred targeting moiety useful in these embodiments of the present invention is a monoclonal antibody. Protein-protein conjugations are generally problematic due to the formation of undesirable byproducts, including high molecular weight and cross-linked species, however. A non-covalent synthesis technique involving reaction of biotinylated antibody with streptavidin has been reported to result in substantial byproduct formation. Also, at least one of the four biotin binding sites on the streptavidin is used to link the antibody and streptavidin, while another such binding site may be sterically unavailable for biotin binding due to the configuration of the streptavidin-antibody conjugate.

Thus, covalent streptavidin-antibody conjugation is preferred, but high molecular weight byproducts are often obtained. The degree of crosslinking and aggregate formation is dependent upon several factors, including the level of protein derivitization using heterobifunctional crosslinking reagents. Sheldon et al., *Appl. Radiat. Isot.* 43: 1399–1402, 1992, discuss preparation of covalent thioether conjugates by reacting succinimidyl 4-(N-maleimidomethyl) cyclohexane-1-carboxylate (SMCC)-derivatized antibody and iminothiolane-derivatized streptavidin.

Streptavidin-proteinaceous targeting moiety conjugates are preferably prepared as described in Example XI below, with the preparation involving the steps of: preparation of SMCC-derivatized streptavidin; preparation of DTT-reduced proteinaceous targeting moiety; conjugation of the two prepared moieties; and purification of the monosubstituted or disubstituted (with respect to streptavidin) conjugate from crosslinked (antibody-streptavidin-antibody) and aggregate species and unreacted starting materials. The purified fraction is preferably further characterized by one or more of the following techniques: HPLC size exclusion, SDS-PAGE, immunoreactivity, biotin binding capacity and in vivo studies.

Alternatively, thioether conjugates useful in the practice of the present invention may be formed using other thiolating agents, such as SPDP, iminothiolane, SATA or the like, or other thio-reactive heterobifunctional cross linkers, such as m-maleimidobenzoyl-N-hydroxysuccinimide ester, N-succinimidyl(4-iodoacetyl)aminobenzoate or the like.

Streptavidin-proteinaceous targeting moiety conjugates of the present invention can also be formed by conjugation of a lysine epsilon amino group of one protein with a maleimide-derivatized form of the other protein. For example, at pH 8–10, lysine epsilon amino moieties react with protein maleimides, prepared, for instance, by treatment of the protein with SMCC, to generate stable amine covalent conjugates. In addition, conjugates can be prepared by reaction of lysine epsilon amino moieties of one protein with aldehyde functionalities of the other protein. The resultant imine bond is reducible to generate the corresponding stable amine bond. Aldehyde functionalities may be generated, for example, by oxidation of protein sugar residues or by reaction with aldehyde-containing heterobifunctional cross linkers.

Another method of forming streptavidin-targeting moiety conjugates involves immobilized iminobiotin that binds SMCC-derivatized streptavidin. In this conjugation/purification method, the reversible binding character of iminobiotin (immobilized) to streptavidin is exploited to readily separate conjugate from the unreacted targeting moiety. Iminobiotin binding can be reversed under conditions of lower pH and elevated ionic strength, e.g., $NH_2OAc$, pH 4 (50 mM) with 0.5 M NaCl.

For streptavidin, for example, the conjugation/purification proceeds as follows:

SMCC-derivatized streptavidin is bound to immobilized iminobiotin (Pierce Chemical Co., St. Louis, Mo.), preferably in column format;

a molar excess (with respect to streptavidin) of DTT-reduced antibody (preferably free of reductant) is added to the nitrogen-purged, phosphate-buffered iminobiotin column wherein the SMCC-streptavidin is bound (DTT-reduced antibody will saturate the bound SMCC-streptavidin, and unbound reduced antibody passing through the column can be reused);

the column is washed free of excess antibody; and a buffer that lowers the pH and increases ionic strength is added to the column to elute streptavidin-antibody conjugate in pure form.

As indicated above, targeting moiety-mediated ligand-anti-ligand pretargeting involves the localization of either targeting moiety-ligand or targeting moiety-anti-ligand at target tissue. Often, peak uptake to such target tissue is achieved before the circulating level of targeting moiety-containing conjugate in the blood is sufficiently low to permit the attainment of an optimal target-to-non-target conjugate ratio. To obviate this problem, two approaches are useful. The first approach allows the targeting moiety-containing conjugate to clear from the blood by "natural", or endogenous clearance mechanisms. This method is complicated by variations in systemic clearance of proteins and by endogenous ligand or anti-ligand. For example, endogenous biotin may interfere with the preservation of biotin binding sites on a streptavidin-targeting moiety conjugate.

The second approach for improving targeting moiety-ligand or targeting moiety-anti-ligand conjugate target-to-blood ratio "chases" the conjugate from the circulation through in vivo complexation of conjugate with a molecule constituting or containing the complementary anti-ligand or ligand. When biotinylated antibodies are used as a ligand-targeting moiety conjugate, for example, avidin forms relatively large aggregated species upon complexation with the circulating biotinylated antibody, which aggregated species are rapidly cleared from the blood by the RES uptake. See, for example, U.S. Pat. No. 4,863,713. One problem with this method, however, is the potential for cross-linking and internalizing tumor-bound biotinylated antibody by avidin.

When avidin-targeting moiety conjugates are employed, poly-biotinylated transferrin has been used to form relatively large aggregated species that are cleared by RES uptake. See, for example, Goodwin, *J. Nucl. Med.* 33(10): 1816–18, 1992). Poly-biotinylated transferrin also has the potential for cross-linking and internalizing tumor-bound avidinylated-targeting moiety, however. In addition, both "chase" methodologies involve the prolonged presence of aggregated moieties of intermediate, rather than large, size (which are not cleared as quickly as large size particles by RES uptake), thereby resulting in serum retention of subsequently administered ligand-active agent or anti-ligand-active agent. Such serum retention unfavorably impacts the target cell-to-blood targeting ratio.

The present invention provides clearing agents of protein and non-protein composition having physical properties facilitating use for in vivo complexation and blood clearance of anti-ligand/ligand (e.g., avidin/biotin)-targeting moiety (e.g., antibody) conjugates. These clearing agents are useful in improving the target:blood ratio of targeting moiety conjugate. Other applications of these clearing agents include lesional imaging or therapy involving blood clots and the like, employing antibody-active agent delivery modalities. For example, efficacious anti-clotting agent provides rapid target localization and high target:non-target targeting ratio. Active agents administered in pretargeting protocols of the present invention using efficient clearing agents are targeted in the desirable manner and are, therefore, useful in the imaging/therapy of conditions such as pulmonary embolism and deep vein thrombosis.

Clearing agents useful in the practice of the present invention preferably exhibit one or more of the following characteristics:

rapid, efficient complexation with targeting moiety-ligand (or anti-ligand) conjugate in vivo;

rapid clearance from the blood of targeting moiety conjugate capable of binding a subsequently administered complementary anti-ligand or ligand containing molecule;

high capacity for clearing (or inactivating) large amounts of targeting moiety conjugate; and low immunogenicity.

Preferred clearing agents include hexose-based and non-hexose based moieties. Hexose-based clearing agents are molecules that have been derivatized to incorporate one or more hexoses (six carbon sugar moieties) recognized by Ashwell receptors or other receptors such as the mannose/ N-acetylglucosamine receptor which are associated with endothelial cells and/or Kupffer cells of the liver or the mannose 6-phosphate receptor. Exemplary of such hexoses are galactose, mannose, mannose 6-phosphate, N-acetylglucosamine and the like. Other moieties recognized by Ashwell receptors, including glucose, N-galactosamine, N-acetylgalactosamine, thioglycosides of galactose and, generally, D-galactosides and glucosides or the like may also be used in the practice of the present invention. Galactose is the prototypical clearing agent hexose derivative for the purposes of this description. Galactose thioglycoside conjugation to a protein is preferably accomplished in accordance with the teachings of Lee et al., "2-Imino-2-methoxyethyl 1-Thioglycosides: New Reagents for Attaching Sugars to Proteins," *Biochemistry*, 15(18): 3956, 1976. Another useful galactose thioglycoside conjugation method is set forth in Drantz et al, "Attachment of Thioglycosides to Proteins: Enhancement of Liver Membrane Binding," *Biochemistry*, 15(18): 3963, 1976. Thus, galactose-based and non-galactose based molecules are discussed below.

Protein-type galactose-based clearing agents include proteins having endogenous exposed galactose residues or which have been derivatized to expose or incorporate such galactose residues. Exposed galactose residues direct the clearing agent to rapid clearance by endocytosis into the liver through specific receptors therefor (Ashwell receptors). These receptors bind the clearing agent, and induce endocytosis into the hepatocyte, leading to fusion with a lysosome and recycle of the receptor back to the cell surface. This clearance mechanism is characterized by high efficiency, high capacity and rapid kinetics.

An exemplary clearing agent of the protein-based/galactose-bearing variety is the asialoorosomucoid derivative of human alpha-1 acid glycoprotein (orosomucoid, molecular weight=41,000 Dal, isoelectric point=1.8–2.7). The rapid clearance from the blood of asialoorosomucoid has been documented by Galli, et al., *J. of Nucl. Med. Allied Sci.* 32(2): 110–16, 1988.

Treatment of orosomucoid with neuraminidase removes sialic acid residues, thereby exposing galactose residues. Other such derivatized clearing agents include, for example, galactosylated albumin, galactosylated-IgM, galactosylated-IgG, asialohaptoglobin, asialofetuin, asialoceruloplasmin and the like.

Human serum albumin (HSA), for example, may be employed in a clearing agent of the present invention as follows:

(Hexose)$_m$—Human Serum Albumin (HSA)—(Ligand)$_n$, wherein n is an integer from 1 to about 10 and m is an integer from 1 to about 25 and wherein the hexose is recognized by Ashwell receptors. In a preferred embodiment of the present invention the ligand is biotin and the hexose is galactose. More preferably, HSA is derivatized with from 10–20 galactose residues and 1–5 biotin residues. Still more preferably, HSA clearing agents of the present invention are derivatized with from about 12 to about 15 galactoses and 3 biotins. Derivatization with both galactose and biotin are conducted in a manner sufficient to produce individual clearing agent molecules with a range of biotinylation levels that averages a recited whole number, such as 1, biotin. Derivatization with 3 biotins, for example, produces a product mixture made up of individual clearing agent molecules, substantially all of which having at least one biotin residue. Derivatization with 1 biotin produces a clearing agent product mixture, wherein a significant portion of the individual molecules are not biotin derivatized. The whole numbers used in this description refer to the average biotinylation of the clearing agents under discussion.

In addition, clearing agents based upon human proteins, especially human serum proteins, such as, for example, orosomucoid and human serum albumin, human IgG, human-anti-antibodies of IgG and IgM class and the like, are less immunogenic upon administration into the serum of a human recipient. Another advantage of using asialoorosomucoid is that human orosomucoid is commercially available from, for example, Sigma Chemical Co, St. Louis, Mo.

One way to prevent clearing agent compromise of target-bound conjugate through direct complexation is through use of a clearing agent of a size sufficient to render the clearing agent less capable of diffusion into the extravascular space and binding to target-associated conjugate. This strategy is useful alone or in combination with the aforementioned recognition that exposed galactose residues direct rapid liver uptake. This size-exclusion strategy enhances the effectiveness of non-galactose-based clearing agents of the present invention. The combination (exposed galactose and size) strategy improves the effectiveness of "protein-type" or "polymer-type" galactose-based clearing agents.

Galactose-based clearing agents include galactosylated, biotinylated proteins (to remove circulating streptavidin-targeting moiety conjugates, for example) of intermediate molecular weight (ranging from about 40,000 to about 200,000 Dal), such as biotinylated asialoorosomucoid, galactosyl-biotinyl-human serum albumin or other galactosylated and biotinylated derivatives of non-immunogenic soluble natural proteins, as well as biotin- and galactose-derivatized polyglutamate, polylysine, polyarginine, polyaspartate and the like. High molecular weight moieties (ranging from about 200,000 to about 1,000,000 Dal) characterized by poor target access, including galactosyl-biotinyl-IgM or -IgG (approximately 150,000 Dal) molecules, as well as galactose- and biotin-derivatized transferrin conjugates of human serum albumin, IgG and IgM molecules and the like, can also be used as clearing agents of the claimed invention. Chemically modified polymers of intermediate or high molecular weight (ranging from about 40,000 to about 1,000,000 Dal), such as galactose- and biotin-derivatized dextran, hydroxypropylmethacrylamide polymers, polyvinylpyrrolidone-polystyrene copolymers, divinyl ether-maleic acid copolymers, pyran copolymers, or PEG, also have utility as clearing agents in the practice of the present invention. In addition, rapidly clearing biotinylated liposomes (high molecular weight moieties with poor target access) can be derivatized with galactose and biotin to produce clearing agents for use in the practice of the present invention.

A further class of clearing agents useful in the present invention involve small molecules (ranging from about 500 to about 10,000 Dal) derivatized with galactose and biotin that are sufficiently polar to be confined to the vascular space as an in vivo volume of distribution. More specifically, these agents exhibit a highly charged structure and, as a result, are not readily distributed into the extravascular volume, because they do not readily diffuse across the lipid membranes lining the vasculature. Exemplary of such clearing agents are mono- or poly-biotin-derivatized 6,6'-[(3,3'-dimethyl[1,1'-biphenyl]-4,4'-diyl)bis(azo) bis[4-amino-5-hydroxy-1,3-naphthalene disulfonic acid] tetrasodium salt, mono- or poly-biotinyl-galactose-derivatized polysulfated dextran-biotin, mono- or poly-biotinyl-galactose-derivatized dextran-biotin and the like.

The galactose-exposed or -derivatized clearing agents are preferably capable of (1) rapidly and efficiently complexing with the relevant ligand- or anti-ligand-containing conjugates via ligand-anti-ligand affinity; and (2) clearing such complexes from the blood via the galactose receptor, a liver specific degradation system, as opposed to aggregating into complexes that are taken up by the generalized RES system, including the lung and spleen. Additionally, the rapid kinetics of galactose-mediated liver uptake, coupled with the affinity of the ligand-anti-ligand interaction, allow the use of intermediate or even low molecular weight carriers.

Non-galactose residue-bearing moieties of low or intermediate molecular weight (ranging from about 40,000 to about 200,000 Dal) localized in the blood may equilibrate with the extravascular space and, therefore, bind directly to target-associated conjugate, compromising target localization. In addition, aggregation-mediated clearance mechanisms operating through the RES system are accomplished using a large stoichiometric excess of clearing agent. In contrast, the rapid blood clearance of galactose-based clearing agents used in the present invention prevents equilibration, and the high affinity ligand-anti-ligand binding allows the use of low stoichiometric amounts of such galactose-based clearing agents. This feature further diminishes the potential for galactose-based clearing agents to compromise target-associated conjugate, because the absolute amount of such clearing agent administered is decreased.

Clearing agent evaluation experimentation involving galactose- and biotin-derivatized clearing agents of the present invention is detailed in Examples XIII and XV. Specific clearing agents of the present invention that were examined during the Example XV experimentation are (1) asialoorosomucoid-biotin, (2) human serum albumin derivatized with galactose and biotin, and (3) a 70,000 dalton molecular weight dextran derivatized with both biotin and galactose. The experimentation showed that proteins and polymers are derivatizable to contain both galactose and biotin and that the resultant derivatized molecule is effective in removing circulating streptavidin-protein conjugate from the serum of the recipient. Biotin loading was varied to determine the effects on both clearing the blood pool of circulating avidin-containing conjugate and the ability to deliver a subsequently administered biotinylated isotope to a target site recognized by the streptavidin-containing conjugate. The effect of relative doses of the administered components with respect to clearing agent efficacy was also examined.

Protein-type and polymer-type non-galactose-based clearing agents include the agents described above, absent galactose exposure or derivitization and the like. These clearing agents act through an aggregation-mediated RES mechanism. In these embodiments of the present invention, the clearing agent used will be selected on the basis of the target organ to which access of the clearing agent is to be excluded. For example, high molecular weight (ranging from about 200,000 to about 1,000,000 Dal) clearing agents will be used when tumor targets or clot targets are involved.

Another class of clearing agents includes agents that do not remove circulating ligand or anti-ligand/targeting moiety conjugates, but instead "inactivate" the circulating conjugates by blocking the relevant anti-ligand or ligand binding sites thereon. These "cap-type" clearing agents are preferably small (500 to 10,000 Dal) highly charged molecules, which exhibit physical characteristics that dictate a volume of distribution equal to that of the plasma compartment (i.e., do not extravasate into the extravascular fluid volume). Exemplary cap-type clearing agents are polybiotin-derivatized 6,6'-[(3,3'-dimethyl[1,1'-biphenyl]-4,4'-diyl)bis(azo) bis[4-amino-5-hydroxy-1,3-naphthalene disulfonic acid] tetrasodium salt, poly-biotinyl-derivatized polysulfated dextran-biotin, mono- or poly-biotinyl-derivatized dextran-biotin and the like.

Cap-type clearing agents are derivatized with the relevant anti-ligand or ligand, and then administered to a recipient of previously administered ligand/ or anti-ligand/targeting moiety conjugate. Clearing agent-conjugate binding therefore diminishes the ability of circulating conjugate to bind any subsequently administered active agent-ligand or active agent-anti-ligand conjugate. The ablation of active agent binding capacity of the circulating conjugate increases the efficiency of active agent delivery to the target, and increases the ratio of target-bound active agent to circulating active agent by preventing the coupling of long-circulating serum protein kinetics with the active agent. Also, confinement of the clearing agent to the plasma compartment prevents compromise of target-associated ligand or anti-ligand.

Clearing agents of the present invention may be administered in single or multiple doses. A single dose of biotinylated clearing agent, for example, produces a rapid decrease in the level of circulating targeting moiety-streptavidin, followed by a small increase in that level, presumably caused, at least in part, by re-equilibration of targeting moiety-streptavidin within the recipient's physiological compartments. A second or additional clearing agent doses may then be employed to provide supplemental clearance of targeting moiety-streptavidin. Alternatively, clearing agent may be infused intravenously for a time period sufficient to clear targeting moiety-streptavidin in a continuous manner.

Other types of clearing agents and clearance systems are also useful in the practice of the present invention to remove circulating targeting moiety-ligand or -anti-ligand conjugate from the recipient's circulation. Particulate-based clearing agents, for example, are discussed in Example IX. In addition, extracorporeal clearance systems are discussed in Example IX. in vivo clearance protocols employing arterially inserted proteinaceous or polymeric multiloop devices are also described in Example IX.

One embodiment of the present invention in which rapid acting clearing agents are useful is in the delivery of Auger emitters, such as I-125, I-123, Er-165, Sb-119, Hg-197, Ru-97, Tl-201 and I-125 and Br-77, or nucleus-binding drugs to target cell nuclei. In these embodiments of the present invention, targeting moieties that localize to internalizing receptors on target cell surfaces are employed to deliver a targeting moiety-containing conjugate (i.e., a targeting moiety-anti-ligand conjugate in the preferred two-step protocol) to the target cell population. Such internalizing receptors include EGF receptors, transferrin receptors, HER2 receptors, IL-2 receptors, other interleukins and cluster differentiation receptors, somatostatin receptors, other peptide binding receptors and the like.

After the passage of a time period sufficient to achieve localization of the conjugate to target cells, but insufficient to induce internalization of such targeted conjugates by those cells through a receptor-mediated event, a rapidly acting clearing agent is administered. In a preferred two-step protocol, an active agent-containing ligand or anti-ligand conjugate, such as a biotin-Auger emitter or a biotin-nucleus acting drug, is administered as soon as the clearing agent has been given an opportunity to complex with circulating targeting moiety-containing conjugate, with the time lag between clearing agent and active agent administration being less than about 24 hours. In this manner, active agent is readily internalized through target cell receptor-mediated internalization. While circulating Auger emitters are thought to be non-toxic, the rapid, specific targeting afforded by the pretargeting protocols of the present invention increases the potential of shorter half-life Auger emitters, such as I-123, which is available and capable of stable binding.

In order to more effectively deliver a therapeutic or diagnostic dose of radiation to a target site, the radionuclide is preferably retained at the tumor cell surface. Loss of targeted radiation occurs as a consequence of metabolic degradation mediated by metabolically active target cell types, such as tumor or liver cells.

Preferable agents and protocols within the present invention are therefore characterized by prolonged residence of radionuclide at the target cell site to which the radionuclide has localized and improved radiation absorbed dose deposition at that target cell site, with decreased targeted radioactivity loss resulting from metabolism. Radionuclides that are particularly amenable to the practice of this aspect of the present invention are rhenium, iodine and like "non +3 charged" radiometals which exist in chemical forms that easily cross cell membranes and are not, therefore, inherently retained by cells. In contrast, radionuclides having a +3 charge, such as In-111, Y-90, Lu-177 and Ga-67, exhibit natural target cell retention as a result of their containment in high charge density chelates.

Evidence exists that streptavidin is resistant to metabolic degradation. Consequently, radionuclide bound directly or indirectly to streptavidin, rather than, for example, directly to the targeting moiety, are retained at target cell sites for extended periods of time. Streptavidin-associated radionuclides can be administered in pretargeting protocols intravenously, intraarterially or the like or injected directly into lesions.

U.S. Pat. No. 4,867,962 issued to Abrams describes an improved method for delivering active agent to target sites, which method employs active agent-targeting moiety conjugates. Briefly, the Abrams method contemplates administration to a recipient of two or more active agent-targeting moiety conjugates, wherein each conjugate includes a targeting moiety of a different antibody species. Each of the utilized antibody species is reactive with a different target site epitope (associated with the same or a different target site antigen), and the patterns of cross-reactivity for the antibody species are non-overlapping. The active agent component of each administered conjugate may be the same or different.

In this manner, the different antibodies (along with the agents attached thereto) accumulate additively at the desired target site, while only one or fewer than the total administered antibody species accumulate on each type of cross-reactive non-target tissue. A higher percentage of the administered agent therefore becomes localized in vivo at target sites compared to non-target tissues. For diagnostic agents, this methodology results in more clearly detected or imaged target sites against a comparatively lower (i.e., more diffuse background of non-target tissue accumulation. Lower accumulation of therapeutic agents at different non-target tissues permits larger doses of the associated active agents to be administered without incidence of undesirable non-target toxicity.

The present invention provides two-step and three-step pretargeting methods as set forth below.

The two-step approach involves:

administering to the recipient a first conjugate comprising a targeting moiety of a first antibody species having a first pattern of cross-reactivity and a member of a ligand-anti-ligand binding pair;

administering to the recipient one or more additional targeting conjugates, each such conjugate comprising a targeting moiety of a different antibody species from the species of the first conjugate and from each other and having a substantially non-overlapping pattern of cross-reactivity from each other and from the first pattern of cross-reactivity and the member of the ligand-anti-ligand pair bound to the first conjugate;

optionally administering to the recipient a clearing agent capable of directing the clearance of circulating conjugate from the recipient or optionally treating the recipient with a clearing device or an alternative clearing procedure to substantially remove circulating conjugate from the recipient; and administering to the recipient a second conjugate comprising an active agent and a ligand/anti-ligand binding pair member, wherein the second conjugate binding pair member is complementary to that of the first conjugate.

One alternative to the optional clearance step set forth above is simply to allow an amount of time to pass that is sufficient to permit the recipient's native clearance mechanisms to substantially remove circulating conjugate.

The three-step approach involves:

administering to the recipient a first conjugate comprising a targeting moiety of a first antibody species and having a first pattern of cross-reactivity and a ligand;

administering to the recipient one or more additional targeting conjugates, each such conjugate comprising a targeting moiety of a different antibody species from the species of the first conjugate and from each other and having a substantially non-overlapping pattern of cross-reactivity from each other and from the first pattern of cross-reactivity and the ligand bound to the first conjugate;

administering to the recipient an anti-ligand; and administering to the recipient a second conjugate comprising the ligand and an active agent, wherein second conjugate localization at the target site is enhanced as a result of prior localization of the first conjugate.

Alternatively, antibody-based or non-antibody-based targeting moieties may be employed to deliver a ligand or an anti-ligand to a target site bearing an unregulated antigen. Preferably, a natural binding agent for such an unregulated antigen is used for this purpose. For example, diseases such as hepatoma or myeloma are generally characterized by unregulated IL-6 receptors for which IL-6 acts as an autocrine or paracrine moiety with respect to rapid proliferation of these target cell types. For the treatment of such S ailments, IL-6 may therefore be employed as a targeting moiety in a pretargeting protocol of the present invention.

For example, IL-6 and streptavidin may be conjugated via chemical means or be formed as a recombinant molecule. The IL-6-streptavidin conjugate is administered to a recipient, and the IL-6 component of the conjugate directs the localization of the conjugate to IL-6 receptors. This localization will occur preferentially to sites bearing unregulated IL-6 receptors. After target site localization occurs, a clearing agent is optionally administered to substantially clear the recipient's circulation of IL-6-streptavidin conjugate. Suitable clearing agents for this purpose are, for example, IL-6 receptor-HSA-galactose; anti-IL-6-antibody-HSA-galactose or the like. After a time sufficient for substantial clearance of IL-6 from the recipient's circulation, active agent-biotin conjugate is administered and localizes to target sites via the IL-6-streptavidin conjugate.

In the practice of these aspects of the present invention, the target site accretion of active agent conjugate receptor (i.e., the ligand or anti-ligand conjugated to the first antibody species and additional targeting antibody species) is improved, because each antibody species recognizes a different epitope associated with the target site. This alternative epitope approach provides more potential target site binding points for the active agent conjugate receptor. Consequently, actual or effective target site saturation (via epitope saturation and/or steric hindrance) may be avoided; the target binding site barrier (binding of surface epitopes of the target site, which limits egress to internal target site epitopes) may be circumvented; and additive accumulation of active agent conjugate receptor may be accomplished. The practice of this aspect of the present invention provides a ligand- or anti-ligand-active agent conjugate with a target site that is densely populated with the anti-ligand or ligand antigen to which the active agent-containing conjugate may bind. Up to a point dictated primarily by steric factors, increased target site antigen density facilitates increased active agent accretion thereto.

The phrase "non-overlapping patterns of cross-reactivity" indicates that the non-target tissues bound by one antibody species differs substantially from the non-target tissues bound by another antibody species. The patterns of cross-reactivity must differ to the extent necessary to proportionately reduce the background for diagnostic applications and to reduce the toxicity to normal tissues for therapeutic applications. The less overlap in cross-reactivity to non-target tissues, the more useful an antibody pair (or larger set of antibodies) in the practice of these aspects of the present invention.

The patterns of cross-reactivity for monoclonal antibodies directed against a particular target site are analyzed to identify a set of two or more target-specific monoclonal antibodies with non-overlapping cross-reactivity for use in a diagnostic or therapeutic application. Antibodies may be screened by a variety of methods. The in vitro procedure employed to determine reactivity with target tissue and cross-reactivity with non-target tissue is immunohistochemical analysis. Tissues to which the antibody species binds are identified by exposing the tissue to the antibody; washing the tissue to remove any unbound antibody; and detecting the presence of bound antibody. Frozen tissue sections are preferred for use in these immunohistochemical methods, because tissue fixation may destroy epitopes and is associated with uncertainties in timing that may compromise antigen preservation. For antigens that are known to be preserved following fixation, such a technique may be effectively used in vitro histochemical procedures are known (e.g., Ceriani et al., *Cancer Research,* 47: 532–540, 1987 or Example I of U.S. Pat. No. 4,867,962).

In these multi-targeting moiety administering aspects of the present invention, the doses of each administered component will be determined by the attending physician in accordance with his or her experience, the particulars of the recipient's condition (the nature and location of the target site, including the antigens associated therewith, will impact antibody species selection and route of administration decisions) and the combination of antibody species to be employed (antibody performance varies with respect to antigen density and the affinity of the antibody for the antigen). It would be evident to one of ordinary skill in the art how to determine useful dosages of the components described above.

It is another object of the invention to provide further improvements of the afore-described pretargeting methods by reducing or eliminating the potential antigenicity of the pretargeting conjugate and/or the active agent containing conjugate.

In particular, this will be accomplished by modification of the ligand or anti-ligand contained in the pretargeting conjugate or active agent containing conjugate, or the targeting moiety contained in the pretargeting conjugate by the attachment of glycol moieties, preferably polyalkylene glycol moieties, and more preferably polyethylene glycol moieties, to one or more of the anti-ligand or targeting moiety.

Methods for the attachment of glycols, and particularly polyethylene glycols to desired compounds, e.g., proteins, are well known in the art. For example, WO 94/05332 describes means for attachment of glycol moieties to macromolecules including proteins and nucleic acids via glycosylation moieties, preferably using alkylene glycols having 1 to 20 carbon atoms. This is accomplished by activating a polyalkylene glycol, reacting the activated polyalkylene glycol with a diamino compound so as to couple the polyalkylene glycol to the diamino compound via one of its amino groups, oxidizing the macromolecule (e.g., a therapeutic protein) to activate at least one glycol group therein, and reacting the polyalkylene glycol coupled diamino compound with the oxidized glycosyl group, to provide a glycolated glycosylated macromolecule containing a glycol bonded to the macromolecule via glycosyl groups. The reference describes that this results in macromolecules have decreased immunogenic response but maintained biological activity. The described macromolecules include polypeptides, nucleic acids and lipids. Moreover, the reference describes that the glycol derivatized macromolecules maintain binding capacity.

U.S. Pat. No. 5,284,934 to Allen, Jr. similarly describes the preparation of carbohydrate-binding lectin derivatives for use as immune modulators or immune conjugates by attachment of polyethylene glycol to *Ricinius communis* agglutin I (PEG-RCAI) to a polymer by use of a coupling agent, e.g., 1,1-carbonyl-diimidazole. The resultant conjugate is disclosed to be substantially non-immunogenic. The patent further discloses other references which describe attachment of macromolecules, e.g., enzymes and hormones to polyethylene glycol, to produce conjugates for therapeutic use which are substantially non-immunogenic. These references are incorporated by reference in their entirety.

It is known that PEGylation may result in proteins and polypeptides having reduced immunogenicity and altered serum clearance properties. It is further known that PEG modified protectors are resistant to metabolic deactivation. The following references are representative of PEG modification of proteins. Wang et al., *Cancer Res.,* 53, 4588–4597 (1993), who describe PEG attachment to a chimeric toxin; Rosenberg et al., *J. Biol. Chem.,* 267 (32), 2289–2293 (1992), who describe PEG modification of asialofetuin; Somack et al., *Free Rad. Res. Comms.,* 12–13, 553–562 (1991), who describe PEG modification of superoxide dismutase; Malik et al., *Exp. Hematol.,* 20, 1028–1035 (1992) who describe PEG modification of macrophage colony stimulating factor (GM-CSF) to produce derivatives having conserved biological activity; and Tsutsumi et al., *Japan J. Cancer Res.,* 85, 9–12 (1994) who describe PEG modification of tumor necrosis factor to produce conjugates having improved anti-tumor activity. In some instances PEG modification of a protein has been disclosed to result in loss of biological activity. (See, e.g., Wang et al., Id.; Sumack et al, Id. and Tsutsumi et al., Id., in this regard). However, in most instances this can be obviated or alleviated by optimizing the amount of bound glycol residues, the particular means for their attachment, or by the use of protecting agents which protect active sites, e.g., binding sites, during PEGylation. Essentially, in the present invention, the particular ligand, anti-ligand, targeting moiety or active agent will be derivatized with one or more glycol residues, e.g., polyethylene glycol, and then assayed for activity. In the case of the ligand or anti-ligand or targeting moiety this will be determined in binding assays which assay the ability of the glycol derivatized moiety to bind the corresponding anti-ligand or ligand.

In the prototypical embodiment, the moiety to be derivatized with glycol residues will comprise streptavidin or avidin. However, glycol attachment, and more specifically polyethylene glycol attachment, should reduce the immunogenicity of other ligands and anti-ligands, as well as active agents and targeting moieties which are used n pretargeting protocols.

The subject embodiment will comprise particular benefit if the ligand, anti-ligand or active agent is of non-mammalian origin and is therefore likely to induce an immunogenic response. However, PEGylation may also be used to reduce or eliminate the potential immunogenicity of mammalian proteins or to alter their clearance properties. For example, the present invention embraces the attachment of polyethylene glycol moieties to the targeting moiety, which is typically of mammalian origin, e.g., an antibody, antibody fragment or derivative, e.g., single chain antibody, Fab, (Fab)$_2$, Fv, chimeric antibody, humanized antibody, bispecific antibody, which targeting moiety is contained in the pretargeted conjugate. Such derivatization should eliminate or alleviate the possibility of an adverse immunogenic response, i.e., HAMA response, to the targeting moiety contained in the pretargeted conjugate. While this is not a significant concern in diagnostic applications, such an antibody response may potentially be problematic during therapeutic pretargeting methods since it may prevent the conjugate from being delivered efficiently to the desired target site.

As noted, there are many known procedures for the covalent attachment of glycol moieties, e.g., polyalkylene glycol moieties, to desired molecules. Such techniques are described in the previously discussed references pertaining to polyalkylene derivatization of macromolecules, e.g., proteins, which are incorporated by reference herein. Additionally, such techniques are described in Delgado et al., *Biotech Appl. Biochem.*, 252 (11), 3578–3581 (1977). Such procedures typically exploit acylation or alkylation reactions involving amino groups, or alternatively attach such moieties to carboxyl residues or to activated (oxidized) glycosyl groups (see, WO 94/05 332).

The selection of the particular means of attachment will depend on the available functional groups contained on the particular ligand, anti-ligand, targeting moiety or active agent which is to be modified by the addition of glycol residues. If suitable functional groups are not available for attachment, they may be introduced on the particular compound to be modified by reaction with compounds containing the desired functional groups, e.g., amino groups, carboxyl groups or glycosyl groups. Means for introduction of functional groups into macromolecules, e.g., proteins and polypeptides are well within the purview of the ordinarily skilled artisan.

A prototypical example of this aspect of the invention relates to conjugation of polyethylene glycol moieties to either avidin or streptavidin. Streptavidin is a 60 Kd tetrameric protein which binds 4 moles of biotin per mole of protein. Preferably, attachment of polyethylene glycol moieties should not substantially affect the ability of streptavidin or avidin to bind biotin. This will depend upon factors including the particular means and site of polyethylene glycol attachment, and the number of attached polyethylene glycol residues.

As described in detail in the experimental examples relating to this embodiment of the invention, reaction of polyethylene glycol moieties with streptavidin produced streptavidin conjugates containing polyethylene glycol moieties. However some of such conjugates exhibited substantially reduced biotin binding ability in an HABA assay which measures the displacement of 2-(4'-hydroxyazobenzene)benzoic acid (HABA) from streptavidin by biotin. However, such problems were substantially alleviated by effectively blocking the biotin binding sites prior to the attachment of polyethylene glycol residues.

Suitable blocking agents include, in particular, the low affinity biotin analogs identified above, antibodies to biotin binding sites, etc. The only prerequisite is that such moieties be capable of removal without adverse effects to the protein and that such attached moieties not adversely affect PEGlyation.

This will preferably be effected by attachment to the particular protein, e.g., streptavidin or avidin, of moieties which reversibly bind to biotin affinity sites, e.g., low affinity biotin analogs.

When targeting moieties, ligands or anti-ligands active agents are attached to polyethylene glycol residues it may also be necessary to protect the active site, e.g., binding site, prior to attachment of polyethylene glycol residues, or to vary the number of polyethylene glycol residues.

The present invention also provides methods of inducing an inflammatory response by increasing superantigen active agent localization at a target cell site within a mammalian recipient, including the following:

administering to the recipient a first conjugate comprising a targeting moiety which is capable of localizing to the target cell site and avidin or streptavidin; and subsequently administering to the recipient a second conjugate comprising a superantigen active agent and biotin. Preferably, the second conjugate is removed from the recipient primarily via renal excretion; and the superantigen will localize to the target cell site and thereby induce an inflammatory response of the recipient's immune system.

Optionally, these methods of the present invention include the step of administering to the recipient a clearing agent capable of directing circulating first conjugate to hepatocyte receptors, thereby decreasing the amount of circulating first conjugate prior to administering the second conjugate. Alternatively, other clearing mechanisms or agents may be used.

Native superantigen may be excreted primarily via the renal pathway rapidly enough so that the inflammatory response caused by the superantigen is not substantially systemic in nature. If the native form of the superantigen is not excreted primarily through the kidneys or is not excreted rapidly enough, the superantigen or a conjugate containing the superantigen is chemically modified to facilitate renal excretion thereof. Preferably, the superantigen may be derivatized with one or more non-hepatocyte-receptor-recognizing carbohydrate moieties or may be succinylated.

Alternatively, the superantigen may be directed to hepatic excretion by derivatization with one or more hepatocyte receptor-recognizing carbohydrates. A preferred superantigen for use in the practice of the present invention is staphylococcal enterotoxin A.

Also provided by the present invention are methods of increasing active agent localization at a target cell site within a mammalian recipient, which include:

administering to the recipient a first conjugate comprising a targeting moiety capable of localizing to the target cell site; avidin or streptavidin; and a superantigen capable of inducing an inflammatory response at the target cell site without antigen presentation; and subsequently administering to the recipient a second conjugate comprising an active agent and biotin, wherein greater localization of second conjugate at the target cell site or a more homogenous distribution of the first or second conjugates at the target cell site is facilitated by the inflammatory response induces by the superantigen. Again, an optional clearing step may be employed as described above. This method amy be employed in conjunction with appropriate active agents, such as cytokines, therapeutic or diagnostic radionuclides, toxin or the like.

Alternatively, a targeting moiety-superantigen conjugate may be employed as a preliminary procedure in a pretargeting protocol. Such a pretargeting protocol includes:

administering to a recipient a targeting moiety-superantigen conjugate wherein the conjugate localizes to a first epitope associated with the target cell site and the superantigen induces an inflammatory response at the target cell site;

administering to the recipient a first conjugate comprising a targeting moiety which is capable of localizing to a second epitope associated with the target cell site (wherein the first epitope and the second epitope are the same or different) and avidin or streptavidin;

subsequently administering to the recipient a second conjugate comprising an active agent and biotin, wherein the second conjugate is removed from the recipient primarily via renal excretion.

Any of the clearance strategies set forth above may be employed in the practice of this aspect of the claimed invention to clear targeting moiety-superantigen, targeting moiety-avidin or -streptavidin or both. In this embodiment of the present invention, the superantigen includes a localized inflammatory response at target cell sites, thereby facilitating enhanced targeting of the first and second conjugates thereto. Also, this aspect of the present invention may be employed in conjunction with the various active agents discussed herein.

Superantigens refer to highly immunogenic molecules that are capable of inducing an immune response in a recipient without the necessity for internalization and antigen presentation. The prototypical superantigen discussed herein is staphyloccal enterotoxin A. Superantigens are known to potently stimulate the activity of T lymphoyles of different species. This activation may result in the expression of waves of cytokines, e.g., TNR, IL-1, IL-6 and IFN-gamma (Miethke et al., Immunobiol., 189 (3–4), 270–284 (1993)). Also, in some cases superantigen stimulate the proliferation of B cells harboring the virus which expresses the superantigen. (See, Irwin et al., *J. Leukocyte Biol.,* 54(5), 494–503 (1993)).

Highly immunogenic molecules that are capable of inducing an immune response in a recipient without internaliza-tion and antigen presentation (superantigens) are useful in the practice of the present invention. Exemplary superantigens are bacterial and mycoplasma exoproteins, such as the staphylococcal and streptococcal exotoxins, and an exoprotein produced by *Mycoplasma arthritidis*, viral antigens such as the mammary tumor virus encoded Mla antigens and the like. Other superantigens are also well known in the art. See, e.g., the following review articles pertaining to superantigens, which are incorporated by reference in their entirety: Irwin et al., *J. Leukocvte Biol.,* 54 (5), 495–503 (1993); Zumla, *Clin. Infect. Dis.,* 15 (2), 313–320 (1992); Kotb, *Current Opin. Infect. Dis.,* 5 (3), 364–374 (1992); Johnson et al., *Proc. Soc. Biol. Med.,* 198 (3), 765–771 (1991); Webb et al., *Current Opin. Immunol.,* 6 (3), 467–475 (1991); Fleischer, *Berhrin, Institute Metteilunaen,* 94, 104–112; (1994); Lafon, *Medecine-Sciences,* 10 (1), 78–82 (1994); Uchiyama et al., *Microbiol. Immunol.,* 38 (4), 245–256 (1994); Scherer et al., *Annual Rev. Cell Biol.,* 9, 101–128 (1993); Misfeldt, *Eus-Riv Immun. Immunofarmacol.;* 13 (2), 150–154 (1993); Licastro et al., *Int. J. Biochem.,* 25 (6), 845–852 (1993). A preferred superantigen for the practice of the present invention is staphylococcal enterotoxin A. See, for example, Dohlsten et al., *Proc. Natl. Acad. Sci. USA,* 88, 9287–9291 (1991), incorporated by reference.

Preferred superantigens of the present invention are those that are structured or that are designed to be structured to be excreted primarily via the renal route or are otherwise rapidly cleared to facilitate a target cell site localized inflammatory response. Native superantigens characterized by non-terminal carbohydrate residues or the like may be employed in the present invention. Superantigens that are chemically modified to incorporate the aforementioned groups may also be employed in the practice of the present invention. Alternatively, other chemical modifications, such as succinylation, polymer-derivatization, DTPA-derivatization as set forth herein for toxin-containing active agents may also be used with respect to superantigens to enhance the renal excretion thereof.

The chemical modification of a superantigen to incorporate one or more carbohydrate residues may be conducted in a manner analogous to that described herein for derivatization of human serum albumin with galactose.

Such molecules induce an inflammatory response in a recipient that may serve to (1) exert cytotoxicity upon target cells; (2) increase the localization of active agent to a target cell site (wherein the active agent is either the superantigen itself or one of the other active agents discussed herein); or enhance the homogeneity of the distribution of active agent at a target cell site; or a combination thereof.

Superantigens, such as staphylococcal enterotoxin A may be conjugated to biotin in a manner analogous to the conjugation of toxins or other proteinaceous moieties thereto, as discussed herein. For example, the terminal carboxyl group of biotin is converted to an active ester, and the active ester is reacted with an amine group of a lysine residue of the superantigen. Biotin may also be conjugated to the carboxy terminus of the superantigen in a manner designed to favor mono-biotinylation by reverse proteolysis as described by Aofford et al, *Meth. Enzymol.,* 184: 160–162., (1988). Superantigens may also be conjugated to avidin or streptavidin in a manner analogous to the conjugation of toxins or other proteinaceous moieties thereto, as discussed herein. Conjugation to streptavidin may be favored for the active agent localization enhancement embodiment of this aspect of the present invention.

For example, the superantigen-containing conjugates may be modified by derivatization with a biodistribution directing molecule such as the following: hydrophilic polymers, such as 10 kD dextran, larger dextran molecules (having molecular weights ranging from about 20 to about 70 kD), polyglutamates (having molecular weights ranging from about 5 to about 50 kD), succinylated polylysines (having molecular weights ranging from about 5 to about 50 kD) as well as succinylated and other large modified forms of poly-lysine and defined oligosaccharides, i.e., oligosaccharides produced synthetically such that the structure is chemically defined and of sufficient size to substantially overcome liver and other organ uptake which facilitates renal excretion via glomular filtration. Polymers, such as those described above, are removed from recipients by renal excretion and, therefore, polymeric derivatization facilitates renal excretion of polymer-containing conjugate.

Biotin-polymer-staphylococcal enterotoxin A conjugates may be formed using commercially available biotinylated, lysine-derivatized dextran polymer (e.g., biotin-dextran, lysine fixable available from Sigma Chemical Co., St. Louis, Mo.). The lysine derivatized-biotin is conjugated via the reaction of a lysine epsilon-amino group, for example, with an activated ester of the superantigen. Active esters as are employed in the art may be used for this purpose (e.g., N-hydroxysuccinimide; phenols substituted with strong electron withdrawing groups such as nitro and fluoro groups; and the like). Alternatively, biotin-polymer-staphylococcal enterotoxin A conjugates, for example, may be formed using commercially available biotinylated, lysine-derivatized dextran polymer that is activated by reaction of a lysine residue thereof with the bifunctional reagent, succinimidyl-4-(N-maleimido-methyl)cyclohexane-l-carboxylate (SMCC), under conditions analogous to the biotinylation set forth above (e.g., pH, molar ratio and like conditions). The SMCC-derivatized dextran polymer now contains the reactive maleimide functional group available for conjugation with a free thio group of the superantigen, for example.

Derivatization alternatives include (DTPA)N where n ranges from about 1 to about 2. DTPA, diethylene triamine penta-acetic acid, e.g., DTPA cyclic anhydride, may be linked by an amide bond via a native carboxylate group or a synthetically added carboxylate group of a superantigen.

Another object of the present invention is to provide novel methods and compositions for the treatment of thrombolytic disorders. Thromboembolic diseases are a major cause of death and disability in Western society. They comprise as main categories: coronary artery thrombosis leading to acute myocardial infarction; cerebral artery thrombosis resulting in stroke; and deep vein thrombosis predisposing to pulmonary embolism. Although the basic pathology of coronary artery disease consists of atheromatous degeneration of the blood vessel wall, the clinical events of myocardial infarction are in the majority of cases triggered by a thrombotic event. (See, Collen et al, *J. Pharmacol. Exp. Therapeutics,* 231(1), 146–152 (1984)).

Because of the critical role of thrombosis in human disease, pharmacological thrombolysis, i.e., in vivo thrombosis dissolution by the administration of substances which activate the endogenous fibrinolytic system in blood, has been in existence for over 40 years. Substances used for the treatment of thrombolytic disorders include, for example, urokinase, streptokinase, tissue plasminogen activator, as well as derivatives, truncated, and hybrid forms thereof. See, Holvoct et al., *Circulation,* 87(3), 1007–1016 (1993); Holvoct et al., *Blood,* 81(3), 696–703 (1993); Bos et al., *Biotherapy,* 5(3), 187–199 (1992); Verstraete, *Cardiovas. Drugs. Ther.,* 6(2), 111–124 (1992); Neblock et al., *Bioconjugate Chem.,* 3(2), 126–131 (1992); Haber et al., *Thrombolysis: Basic Contrib. and Clin. Prog.*, XVII, 357 pp. (1992); DeBono et al., *Thromb. Rev.,* 61, 537–545 (1991); Runge et al., *Proc. Natl. Acad. Sci. USA,* 88(22), 10337–10341 (1971); Collen et al., *Circulation,* 82(5), 1744–1753 (1990); Haber et al., *Jpn. Circ. J.,* 54(4), 345–353 (1990); Dewerchin et al., *Fibrinolysis,* 4(1), 11–18 (1990).

Some of those thrombolytic agents have proved to be very useful in treatment of thrombolytic disorders. For example, tissue plasminogen activator (t-PA) is clinically used for the treatment of heart attack victims. t-PA exhibits several advantages over other thrombolytics. Because it is of human origin, it is less subject to adverse immune reactions. This is in contrast to streptokinase which, while it efficiently dissolves clots, is of bacterial origin and therefore may mediate an immune reaction. Also, t-PA is more specific in its action than other thrombolytic therapeutic agents, e.g., urokinase and streptokinase. This is because t-PA has higher affinity for fibrin compared with urokinase-type plasminogen activators, e.g., streptokinase and urokinase (Collen, *Nature,* 301, 214–221 (1983)).

However, while the treatment of thrombolytic disorders, e.g., heart attacks, by the administration of clot dissolving agents has known human clinical efficacy, such treatments are subject to some adverse side-effects. In particular, such compounds are associated with systemic activation of plasminogen which can result in the indiscriminate digestion of coagulation proteins and therefore significantly increase the risk of hemorrhage during treatment. In fact, the administration of available clot dissolving agents, even t-PA, is associated with adverse side effects, e.g., bleeding disorders.

This is believed to be at least in part attributable to the fact that not all of the administered clot dissolving agent, e.g., t-PA, is delivered to the desired site, i.e., a fibrin containing blood clot. Therefore, indiscriminate activation of both circulating and fibrin-bound plasminogen may result.

Another problem associated with some thrombolytics is that they may mediate an immune reaction which neutralizes the activity of the administered therapeutic protein. As discussed, this is a particular concern for streptokinase given its bacterial origin. However, it is a potential concern even for proteins of human origin, e.g., t-PA. In this regard, many functional derivatives of t-PA and urokinase, and hybrid forms thereof, are known and are being developed. While such derivatives afford some intrinsic advantages, e.g., enhanced clot dissolving activity, affinity and/or stability, the fact that they are mutant proteins increases the likelihood that they may produce an adverse immune response upon administration, particularly if the particular derivative is to be used for a prolonged time period or repeated usage.

Also, such clot dissolving agents may stay in the immune circulation after they have mediated the desired therapeutic effect, i.e., dissolved a blood clot. This also enhances the potential that such administration may cause indiscriminate digestion of coagulation proteins and therefore hemorrhage during treatment.

The targeting of thrombolytic agents to thrombi has also been disclosed in the literature. Known targeting agents include, e.g., antibodies, single chain antibodies, and bispecific antibodies, which bind fibrin, cross-linked fibrin, damaged endothelial cells, and recently annexin-V (Tait et al., *Thrombosis Rev.,* 75(5), 491–501 (1994)).

The present invention alleviates problems associated with previous thrombolytic therapies, e.g., the treatment of heart attacks, stroke, and restenosis comprising the therapeutic administration of thrombolytic agents. This is accomplished by the administration of conjugates which are more effectively delivered to a target site, i.e., a blood clot, and optionally by the further administration of clearing agents before, concurrent or after administration of thrombolytic agents which provide for the rapid clearance thereof. In particular, this is accomplished by a pretargeting therapeutic state, which comprises the administration of a conjugate to a subject in need of thrombolytic treatment which provides for effective targeting of a subsequently administered ligand or anti-ligand thrombolytic agent conjugate to the desired site, i.e., a blood clot.

The conjugates used for targeting the thrombolytic agent conjugate will preferably comprise a targeting protein which binds to the target site, i.e., a blood clot which is directly or indirectly attained to a ligand or anti-ligand. Examples of targeting moieties include those identified supra, e.g., antibodies to fibrin, x-linked fibrin and the annexin proteins, e.g., annexin-V. Other suitable monoclonal antibodies are described by Oster et al., *Proc. Natl. Acad. Sci.*, 82, 3465–3468 (1985); Peters et al., *British J. Med.*, 293, 1525–1527 (1986); Sum et al., *J. Nucl. Med.*, 27, 1315–1320 (1986); and Delabrier et al., *Proc. Natl. Acad. Sci.*, 86, 1036–1040 (1989). Examples of suitable ligands and anti-ligands include biotin, streptavidin, avidin, S-peptide, S-protein, head activator peptide (HA peptide), as well as any of the other previously identified ligands and anti-ligands. The only prerequisite is that the particular ligand or anti-ligand be substantially non-toxic and bind to its binding counterpart with sufficient affinity to provide for effective binding of a second conjugate containing the therapeutic agent, i.e., a thrombolytic agent such as t-PA, urokinase, or streptokinase, or derivatives or hybrid forms thereof.

Annexins are the prototypical targeting moiety for directing a thrombolytic agent to the desired target site, i.e., a blood clot(s). Also, annexins may be used to direct other therapeutic or diagnostic agents to sites containing activated platelets. In the preferred embodiment, the targeting moiety will comprise Annexin-V, which has a $K_d$ of $10^{-9}$M for activated platelets (Thlagarajan et al., *J. Biol. Chem.*, 265 (29), 17420–17423 (1990)). Other examples of suitable targeting proteins include antibodies and other moieties which bind activated platelets.

Annexins are generally (with the most notable exception being annexin II) single chain, non-glycosylated proteins of approximately 33–72 kilodalton molecular weight. Annexins possess a number of biological activities associated with calcium ion-mediated binding.

Investigations have shown that annexins bind with high affinity to anionic membrane lipids in the presence of millimolar concentrations of calcium. In the presence of calcium, these proteins have an especially high affinity for negatively charged phospholipids, such as phosphatidylserine, phosphatidylglycerol, phosphatidic acid, or phosphatidylinositol. See, for example, Funakoshi et al., *Biochem.*, 26: 5572–78, 1987; and Tait et al., *Biochem.*, 27: 6268–76, 1988. Such negatively charged phospholipids are associated with vascular thrombi (e.g., are located on the surface of activated human platelets).

Annexins exert anti-coagulatory effects. Coagulation inhibition is mediated by the binding of annexins to negatively charged surface phospholipids (e.g., present on the surface of activated platelets). This binding is believed to block the activation of clotting factors by such negatively charged surface phospholipids. Annexins localize to target sites bearing anionic phospholipids rapidly, i.e., in a matter of approximately 5 to 30 minutes depending on circulating levels thereof, but remain circulating in the serum for a somewhat longer time period (circulating half-life<39 minutes).

Because of these properties, annexins or annexins conjugated to diagnostic or therapeutic agents may be employed in protocols for the diagnosis or treatment of vascular thrombi associated with a number of indications, such as DVT (deep vein thrombosis), PE (pulmonary embolism), myocardial infarction, atrial fibrillation, problems with prosthetic cardiovascular materials, stroke and the like.

An example of a preferred annexin useful in the practice of the present invention is Annexin V, which was isolated by Bohn in 1979 from human placenta, a rich source of annexins, and termed Placenta Protein 4 (PP4). Annexin V has been expressed in *E. coil*. Also, a full length CDNA clone of annexin V has been obtained and subcloned in expression vectors, thereby facilitating the production of fusion proteins containing annexin V. Annexin V consists of four domains (four tandem, imperfect repeats of about 75 amino acid residues, Funakoshi et al., *Biochem.*, 26: 8087–92, 1987), wherein each domain is made up of 5 alpha helices. From the side, the annexin V molecule appears crown-like with at least four calcium binding sites on its convex surface, through which annexin-phospholipid interactions are mediated. Other annexin molecules are also useful in the practice of the present invention, and the discussions relating to annexin V herein apply generally to annexin molecules.

Because annexin V has a plurality of calcium binding sites, and because annexin V binding to negatively charged phospholipids is mediated by calcium, an engineered molecule consisting of one or more individual annexin V domains may be employed in pretargeting imaging or therapeutic protocols. Also, the annexin molecule may be partitioned at a position or positions different from the domain boundaries to provide an engineered molecule capable of calcium-mediated binding of anionic phospholipids. Also, annexin V may be altered at one or more amino acid residues, so long as the affinity of annexin V for anionic phospholipids is not significantly impaired. The degree of annexin binding to phospholipids may be quantified by fluorescence quenching as described by Tait et al., *J. Biol. Chem.*, 264: 7944–49, 1989.

Among annexins, annexin V has the strongest binding affinity $K_d<10^{-10}$ M) for phospholipid vesicles containing 80% phosphatidylcholine and 20% phosphatidylserine under conditions comparable to plasma and extracellular fluid (1.2 mM ionized calcium, 0.15 M ionic strength). This binding is reversible and calcium dependent.

In order to decrease binding to non-target sites and to enhance clearance, the targeting moiety may be derivatized to facilitate clearance. For example, annexins may be derivatized with hexose or hexose-based moieties to provide for clearance. Annexins, e.g., may be derivatized to incorporate one or more hexoses (six carbon sugar moieties recognized by Ashwell receptors or other liver receptors, such as the mannose/N-acetylglucosamine receptor, which are associated with endothelial cells and/or Kupffer cells of the liver, or by the mannose 6-phosphate receptor. Exemplary of such hexoses and hexose-based moieties are galactose, mannose, mannose 6-phosphate, N-acetylglucosamine, pentamannosyl phosphate, and the like. Other moieties recognized by Ashwell receptors, including glucose, N-galactosamine, N-acetylgalactosamine, thioglycosides of galactose and, generally, D-galactosides and glucosides or the like, may also be used in the practice of the present invention. Based on the description herein, one skilled in the art can design clearing agents to provide for clearance of either the first or second conjugate.

Galactose is the prototypical hexose employed for the purposes of this description. Galactose thioglycoside conjugation to a protein is preferably accomplished in accordance with the teachings of Lee et al., "2-Imino-2-methoxyethyl 1-Thioglycosides: New reagents for Attaching Sugars to Proteins," *Biochemistry,* 15(18): 3956, 1976. Another useful galactose thioglycoside conjugation method is set forth in Drantz et al., "Attachment of Thioglycosides to Proteins: Enhancement of Liver Membrane Binding," *Biochemistry,* 15(18): 3963, 1976.

If annexin is used for pretargeted imaging methods, including use of a radioactive chelate, hexose conjugation to the annexin via chemical methods can occur either prior to (post-formed approach) or following (pre-formed approach) complexation of the chelate with the radionuclide. Hexose chemical conjugation is preferably conducted prior to chelate conjugation, however.

The number of galactose residues on the product conjugates will range from 1 to the maximum number of galactoses that do not significantly diminish the binding affinity of annexin to its target. For example, galactose derivatization that preserves at least 20% of native annexin binding activity is preferred, with the preservation of at least 50% of native annexin binding activity more preferred. The theoretically possible maximum number of galactose residues located on the annexin molecule is 22 (the number of lysine residues within the annexin structure). An exemplary number of galactose residues on radiolabeled annexin-galactose conjugates of the present invention ranges between 1 and about 5.

Hexose clusters are preferably employed in the practice of the present invention. Factors to be considered and saved include the i) number of galactose in a cluster ii) distance between galactose cluster and the annexin conjugate component. Galactose clusters are the prototypical hexose clusters employed for the purposes of this description. In this regard, the literature suggests that galactose receptors on the surface of human hepatocytes are grouped as heterotrimers and perhaps, bis-heterotrimers optionally each galactose cluster should contain at least three galactose residues. Also, the galactose receptors in each trimer are separated by distances of 15, 22 and 25 angstroms. Hence, preferably the galactoses in a cluster will be separated by flexible linkers allowing for the separation of at least 25 angstroms. The distance between the annexin and the galactose cluster should be sufficient to obviate any steric effects upon annexin binding to target attributable to size or the orientation of the galactose cluster. This distance will preferably be greater than about 10 angstroms. The targeting moiety will preferably be attached to biotin or an analog thereof.

Subsequent to the administration of the pretargeting agent, a second conjugate will be administered which contains a diagnostic or thrombolytic agent, e.g., t-PA, urokinase, streptokinase or a mutant or derivative or hybrid form thereof which is directly or indirectly attached to a ligand or anti-ligand which binds the ligand or anti-ligand contained in the pretargeting agent. For example, if the pretargeting agent contains biotin, then the anti-ligand will be avidin, streptavidin or another biotin binding protein. Thus, suitable second conjugates used in this embodiment of the invention include, e.g., t-PA-avidin; t-PA-streptavidin; urokinase-avidin; urokinase-streptavidin; streptokinase-avidin; and streptokinase-streptavidin.

The administration of the pretargeting conjugate prior to thrombolytic conjugate administration should substantially alleviate the problems associated with non-specific binding of the thrombolytic agent, and therefore alleviate or prevent adverse, side effects, e.g., bleeding reactions. Moreover, the administration of a pretargeting conjugate which targets thrombi sites should also provide a highly effective means of targeting diagnostic agents, e.g., imaging agents to thrombi, in particular radionuclides.

As stated, the present invention further embraces the administration of a clearing agent. Such clearing agents include, e.g., any of the clearing agents identified supra, directly or indirectly attached to a ligand or anti-ligand which binds the ligand or anti-ligand contained in the targeting moiety conjugate. For example, if the thrombolytic conjugate comprises urokinase-streptavidin, effective clearing agents include, e.g., biotinylated proteins; biotinylated galactosylated proteins, as well as small molecule clearing agents which contain one or more biotin residues and hexose residues, e.g., galactose resides, and provide for specific clearance via heptocyte receptors.

The synthesis of the pretargeting conjugate and thrombolytic agent conjugates described supra may be effected by one of ordinary skill using well known and available heterobifunctional crosslinking agents. The dosage of the pretargeting agent, thrombolytic agent conjugate and clearing agent will comprise amounts which provides for effective lysis of clot(s) without adverse side effects, e.g., bleeding, may be easily determined by one skilled in the art. It is expected that efficacious dosage of the thrombolytic agent will be approximately the same or reduced in relation to known effective dosages of thrombolytic agents. Less of the thrombolytic agent may be required for efficacy because it is expected that the present invention will provide for better delivery of the thrombolytic agent to the desired site, i.e., blood clot.

With respect to the clearing agent, the preferred amount thereof will comprise a dosage which provides for effective clearance of the non-specifically bound targeting agent conjugate from the circulation.

Yet another object of the present invention is to provide novel methods of gene therapy which alleviate problems associated with conventional methods, i.e., the inability to direct nucleic acid sequences to desired cells. In particular, such improved methods will include the administration of a first pretargeting conjugate containing a ligand or anti-ligand bound to a targeting moiety (e.g., antibody or antibody fragment) such as described supra, and the concurrent or subsequent administration of a nucleic acid sequence which is directly or indirectly associated with a ligand or anti-ligand which binds to the ligand or anti-ligand contained in the pretargeting conjugate, and which conjugate binds to an antigen expressed on the cells which are to be treated.

Essentially gene therapy comprises the delivery and stable insertion of a desired nucleic acid sequence, e.g., contained on a plasmid, into target cells, wherein said nucleic acid sequence is stably maintained therein and confers some therapeutic benefit. Examples of nucleic acid sequences having application in gene therapy methods include sequences which encode therapeutic enzymes, drugs, cytokines, as well as any of the previously identified therapeutic proteins and polypeptides. Other nucleic acid sequences which have application in gene therapy include nucleic acid sequences which insert so as to activate or inactivate or modulate expression of a gene involved in a particular disease condition. For example, gene therapy methods have application in correcting gene defects, e.g., inherited mutations in a particular gene which is associated with a particular disease condition.

Gene therapy methods are particularly promising for the treatment of cancer. Such methods, for example, comprise the delivery of nucleic acid sequences which activate the host immune system to recognize antigens expressed on the cancer cells as foreign, and thereby activate the immune system to attack the tumor. Examples of such nucleic acid sequences include genes which encode Class 1 transplantation antigens. Nucleic acid sequences which encode cytokines, e.g., interleukins such as IL-1, IL-2, interferons, tumor necrosis factor, are also promising candidates for treatment of cancer by gene therapy. Additionally, the delivery of nucleic acid sequences which are cytotoxic to the cancer cell, e.g., anti-tumor agents, cytotoxins, or which disrupt an essential cell function show promise in such gene therapies.

However, while gene therapy is a promising tool for the treatment of cancer, it suffers from one serious disadvantage. In particular, conventional gene therapy methods typically require direct injection into the cells which are to be treated. In the case of cancer treatment, this entails the direct injection of the therapeutic nucleic acid sequence, for example, a plasmid, into surface cancer lesions.

This is disadvantageous because it limits the potential efficacy of such gene therapies to surface cancers. Accordingly, a method of gene therapy which enables nucleic acid sequences, e.g., plasmids, to be targeted and introduced into cancer cells by systemic injection would be highly beneficial since it would enable gene therapy to be useful for treatment of a variety of different cancers.

Toward this end, the present inventors have developed a method whereby desired nucleic acid sequences, e.g., which are contained on a plasmid may be effectively targeted to cancer cells by systemic injection. In particular, this will be effected by:

(i) a pretargeting step comprising administering a ligand or anti-ligand bound to a targeting moiety specific to an antigen expressed on the cancer cells which are to be targeted; and (ii) administration of an active agent which comprises a nucleic acid sequence which upon delivery and stable insertion in said cancer cells imparts a therapeutic effect, and wherein said nucleic acid sequence is "associated" with a ligand or anti-ligand which binds the ligand or anti-ligand contained in the pretargeted conjugate.

This "association" may comprise the indirect or direct attachment of the nucleic acid sequence to the ligand or anti-ligand, or it may comprise an indirect association whereby the nucleic acid sequence is encapsulated in a delivery vehicle, e.g., a liposome or virus particle which is attached to the ligand or anti-ligand. In the preferred embodiment, the nucleic acid sequence, e.g., plasmid, which is to be targeted to the cancer cells will be encapsulated in a liposome which is in turn attached to the particular ligand or anti-ligand and therefore specifically binds the pretargeted conjugate.

Methods for encapsulation of nucleic acid sequences into liposomes are well known in the art. Such methods originated in the early 1980's when Papahadjopoulos et al. taught the encapsulation of biologically active materials such as nucleic acids and proteins in liposomes and the use thereof for delivery of such biologically active materials into cells. See, e.g., U.S. Pat. No. 4,241,046 and U.S. Pat. No. 4,235,871 by Papahadjopoulus et al. Also, Szoka, Jr. et al., U.S. Pat. No. 4,394,448, teach insertion of DNA or fragments into living cells by encapsulating the DNA or fragment in a liposome and bringing the liposome in contact with cells such that insertion of the DNA or fragment occurs. Such methods have also recently been improved in order to enhance targeting efficiency to desired cells and/or to acids into cells.

For example, it is known to conjugate liposomes to ligands which selectively bind to targeted cells, thereby enhancing efficiency of delivery to desired cells. Relevant patents which disclose the conjugation of liposomes to cell targeting moieties, in particular antibodies, include U.S. Pat. No. 5,210,040 by Touet et al., U.S. Pat. No. 4,957,735 by Huang, Leaf, U.S. Pat. No. 4,925,661 by Huang, Leaf, U.S. Pat. No. 4,806,466 by Papahadjopoulos et al., U.S. Pat. No. 4,762,915 by Kung et al., U.S. Pat. No. 4,708,933 by Huang et al., U.S. Pat. No. 4,483,921 by Cole, Francis X., U.S. Pat. No. 4,480,041 by Myles et al. and U.S. Pat. No. 4,429,008 by Martin et al.

It is also known to produce pH sensitive liposomes which provide for enhanced delivery of targeted nucleic acids into cells. For example, U.S. Pat. No. 4,789,633 by Leaf Huang et al., and Huang et al., Proc. Nat'l. Acad. Sci., USA 87,7851 (1987) disclose pH sensitive DNA containing liposomes which fuse with cell membranes at pH's below 7 and thereby facilitate introduction of the desired DNA.

Another method for facilitating in vivo delivery of DNA containing liposomes involves the administration of cation containing liposomes. For example, U.S. Pat. No. 5,227,170 by Sullivan teaches encapsulation of oligonucleotides in liposomes which contain a divalent cation solution containing the desired oligonucleotides and having an osmolarity less than that of the internal aqueous phase. Also, Felgner et al., Proc. Nat'l. Acad. Sci., USA, 84,7413 (1987) teach cationic liposome complexes. However, due to their cationic character, the liposomes are subject to serum protein binding which may lead to inactivation of the olitherein. Also, contained therein. Also, the liposome DNA complexes may expose the oligonucleotides to nucleases, which may result in degradation of the desired oligonucleotide prior to its insertion in desired cells.

A recent patent by Huang, Karl J., U.S. Pat. No. 5,026,552 teaches a method for selectively delivering liposome encapsulated substances (e.g., polynucleotides) into the parenchymal or non-parenchymal cells of the liver which exploited the two known pathways for liposome uptake by the liver, specifically a saturable pathway involving phagocytosis and mediated by Kupffer cells, and a non-saturable pathway involving pinocytosis and mediated by parenchymal cells. The method comprises administering carrier liposomes having a diameter of less than 200 nm and a half-life in the circulation of at least 5 hours. Also, osmotically dependent liposomes are known in the literature, e.g., as disclosed by Weiner et al., U.S. Pat. No. 5,049,392.

Methods for optimizing the size of liposomes are also known. For example, U.S. Pat. No. 4,532,089 by MacDonald, Robert C. teaches a method for preparing giant size liposomes. Also, U.S. Pat. No. 4,529,561 by Hunt et al. teaches a method for preparing liposomes in desired size ranges. Further, Hostetler et al., U.S. Pat. No. 5,223,263 teach liponucleotide containing liposomes and the use thereof for delivery of the liponucleotides to desired cells. Thus, based on the above, it is clear that many methods for delivery of nucleic acids into cells are known in the art, as are methods which rely on liposomally mediated introduction of nucleic acids.

Moreover, the administration of liposome encapsulated nucleic acid sequences has also been reported to be efficacious for the treatment of melanoma, a surface cancer. For example, it was reported in a recent *Bioworld Today*, Vol. 4, No. 233, 1 and 5, that a cDNA encoding a Class 1 transplantation antigen HLA-B7, when inserted into a modified Rous sarcoma virus plasmid, wrapped in a liposome-like sheath, and injected into the lesions of a melanoma patient, caused the effective regression of metastases in the lungs and the lysing of local skin nodules remote from the injection sites. However, as promising as these results are, it is still disadvantageous in the fact that efficacy requires injection into cancer lesions.

By contrast, the present method improves such techniques by a pretargeting step, which comprises administration and delivery of a ligand- (or anti-ligand) targeting moiety conjugate to the targeted sites, i.e., tumor cells, followed by the administration of the nucleic acid sequence (e.g., plasmid) containing liposome, wherein said liposome is attached to a ligand or anti-ligand which binds the conjugate which has been pretargeted to the in vivo site.

In the preferred embodiment, the nucleic acid sequence containing liposome will be attached to biotin, avidin or streptavidin. As evidenced by the afore-cited literature references, it can be seen that methods for attachment of proteins and other compounds to liposomes are also well known in the art. In the most preferred embodiment, the liposomes will be attached to biotin. In this regard, the binding of biotinylated liposomes containing plasmid DNA has been previously reported (See, e.g., Klibanose et al., *Vetn. Akad. Med., Nauk. SSR* 8, 50–54 (1990), and Kitano et al., *Biotech. Appl. Biochem.*, 14, 192–201 (1991)) and ranges from $10^{-9}$ to $10^{-11}$.

The attachment of the ligand or anti-ligand to liposomes, e.g., biotin, should substantially enhance the pharmacokinetics of the liposome encapsulated nucleic acid sequence when used in pretargeting methods since it should facilitate the efficient delivery of such liposome to the targeted site, i.e., tumor cells.

Preferably, the conjugates to be used in the subject pretargeting gene therapy protocol will be administered by intravenous administration, however any systemic route of administration may be utilized. The biotinylated plasmid containing liposome composition will preferably be administered subsequent to the pretargeted (ligand or anti-ligand) targeting moiety conjugate.

Preferably, the encapsulated plasmid will be $\leq 3$ kilobases, which equates to a molecular weight of $\approx 108,000$. With such a size and molecular weight, the liposome containing plasmid should localize effectively on the tumor and be taken up by the reticuloendothelial system (RES). Such plasmids will then be internalized into the targeted cell, wherein the nucleic acid sequence contained therein is expressed to impart the desired therapeutic effect. Moreover, to enhance the internalization of such plasmid, the liposome membrane encapsulating the nucleic acid sequence may be designed such that it fuses with the targeted cell membrane or is osmotically sensitive such that it provides for internalization of the encapsulated plasmid DNA into the target cells.

The dosage effective amount of the liposome encapsulated nucleic acid sequence, e.g., plasmids containing nucleic sequence encoding a desired therapeutic polypeptide, will depend upon factors such as the disease being treated, the condition of the treated host, the particular targeted nucleic acid sequence, and its levels of expression. Effective dosages and dosage regimens may be determined by one skilled in the art.

It is still another object of the invention to further improve the efficacy of the described two and three-step pretargeting therapeutic methods by the administration of "sensitizers" which potentiate the efficacy of the targeted active agent, e.g., a radioactive active agent or a chemotherapeutic active agent.

In this regard, it is known that some cells, i.e., hypoxic (oxygen deficient cells) are resistant to the action of active agents, e.g., radioactive and chemotherapeutic active agents. In the case of some chemotherapeutic agents this is believed to occur because some chemotherapy regimens are oxygen dependent. In particular, the efficacy of such methods may require oxygen to enable active cell growth and cell multiplication because the particular agent is unable to effectively kill non-actively growing cells. Also, it is believed by some researchers that hypoxic cells have low energy reserves and therefore are less able to actively transport chemotherapeutic agents across their cell membranes. This, of course, is only a significant concern if internalization is required for the desired cytotoxic effect.

Because of such problems, if the targeted site, e.g., a tumor, contains a large number of hypoxic cells, it may be difficult to administer a sufficient dosage of the radioactive active agent or chemotherapeutic active agent which provides for killing of hypoxic cells but which does not cause adverse effects to normal tissues. Such problems are particularly prevalent for solid tumors which, given their morphology, tend to contain greater numbers of hypoxic cells.

In this specific regard, it has been reported that the efficacy of radioactive or chemotherapeutic active agents may be enhanced against hypoxic cells by the administration of "sensitizers". In general, sensitizers comprise any compound capable of potentiating the cytotoxicity of the particular active agent, e.g., a radioactive material or chemotherapeutic agent to hypoxic or other resistant cells. Such sensitizers are well known in the art.

An effective class of sensitizers are oxygen carriers. However, this property is not in and of itself sufficient. Additionally, such compounds preferably exhibit at least one and preferably all of the following properties:

i) be capable of rapid transfer to dense cell populations characterizing hypoxic tumor cells or to the vasculature thereof;

ii) exhibit favorable residence time in a mammalian system, i.e., not be too rapidly eliminate by excretion, transpiration or metabolism and not be subject to undue accumulation in the system (e.g., liver and spleen); and iii) exhibit little or no toxicity to normal (euoxic cells).

Ideally, such compounds, if used systemically diffuse quickly through the vasculature, pick up oxygen in the lungs, remain in the cardiovascular system for a sufficient time during therapy, and then are rapidly eliminated without undue toxicity. Preferably the residence time for such compounds is about 10 to 12 days. However, shorter times, e.g., on the order of as little as 2 to 8 hours, may be sufficient for short term therapies, e.g., the subject pretargeting therapeutic protocols which deliver radioactivity to targeted sites.

The present invention embraces the administration of such sensitizers at any point during the described therapeutic pretargeting methods. Moreover, the present invention embraces the administration of any compound or compounds or composition containing which enhances (sensitizes) efficacy of cytotoxic agents against hypoxic cells.

Examples of sensitizers which facilitate oxygen transfer to hypoxic cells are well known in the art and include, e.g., the perfluoro compounds and compositions containing described in U.S. Pat. No. 4,742,050 to Yuhas et al., issued on May 3, 1988; the brominated perfluorocarbon compounds and emulsions containing described in U.S. Pat. No. 4,865,836 to Long, Jr. issued on Sep. 12, 1989 and U.S. Pat. No. 5,080,885 to Long, Jr. issued on Jan. 14, 1992; the perfluorocarbon compounds disclosed in U.S. Pat. No. 4,815,446 to McIntosh issued on Mar. 2, 1989; the perfluorocarbon compounds and dispersants containing disclosed in U.S. Pat. No. 4,889,525 to Yuhas et al. and issued on Dec. 26, 1989; as well as in the perfluorooctyl bromide emulsion described by Rockwell et al., Radiotherapy and Oncology, 22, 92–98 (1991); and Rockwell et al., Int. J. Radiation Oncology Biol. Phys., 22, 87–93 (1992). Also, hemoglobin enhances oxygen delivery as a protein solution (J. Cancer Rev. Clin. Oncol., 120, 85–90 (1993). This list is only representative of the available of representative radiation and chemotherapeutic sensitizers. All of these references are incorporated by reference in their entirety.

The choice of a specific sensitizer in the subject pretargeting protocols will depend on a variety of factors, including whether the treatment is in conjunction with radiotherapy, chemotherapy, or both; the character and locus of the hypoxia; the potency of the perfluoro compound or hemoglobin as a sensitizer; toxicity of the oxygen delivery agent to normal cells and to the host mammal; capability of forming sufficiently small particle size dispersions and sufficiently stable dispersions to diffuse rapidly to the region of the hypoxic cells; residence time in the mammal, including accumulation tendencies; and similar considerations familiar to those knowledgeable in the sensitization art. Guidance for such selection can be obtained from the blood substitute art, particularly as to oxygen transport capability, dispersion particle size and stability, mammalian residence time, and cytotoxicity.

"Perfluoro compound" or "perfluorocarbon" as used herein refers to a substantially fluorinated or completely fluorinated material which is generally but not necessarily a liquid at ambient temperature and pressure. "Substantially fluorinated" as used herein means that most of the hydrogen atoms of a compound have been replaced by fluorine atoms, such that further replacement does not substantially increase the oxygen transport capability of the material. It is believed that this level is reached when at least about 80–90% of the hydrogen atoms have been replaced by fluorine atoms. However, it is preferred that at least 95% of the hydrogen atoms have been replaced, more preferably at least 98% and most preferably, 100%. In the aforementioned U.S. Pat. Nos. 3,911,138 and 4,105,798, the ability to transport oxygen is related to the solubility in the materials of a gas such as oxygen. These patents suggest that the perfluorinated materials will absorb 10–100 cc of oxygen per 100 c of material at 25° C. and 760 milliliters of mercury.

Representative of the perfluoro compounds useful in pretargeting methods are the perfluorinated derivatives of chemically inert $C_9$–$C_{18}$ polycyclic compounds such as bicyclononanes (e.g., bicyclo [3.3.1] nonane and trimethylbicyclo [e.e.1] nonane, 3-methylbicyclo [3.3.1] nonane and trimethylbicyclo [3.3.1] nonane); adamantane and alkyl ($C_1$–$C_6$) adamantanes such as methyl and dimethyladamantane, ethyl and diethyladamantane, trimethyladamantane, ethylmethyladamantane, ethyldimethyladamantane and triethyladamantane; methyldiadamantane and trimethyldiadamantane; methyl and dimethylbicyclooctanes; tetrahydrobinor-S, pinane, camphane, decalin and alkyl decalins such as 1-methyldecalin; and 1,4,6-9-dimethanodecalin; bicyclo [4.3.2] undecane, bicyclo [5.3.0] decane, bicyclo [2.2.1] octane, tricycl [5.2.1.o$^{2,6}$] decane, methyltricyclo [5.2.1.o$^{2,6}$] decane, and the like; or any mixtures thereof. Hereto atom perfluoro compounds include F-tributyl amine, F-tripropyl amine and F-N,N-dimethylcyclohexylmethylamine; perfluoro ethers such as F-2-butyltetrahydrofuran, F-2-butylfuran, F-hydrofuran, the 1,2,2,2,-tetrafluoromethyl ether of F-(2,5,8-trimethyl-3,6,9-trioxa-1-dodecanol), F-N-methyldecahydroquinoline, F-1-methyloctahydroquinolizine, F-octahydroquinolidine and FN-cyclohexylpyrrolidine. Aromatic and aliphatic compounds include F-naphthalene, F-1-methyl-napthaline, F-n-methyl-morpholine, F-n-heptane and 1,2-bisnonylfluorobutylenthylene.

Dispersants for uniformly dispersing the perfluoro compounds in an aqueous medium are known and include, e.g., nonionic surfactants. In some compositions, e.g., in cases where the dispersions are to be used non-systemically, such as in topical or local treatments, ionic or amphoteric surfactants may be used to disperse the perfluoro compounds. Because systemic treatments require careful attention to physiological acceptability of the compounds, such as isotonic character, ionic surfactants are less desirable, although it is possible to offset or moderate their ionic character by formulating the dispersions with electrolytes or other additives. Suitable dispersants are described in the above-referenced publications.

Oxygen transporting perfluoro compound, when used as sensitizers in the subject pretargeting methods, may be administered to a mammal locally or in any systemic fashion, whether intravenous, subcutaneous, intramuscular, parenteral, intraperitoneal or oral. Preferably, administration will be systemic and at a site enabling the dispersion to traverse the lungs to pick up oxygen and to transport the oxygen to the hypoxic tumor cells. Dosages of the dispersion will be predetermined in accordance with the site and character of the hypoxia, whether or not the treatment is a supplement to hyperbaric oxygen treatment, the systemic tolerance (toxicity) of the mammal to the specific formulation, and other factors known to the therapist. Generally, fluorocrits (cc of PFC per 100 ml blood) of the perfluoro compound should be in the range of about 3–10%, although lower or higher fluorocrits in special circumstances may be sufficient or required. If the administration is a supplement to hyperbaric oxygen treatment, or other form of primary oxygen infusion, the fluorucrit need not be over 3.5%, and the partial pressure of oxygen in the inspired air may be up to about 2 atmospheres at 100% oxygen. As a maximum in most cases, hyperbaric oxygen administration would be 30 minutes at 2 atmospheres 100% oxygen pressure, and these conditions are known to be well within tolerated levels. However, the duration, content and pressure of the primary oxygenation in specific cases again will depend upon various factors, such as the health of the mammal or patient, the site of the hypoxia, and other conditions familiar to the radio- or chemotherapist.

Contact of the PFC dispersion may be with the hypoxia cells or with the tumor cell vasculature, such that the oxygen carried by the PFC may transfer to the tumor/vasculature interface. In other words, while the ideal may be direct contact between the PFC dispersion and the hypoxic cells, this may not be achievable and in fact is not required, since excess oxygen, wherever present in the tumor mass, will tend to become distributed throughout the mass, and thus reach the hypoxic cells.

The dosage of the sensitizing agent prior to irradiation and/or chemotherapy will also be controlled by various conditions, including the rate at which the perfluoro compound travels to the hypoxia tumor cells, the degree of sensitization desired, and the cardiovascular half-life residence time of the dispersion in the cardiovascular system and in the hypoxia tissues. For some treatments (such as brief radiation treatments) an acceptable cardiovascular (serum) half-life can be as brief as about 2 to 4 hours. This duration indicates that the perfluoro compound moves rapidly to the hypoxia tumor cells and transfers its oxygen to the cells. In this connection an outstanding property of the preferred dispersions of the invention is an extremely small particle size, which particle size is maintained over substantial periods. The small particle size enables the dispersions to quickly traverse the vasculature to the site of the hypoxia. For example, an average particle size of 0.05 to 0.2 micron has been observed and has been maintained for several months and up to a year or more.

The dispersions may be oxygenated prior to infusion into the mammalian body and this may be expedient when injection is at or near the site of the hypoxia rather than at a site where oxygen transfer from the lungs and arteries is anticipated. Prior oxygenation in such manner may be accomplished by any means, such as flushing or blanketing a vessel containing the dispersion with oxygen or air, or bubbling oxygen or air through the dispersion prior to administration. When the treatment is a supplement to hyperbaric oxygen treatment, preoxygenation in the manner described may also be practiced. In every case of preoxygenation, however, there may be a loss of oxygen prior to entry of the dispersion into the region of the hypoxic tumor cells, that, during transit of the dispersion to the cells; hence, preoxygenation generally is not preferred.

The types, mode of application and sites of radiation treatments are well known and do not require detailed description. However, it will be evident that irradiation can be accomplished by external application or by internal placement of radiation sources near or at the site of the hypoxia. Accordingly, the irradiation may be achieved with x-rays, gamma rays, neutrons and the like, or with implanted radium, iridium or cesium sources. Conventional radiation therapy (200 rads per day, five days per week for six to eight weeks) may be employed but dosage and total duration of treatment may be adjusted as required in particular circumstances.

The sensitizing method when used in the pretargeting methods of the present invention will be effective for all types of hypoxic tumor cells, whether such cells be in suspension (as in leukemia) or in solid form, but the invention is particularly effective for solid tumors. Because systemic distribution of the dispersions is rapid, primarily due to the extremely small and stable particle size of the preferred dispersions of the invention, hypoxia at practically any site may be sensitized in accordance with the invention.

Chemotherapy is often used in combination with radiotherapy to destroy or control hypoxic tumor cells and therefore the sensitization techniques of the invention can be applied simultaneously or sequentially to chemotherapy and radiotherapy. When dual therapy is used, a sensitizer dispersion will normally be selected which has the cardiovascular residence time effective to cover the duration of both treatments, or if the residence time is short, the sensitizer dosage can be suitably increased or adjusted. It is known that some chemotherapeutic agents are oxygen dependent in terms of requiring oxygen for active transport of the CT drug into the cell, for cell cycling control or CT enhancement. Hence, oxygen must be supplied in free form or by means of a carrier. Because perfluoro compounds and their dispersions are capable of transferring large quantities of oxygen, chemotherapy based upon drugs which are oxygen dependent will also benefit by formulating the drugs with an RS agent, or sequentially administering the RS and CT agents. Methotrexate is an example of a CT drug thought to require oxygen for active transport into the cell. Vinblastine and Vincristine are drugs which require oxygen for cell cycling.

CT drugs which may not be oxygen dependent may also be administered in conjunction with the sensitizing techniques of the invention. Among such drugs may be mentioned Androgens, Estrogens, Anti-estrogen, Progestins, Adrenal Steroids, Nitrogen Mustard, Chlorambucil, Phenylalanine Mustard, Cyclophosphamide, Thio-TEPA, Busulfan, 6-Mercaptopurine, 6-Thioguanine, 5-Fluorouracil, Cytosine Arabinoside, Adriamycin, Dactinomucin, Daunomucin, Bleomucin, Mithramycin, Mitomucin-C, BCNU, CCNU, Methyl-CCNU, DTIC, Hydroxyurea, Cis-Platinum (cis-platinum (II) diamminedichloride), Procarbazine, Hexamethylmelamine, L-Asparaginase, and the like.

Those perfluoro compounds useful as RS agents but which also have radiopaque properties are particularly valuable for the purpose of the present invention. Such compounds include brominated perfluorohydrocarbons such as F-perfluoroctylbromide and brominated perfluoroethers, such as F-1-bromobutylisopropylether, F-1-bromoethylisopropyl ether and other brominated perfluoro organo ethers described, for example, in U.S. Pat. No. 3,453,333. The radioimaging properties of such compounds permit monitoring of their RS effects as well as toxicity to surrounding normal cells and hence serve as diagnostic agents as well as RS agents. However, if the perfluoro compounds do not also exhibit radiopacity, the dispersions containing the perfluoro compounds may be formulated with other, known, radiopaque agents in order to provide a similar opportunity for monitoring radiosensitization potential. The radioimaging may be practiced as in conventional radiography or computer axial tomography (CAT) radiography, or by the newer NMR techniques. The brominated compounds as RI agents may be used near or in aqueous dispersion, for example as oil-in-water or water-in-oil emulsions containing about 10–90% by volume of water and about 0.5–10% by weight of a dispersant.

Radioprotection may also be practiced in conjunction with radiosensitization. Radioprotective agents are those which preferentially protect normal tissues from radiation injury. When practiced with radiosensitization, the objective is to reduce injury to the normal tissues, which injury may occur when the RS agents are used in the absence of the RP agents. Sulfhydryl-containing agents generally are known to be effective RP materials, such as aminoethylisothiuronium or the phosphorothicate derivatives of betamerdaptoethylamine reviewed in the article by J. M. Yuhas, "On the Potential Application of Radioprotective Drugs in Solid Tumor Radiotherapy," appearing in Radiation-Drug Interactions in the Treatment of Cancer, edited by G. H. Sokol and R. P. Maickel, John Wylie and Sons, Inc., (1980), pp. 113–135. Another RP agent is S-2-(3-aminopropylamino) ethylphosphorothioic acid, also described in the article by Yuhas et al. appearing in *Cancer Clinical Trials*, (1980), 3, 211–216.

Other suitable sensitizers include fluorocarbon emulsions which comprise at least one perfluorocarbon compound having 9 to 11 carbon atoms selected from the group consisting of perfluorodecalin, perfluoromethyldecalin, perfluoroalkylcyclohexanes having 3 to 5 carbon atoms in the alkyl, perfluoro alkyltetrahydrofurans having 5 to 7 carbon atoms in the alkyl, perfluoro alkyltetrahydropyrans having 4 to 6 carbon atoms in the alkyl, perfluoroalkanes having 9 to 11 carbon atoms; and may have at least one perfluoro tert-amine having 9 to 11 carbon atoms selected from the group consisting of perfluoro tert-alkylamines having 9 to 11 carbon atoms, perfluoro N-alkylpiperidines having 4 to 6 carbon atoms in the alkyl and perfluoro N-alkylmorphoines having 5 to 7 carbon atoms in the alkyl. Such emulsions further comprise high-molecular-weight nonionic surfactant having a molecular weight of about 2,000 to 20,000; a phospholipid; and at least one fatty acid compound selected from the group consisting of fatty acids having 8 to 22 carbon atoms; and physiologically acceptable salts and monoglycerides thereof. The ratio of the perfluorocarbon compound and the said perfluorotert-amine is 95-50 to 5-50 by weight.

The previously identified sensitizers promote the efficacy of radioactive compounds and chemotherapeutic agents by providing for enhanced delivery of oxygen to the targeted site, e.g., tumor cells, thereby enhancing the activity of such active agents against hypoxic cells. The present invention further contemplates enhancement of pretargeting protocols by other means for exposing target sites to enhanced oxygen concentrations. For example, this may be effected by directly supplying the cells with oxygen, e.g., by administration of compounds which provide for production of oxygen, e.g., hydrogen peroxide or by hyperbaric oxygen administration. This essentially will comprise exposing the treated patient to high concentrations of oxygen during the pretargeting protocol, e.g., before, during or after administration of the active agent containing conjugate. In particular, the patient is placed in a hyperbaric oxygen chamber containing high oxygen concentrations at high pressure during, before or after pretargeting to facilitate delivery of oxygen to hypoxic cells. This results in the diffusion of oxygen to hypoxic tissues, and therefore potentiates the efficacy of therapeutic pretargeting protocols.

Another application of the present invention is in the area of photodynamic therapy. Photodynamic therapy itself is a two-step procedure as follows:

a photosensitizing agent that absorbs a certain wavelength of light is topically or systemically administered to the recipient and localizes to the target site; and target cells are illuminated with a light source of the appropriate wavelength. When the photosensitizing agent absorbs the light, it transfers the absorbed energy to oxygen molecules dissolved in the tissue, thereby producing an active oxygen species which, in turn, destroys nearby biochemicals and, therefore, cells in the vicinity (primarily the target cells, provided that the photosensitizing agent has selectively localized thereto).

The present invention provides pretargeting photodynamic therapy protocols as set forth below.

The two-step approach involves:

administering to the recipient a first conjugate comprising a targeting moiety and a member of a ligand-anti-ligand binding pair, wherein the first conjugate localizes to a target site;

optionally administering to the recipient a clearing agent capable of directing the clearance of circulating conjugate from the recipient or optionally treating the recipient with a clearing device or an alternative clearing procedure to substantially remove circulating conjugate from the recipient; and administering to the recipient a second conjugate comprising a photosensitizing agent and a ligand/anti-ligand binding pair member, wherein the second conjugate binding pair member is complementary to that of the first conjugate and wherein the photosensitizing agent or the conjugate as a whole is chemically modified to induce rapid and, preferably, renal clearance thereof from the recipient.

One alternative to the optional clearance step set forth above is simply to allow an amount of time to pass that is sufficient to permit the recipient's native clearance mechanisms to substantially remove circulating conjugate.

The three-step approach involves:

administering to the recipient a first conjugate comprising a targeting moiety and a ligand, wherein the targeting moiety-ligand conjugate localizes to a target site;

administering to the recipient an anti-ligand; and administering to the recipient a second conjugate comprising the ligand and a photosensitive agent, wherein the photosensitizing agent or the conjugate as a whole is chemically modified to induce rapid and, preferably, renal clearance thereof from the recipient and wherein second conjugate localization at the target site is enhanced as a result of prior localization of the first conjugate.

In both the two-step and the three-step approaches to photodynamic therapy set forth above, the final step is subjecting the recipient to light of the appropriate wavelength. This step is preferably conducted between from about 2 hours to about 72 hours following administration of the photosensitizing agent-containing conjugate.

Optionally, an additional step of clearing the photosensitizing agent-containing conjugate may be employed. In this manner, rapid clearance of that agent may be facilitated. This clearance step may be achieved by administration of anti-ligand or galactosylated anti-ligand, for example, when photosensitizing agent-ligand conjugates are employed and by administration of ligand-HSA-galactose, for example, when photosensitizing agent-anti-ligand conjugates are employed.

To achieve target cell destruction, the photosensitizing agent is, preferably, selectively taken up by target cells. In the practice of the present invention, selective target site accretion is primarily facilitated by conjugating the photosensitizing agent to a ligand or an anti-ligand that binds a pretargeted anti-ligand or ligand with high affinity. Route of administration can also impact photosensitizing agent accretion, e.g., intraarterial administration for arterially accessible target sites.

Also, it is preferred that the photosensitizing agent is retained at target cell sites for a period of time. Target site retention may be imparted by the targeting moiety through which the photosensitizing agent is associated with the target cell, if any, with release of the photosensitizing agent from association with the targeting moiety over time by the use of cleavable linkers or like methods; by target cell biochemistry (i.e., photosensitizing agents soluble at low pH will be retained longer by target cells exhibiting low pH such as tumor cells); or by the hydrophobicity of the photosensitizing agent (greater hydrophobicity enhances retention).

Preferred photosentizing agents for use in pretargeting protocols of the present invention directed at destroying target cells that are not adjacent or closely adjacent to the skin of the recipient also exhibit the ability to absorb light of longer wavelengths. The longer the wavelength of light, the deeper that light can penetrate tissue. Consequently, photosensitizing agents that absorb longer wavelengths (e.g., between about 600 and about 800 nm) can act on target sites embedded more deeply in tissue than photosensitizing agents absorbing light of lower wavelengths. While initially only skin cancers were treated with photodynamic therapy, the conventional procedure has now been applied to early stage tumors in the head and neck, brain, lung, gastrointestinal and genitourinary tracts.

In addition, preferred photosensitizing agents for use in the practice of the present invention are capable of efficiently producing highly active oxygen species. Generally, photosensitizing agents exhibiting greater hydrophobicity are more efficient at producing highly active oxygen species than such agents exhibiting lesser hydrophobicity. This greater efficiency appears to be related to the greater ability of hydrophobic moieties to penetrate cell membranes.

Common photosensitizing agents are porphyrin derivatives with a strong absorption band between 600 and 700 nm (red light). Chemical modification of porphyrin compounds is undertaken to enhance performance of those compounds in photodynamic therapy protocols. Phthalocyanines, synthetic porphyrins when chelated with aluminum or zinc (e.g., chloroaluminum sulfonated phthalocyanines), are effective to destroy target cells. Photofrin II, an ether/ester derivative of porphyrin, is presently the most commonly employed photosensitizing agent in photodynamic therapy. Other exemplary photosensitizing agents are chlorins (e.g., chlorin e6, tin chlorin e6, bacteriochlorin A, bacteriochlorophyllin a, mono- and di-L-aspartyl chlorin e6, and the like); porphyrin diethers (e.g., di-isobutyl ethers and di-hexyl ethers); purpurins (e.g., NT2), benzoporphyrin derivatives (porphines, such as isomers of 5, 10, 15, 20-tetra (hydroxyphenyl)-porphyrin; and sulfonated derivatives of tetraphenylporphine, such as $TPPS_2$ (a derivative of $TPPS_4$ with two rather than four sulfonate groups) and $TPPS_4$ (5,10,15,20,-tetra(4-sulfonato-phenyl)-21H,23H,porphine)); and the like. Generally, these exemplary photosensitizing agents have carboxylate groups available for conjugation.

Any light source can be employed to activate the photosensitizing agents, provided it has the appropriate spectral characteristics. Various types of laser lights are being used for this purpose. A laser can be coupled to a fiber-optic cable to deliver light precisely to the recipient without any energy loss. Other techniques, such as chemiluminescence can be used for local delivery of high intensity light.

In addition, light sources encountered by recipients in their normal activities (e.g., direct sunlight) also cause photosensitizing agents to produce active oxygen molecules. This is one of the limitations of conventional photodynamic therapy. Photosensitizing agents have long half-lives, generally up to about two months. A new benzoporphyrin derivative has exhibited a clearance time of about one week. In either even, recipients must avoid direct sunlight for the relevant time period to avoid non-target tissue toxicity as the photosensitizing agent is cleared.

Photosensitizing agents of the present invention and methods of using them facilitate target cell-specific accretion of photosensitizing agent and obviate the necessity for a recipient avoiding direct sunlight. When the agents and protocols of the present invention are employed, the recipient may even obtain a residual benefit from exposure to such sunlight.

By decoupling the slow target site accretion of a targeting molecule from the kinetics of photosensitizing agent accretion and by utilizing a high affinity ligand-anti-ligand system to rapidly capture photosensitizing agent conjugate, that active agent can quickly and specifically accrete to the target site. The long circulating half-life of the photosensitizing agent renders this process somewhat inconvenient for the recipient. Chemical modification of the photosensitizing agent to facilitate rapid excretion from the recipient would obviate this difficulty. Rapid and, preferably, renal excretion of the photosensitizing agent-containing conjugate would permit the recipient to undertake normal activities within a few hours following photosensitizing agent administration. At that time, substantially all of the photosensitizing agent remaining in the recipient's system is located at the target site. Consequently, exposure of the target to the directed light source could be followed essentially immediately with the exposure of the recipient to an ambient light source of a wavelength appropriate for producing activated oxygen with a substantially reduced risk of non-target toxicity.

Photosensitizing agents may be coupled to ligands or anti-ligands in accordance with known techniques. For example, porphyrin biotinylation may be undertaken as set forth below. The carboxylic acid functionality of porphyrin derivatives is activated by reaction with hydroxybenztriazole. Biocytin or biocytin analogs are reacted with porphyrin benztriazole active ester in a biocytin:porphyrin molar ratio ranging from about 2 to about 4. Porphyrins so derivatized contain 1 to 3 biotins per porphyrin. Biotin conjugation is evaluated using the ($\mu$-hydroxybenzene) benzoic acid (HABA) displacement assay employing pronase digested biotinylated porphyrin. *Journal of Biological Chemistry*, 94: 23C–24C, 1965.

Chemical modifications employed in the present invention are those that facilitate rapid excretion of photosensitizing agent-containing conjugates from the recipient. Preferably, such modifications also direct the photosensitizing agent-containing conjugate to renal excretion. Appropriate chemical modifications may be made to the photosensitizing agent or to the photosensitizing agent-containing conjugate. Preferably, the photosensitizing agent-conjugate may be treated with anion-forming agents as described below.

Useful anion-forming agents include compounds incorporating an anhydride and/or at least one COOH group, such as succinic anhydride, other cyclic acid anhydrides, phthalic anhydride, maleic anhydride, N-ethyl maleimide substituted with carboxyl groups, aliphatic anhydrides (e.g., acetic anhydride), aromatic anhydrides, pH-reversible anhydrides (e.g., citraconic anhydride and dimethyl maleic anhydride), alpha halo acids such as bromoacetate and iodoacetate, and diacids or triacids substituted with a functional group that reacts with a functional group of a molecule to be charge-modified.

For example, succinic anhydride is dissolved in DMSO or another dry organic solvent at a concentration of 40 mg per 200 microliters. This succinic anhydride solution (or a dilution thereof up to 2.5 ml in anhydrous DMSO, $1.73 \times 10^{-2}M$) is added, for example, to a protein (e.g., antibody, antibody fragment, ligand, anti-ligand or conjugate containing one or more of these components) solution (e.g., 3–5 mg/ml in carbonate/bicarbonate buffer, pH 8.5–9.0) at molar ratios of succinic anhydride to protein of 1:5, 1:10 or 1:25. The reaction is carried out at room temperature for 15–30 minutes. After reaction completion, succinic acid is removed by ultrafiltration or by gel filtration. The degree of isoelectric shift is determined by isoelectric focusing.

The ability of charge-modified ligands and charge-modified anti-ligands to bind to the complementary member of the ligand/anti-ligand pair is tested in accordance with know procedures for testing ligand/anti-ligand binding affinity.

For example, the photosensitizing agent-containing conjugates may be modified by derivatization with a biodistribution directing molecule such as the following: hydrophilic polymers, such as 10 kD dextran, larger dextran molecules (having molecular weights ranging from about 20 to about 70 kD), polyglutamates (having molecular weights ranging from about 5 to about 50 kD), succinylated polylysines (having molecular weights ranging from about 5 to about 50 kD) and defined oligosaccharides, i.e., oligosaccharides produced synthetically such that the structure is chemically defined and of sufficient size to substantially overcome liver and other organ uptake which facilitates renal excretion via glomular filtration. Polymers, such as those described above, are removed from recipients by renal excretion and, therefore, polymeric derivatization facilitates renal excretion of polymer-containing conjugate.

Biotin-polymer-porphyrin conjugates may be formed using commercially available biotinylated, lysine-derivatized dextran polymer (e.g., biotin-dextran, lysine fixable available from Sigma Chemical Co., St. Louis, Mo.). The lysine derivatized-biotin is conjugated via the reaction of a lysine epsilon-amino group, for example, with the benztriazole activated ester of the porphyrin described above. Other active esters as are employed in the art may also be used for this purpose (e.g., N-hydroxysuccinimide; phenols substituted with strong electron withdrawing groups such as nitro and fluoro groups; and the like). Alternatively, biotin-polymer-porphyrin/chlorin conjugates, for example, may be formed using commercially available biotinylated, lysine-derivatized dextran polymer that is activated by reaction of a lysine residue thereof with the bifunctional reagent, succinimidyl-4-(N-maleimido-methyl) cyclohexane-1-carboxylate (SMCC), under conditions analogous to the porphyrin biotinylation set forth above (e.g., pH, molar ratio and like conditions). The SMCC-derivatized dextran polymer now contains the reactive maleimide functional group available for conjugation with the thio analog of 5, 10, 15, 20-tetra-(4-hydroxyphenyl)porphine, for example. This porphine is prepared from the corresponding p-hydroxyphenylporphine using synthetic procedures that are known in the art.

Derivatization alternatives include $(DTPA)_n$ where n ranges from about 1 to about 2. DTPA, diethylene triamine penta-acetic acid, e.g., DTPA cyclic anhydride, may be linked by an amide bond via a native carboxylate group or a synthetically added carboxylate group of a photosensitizer.

Another derivatization alternative is a hydrazine analog of 5,10,15,20-tetra-(4-hydroxyphenyl)porphine which is prepared from the corresponding p- hydroxyphenylporphine via the p-chlorophenylporphine intermediate using conventional synthetic procedures. Periodate-oxidized biotinylated dextran contains reactive aldehyde functional groups for conjugation with the hydrazine analog.

Sustained release dosage forms may also be employed in the process of the present invention to deliver photosensitizing agent to target cells through the pretargeting approach. In this manner, the therapeutic effect of the photosensitizing agent may be achieved over a period of time. Ligand or anti-ligand derivatized liposomes may be employed for this purpose. Hawrot et al., U.S. Pat. No. 4,948,590, for example, discuss streptavidinylated liposomes and the encapsulation of active agents therein.

Alternatively, microparticulate or nanoparticulate polymeric bead dosage forms may be employed, such as those discussed in Example IX herein for use as clearing agents. In this case, the active agent will be encapsulated in the particulate dosage forms which have a number of ligand or anti-ligand molecules bound thereon. In this manner, active agent is delivered to a target site via ligand-anti-ligand binding and active agent is release at that site over time to provide a sustained therapeutic benefit.

In general, the procedure for forming particulate dosage forms of the present invention involves dissolving the polymer in a halogenated hydrocarbon solvent, dispersing an active agent solution (preferably aqueous) therein, and adding an additional agent that acts as a solvent for the halogenated hydrocarbon solvent but not for the polymer. The polymer precipitates out from the polymer-halogenated hydrocarbon solution onto droplets of the active agent containing solution and entraps the active agent. Preferably the active agent is substantially uniformly dispersed within the sustained release dosage form of the present invention. Following particulate formation, they are washed and hardened with an organic solvent. Water washing and aqueous non-ionic surfactant washing steps follow, prior to drying at room temperature under vacuum.

For biocompatibility purposes, particulate dosage forms, characterized by an active agent dispersed therein in matrix form, are sterilized prior to packaging, storage or administration. Sterilization may be conducted in any convenient manner therefor. For example, the particulates can be irradiated with gamma radiation, provided that exposure to such radiation does not adversely impact the structure or function of the active agent dispersed in the therapeutic agent-polymer matrix or the ligand or anti-ligand attached thereto. If the active agent, ligand or anti-ligand is so adversely impacted, the particulate dosage forms can be produced under sterile conditions.

Release of the active agent from the particulate dosage forms of the present invention can occur as a result of both diffusion and particulate matrix erosion. Biodegradation rate directly impacts active agent release kinetics. The biodegradation rate is regulable by alteration of the composition or structure of the sustained release dosage form. For example, alteration of the lactide/glycolide ratio in preferred dosage forms of the present invention can be conducted, as described by Tice et al., "Biodegradable Controlled-Release Parenteral Systems," *Pharmaceutical Technology,* pp. 26–35, 1984; by inclusion of polymer hydrolysis modifying agents, such as citric acid and sodium carbonate, as described by Kent et al., "Microencapsulation of Water Soluble Active Polypeptides," U.S. Pat. No. 4,675,189; by altering the loading of active agent in the lactide/glycolide polymer, the degradation rate being inversely proportional to the amount of active agent contained therein, and by judicious selection of an appropriate analog of a common family of active agents that exhibit different potencies so as to alter said core loadings; and by variation of particulate size, as described by Beck et al., "Poly(DL-Lactide-Co-Glycolide)/ Norethisterone Microcapsules: An Injectable Biodegradable Contraceptive," *Biol. Reprod.,* 28: 186–195, 1983, or the like. All of the aforementioned methods of regulating biodegradation rate influence the intrinsic viscosity of the polymer containing matrix, thereby altering the hydration rate thereof.

The preferred lactide/glycolide structure is biocompatible with the mammalian physiological environment. Also, these preferred sustained release dosage forms have the advantage that biodegradation thereof forms lactic acid and glycolic acid, both normal metabolic products of mammals.

Functional groups required for ligand or anti-ligand bonding to the particles, are optionally included in the particulate structure, along with the non-degradable or biodegradable polymeric units. Functional groups that are exploitable for this purpose include those that are reactive with ligands or anti-ligands such as carboxyl groups, amine groups, sulfhydryl groups and the like. Preferred functional groups include the terminal carboxyl groups of the preferred (lactide-glycolide) polymer containing matrix or the like.

These sustained release dosage forms are also useful with regard to other active agents useful in the practice of the present invention, such as toxins, chemotherapeutic agents, cytokines and the like.

Another strategy that may be employed to increase photosensitizer potency and allow bystander cells to be treated involves the use of cleavable linkers between the biotin or the biotin-biodistribution directing molecule and the photosensitizing agent. The advantage of the controlled instability offered by a cleavable linker is that more hydrophobic photosensitizers could be used. Photosensitizing agents exhibiting enhanced hydrophobicity appear to have increased potency of cell killing when exposed to light of the appropriate wavelength. Because of the rapid targeting and clearance of the photosensitizing agent-containing conjugate, cleavable linkers exhibiting a stability half-life under physiological conditions of several hours (e.g., between from about 3 to about 12 hours) and practical shelf life (e.g., between from about 3 months to about 2 years) may be employed. Exemplary of such cleavable linkers are disulfide linkages, carboxylate ester linkages such as cis-aconitates, hydrazide linkages and the like. Herman et al., *Bioconjugate Chemistry*, 4: 40–405, 1993, for example, describes the synthesis dextran derivatives with thio-specific reactive groups. Such dextran derivatives can be employed in forming conjugates bearing a cleavable disulfide linkage. A hydrazide-linked conjugate may be formed in accordance with the procedure set forth in *PNAS*, 87: 4217–4221, 1990.

Monovalent antibody fragment-anti-ligand or -ligand conjugates may be employed in pretargeting protocols of the present invention. For example, a monovalent antibody fragment-streptavidin conjugate may be used to pretarget streptavidin, preferably in additional embodiments of the two-step aspect of the present invention. Exemplary monovalent antibody fragments useful in these embodiments are Fv, Fab, Fab' and the like. Monovalent antibody fragments, typically exhibiting a molecular weight ranging from about 25 kD (Fv) to about SO kD (Fab, Fab'), are smaller than whole antibody and, therefore, are generally capable of greater target site penetration. Moreover, monovalent binding can result in less binding carrier restriction at the target surface (occurring during use of bivalent antibodies, which bind strongly and adhere to target cell sites thereby creating a barrier to further egress into sublayers of target tissue), thereby improving the homogeneity of targeting.

In addition, smaller molecules are more rapidly cleared from a recipient, thereby decreasing the immunogenicity of the administered small molecule conjugate. A lower percentage of the administered dose of a monovalent fragment conjugate localizes to target in comparison to a whole antibody conjugate. The decreased immunogenicity may permit a greater initial dose of the monovalent fragment conjugate to be administered, however.

A multivalent, with respect to ligand, moiety is preferably then administered. This moiety also has one or more radionuclide associated therewith. As a result, the multivalent moiety serves as both a clearing agent for circulating anti-ligand-containing conjugate (through cross-linking or aggregation of conjugate) and as a therapeutic agent when associated with target bound conjugate. In contrast to the internalization caused by cross-linking described above, cross-linking at the tumor cell surface stabilizes the monovalent fragment-anti-ligand molecule and, therefore, enhances target retention, under appropriate conditions of antigen density at the target cell. In addition, monovalent antibody fragments generally do not internalize as do bivalent or whole antibodies. The difficulty in internalizing monovalent antibodies permits cross-linking by a monovalent moiety serves to stabilize the bound monovalent antibody through multipoint binding. This two-step protocol of the present invention has greater flexibility with respect to dosing, because the decreased fragment immunogenicity allows more streptavidin-containing conjugate, for example, to be administered, and the simultaneous clearance and therapeutic delivery removes the necessity of a separate controlled clearing step.

A potential difficulty in employing two-step and three-step pretargeting protocols involving the biotin-avidin or the biotin-streptavidin ligand-anti-ligand pair is the presence of endogenous biotin. Biotin is also known as vitamin H and is present at an endogenous level in mammalian recipients. Mice, for example, have high levels of endogenous biotin, ranging from about microgram to about nanogram concentrations ($10^{-6}$ to $10^{-9}$ M). Larger mammals, such as rabbits and dogs, exhibit endogenous biotin at lower levels than mice, ranging from about low nanogram to about high nanogram concentrations ($10^{-9}$ to $10^{-11}$ M). Humans exhibit even lower endogenous biotin levels, ranging from about low picogram to about high picogram concentrations ($10^{-12}$ to $10^{-14}$ M). Because endogenous biotin level is impacted by factors such as diet and suppression of gut wall bacteria by oral antibotics, variability in endogenous biotin level will be observed within each mammalian species.

While the two-step and three-step pretargeting methods of the present invention may be conducted despite endogenous biotin, methods of decreasing endogenous biotin or the impact thereof would be useful. One way to diminish the impact of endogenous biotin is to overwhelm the endogenous biotin with a high dose of targeting moiety- streptavidin or -avidin conjugate. More specifically, conjugate is administered in an amount sufficient to substantially bind both the endogenous biotin and sufficient target site epitopes to achieve a diagnostic or therapeutic benefit for the recipient. In the identification of an appropriate conjugate dose, the endogenous biotin level for each individual recipient may be determined, and the conjugate dose selected accordingly. Alternatively, an appropriate conjugate dose may be based upon average endogenous biotin values for the recipient species.

Another method involves a pretreatment with an amount of avidin sufficient to bind up substantially all of a recipient's endogenous biotin. In this method, avidin may be administered intravenously as a bolus dose followed by slow infusion (e.g., avidin in saline or in PBS), preferably from about 5 minutes to about 30 minutes prior to targeting moiety-streptavidin administration. Alternatively, avidin may be administered orally (e.g., as raw egg whites), preferably earlier and at higher doses than an intravenous administration. Still another alternative is administering a high dose of avidin by enema (e.g., avidin in saline), preferably earlier and at higher doses than intravenous administration.

An intravenously administered agent becomes bioavailable faster than an agent administered via oral or enema routes, therefore generally rendering intravenous administered agents more toxic than the agents administered by oral/enema routes. Also, absorption, distribution, kinetics and metabolism of oral/enema administrations are generally slower than intravenous agent administrations, thereby generally requiring a higher dose for oral/enema administrations.

Alternatively, the recipient may be placed on a biotin-free diet prior to conducting a two-step or three-step pretargeting protocol. For example, a mouse recipient of a pretargeting protocol may be placed on a biotin-free diet from about 2 to about 3 days prior to the start of the pretargeting protocol. A larger volume mammal, such as a rabbit or a dog, may be placed on a biotin-free diet from about 3 to about 7 days before the first conjugate administration of a pretargeting protocol of the present invention. A human recipient may be placed on a biotin-free diet (e.g., avoiding dietary sources of biotin such as eggs, nuts, peanut butter, chocolate, candy, yeast, cereals, organ meats such as kidney and liver, meat, meat products, mushrooms, bananas, grapefruit, watermelon, strawberries, beans and legumes) from about 1 to about 2 weeks prior to commencement of the pretargeting protocol. In this manner, the endogenous biotin level of the recipient may be reduced, thereby diminishing any adverse impacts of endogenous biotin on the pretargeting protocol.

An alternative method to address endogenous biotin is the use of oral, non-absorbable antibiotics. Most human endogenous biotin is produced by gut flora (e.g., bacteria, such as *E. coli* and the like). Potent antibiotics are known which destroy gut flora. Such antibiotics are orally administered and are not absorbed from the intestinal tract, so that they are non-toxic to the recipient. Other functional characteristics of suitable antibiotics are as follows: antagonism of growth and/or survival of one or more species of microorganisms that produce biotin; effectiveness at low doses;and the like. Exemplary of such antibiotics are ampicillin, chloramphenicol, erythromycin, oxacillin, nafcillin, oxytetracycline, penicillin-G, penicillin-V, tetracycline, kanamycin, lincomycin, griseofulvin, doxycycline, novobiocin, colistin, chlortetracycline, and the like. To temporarily lower the level of biotin produced by gut flora, oral, non-absorbable antibiotics, such as gentamicin, polymyxin-B, vancomycin and the like, may be administered from about 7 to about 10 days prior to the commencement of the pretargeting protocol.

Combinations of the aforementioned methods may be employed in the practice of the present invention. Of the above methods, all may be employed in combination with two-step pretargeting.

Another embodiment of the pretargeting methodologies of the present invention involves the route of administration of the ligand- or anti-ligand-active agents. In these embodiments of the present invention, the active agent-ligand (e.g., radiolabeled biotin) or -anti-ligand is administered intraarterially using an artery supplying tissue that contains the target. In the radiolabeled biotin example, the high extraction efficiency provided by avidin-biotin interaction facilitates delivery of very high radioactivity levels to the target cells, provided the radioactivity specific activity levels are high. The limit to the amount of radioactivity delivered therefore becomes the biotin binding capacity at the target (i.e., the amount of antibody at the target and the avidin equivalent attached thereto).

For these embodiments of the pretargeting methods of the present invention, particle emitting therapeutic radionuclide resulting from transmutation processes (without non-radioactive carrier forms present) are preferred. Exemplary radionuclides include Y-90, Re-188, At-211, Bi-212 and the like. Other reactor-produced radionuclides are useful in the practice of these embodiments of the present invention, if they are able to bind in amounts delivering a therapeutically effective amount of radiation to the target. A therapeutically effective amount of radiation ranges from about 1500 to about 10,000 cGy depending upon several factors known to nuclear medicine practitioners.

In administering the subject active agent conjugates during therapeutic pretargeting strategies, the active agent containing conjugates is preferably administered in an amount which provides for the requisite therapeutic amount of the active moiety to reach the target site, e.g., a tumor, but which does not result in undue toxicity to normal tissues. Such toxicity is a potential concern if the particular active agent is a cytotoxic agent, e.g., a radioactive material or a cytotoxin.

The preferred dosage and dosage region of the active agent containing conjugate will depend upon factors including the condition of the patient being treated, the particular disease being treated, whether the active agent is administered singularly or in combination with other therapies, the in vivo half life of the active agent, its effects on normal tissues, e.g., kidney and liver, among other factors. For example, the conjugate may, e.g., be administered in a single dosage, e.g., a bolus, in multiple, divided dosages or be administered continuously, e.g., by intravenous infusion.

Suitable dosage and dosage regimen may be determined by one skilled in the art. However, it is expected that some dosage regimens may afford certain intrinsic advantages. For example, it is expected that the administration of divided dosages, e.g., from about 2 to 5 divided dosages of an effective dosage of the active agent conjugate may be advantageous. It is believed that such divided dosages may provide for better, more efficient delivery of the active agent, e.g., a radioactive material or cytotoxin to the targeted site, e.g., a radioactive material or cytotoxin. This is because of the fact that single dosage may in some instances be ineffective or undesirable to provide for the desired saturation of all the ligand or anti-ligand binding sites, e.g., biotin binding sites, contained on the conjugate which has been pretargeted to the target site. While saturation can be achieved by administration of a single higher dosage amount, this may be disadvantageous because it may enhance the potential for non-specific binding of the active agent to normal types. Also, this may result in enhanced levels of active agent in the circulation, which is not specifically bound to target sites, thereby increasing the risk of it binding to normal tissues and therefore causing normal tissue damage.

By contrast, it is expected that such toxicity may potentially be alleviated by the administration of divided doses, more than a single unitary dosage wherein the same amount of the active agent is administered, but over a longer time period. The use of divided dosages should reduce the possibility of non-targeted tissue cytotoxicity, e.g., liver or kidney damage. Also, it should further enable the more efficient delivery of active agent and better saturation of the ligand or anti-ligand binding sites contained on the pretargeted conjugate, e.g., avidin or streptavidin containing conjugate.

Such divided dosages will be administered at a dosage amount and dosage regimen which achieves the desired saturation levels and therapeutic efficacy. This, of course, depends upon the particular active agent contained in the targeted therapeutic conjugate. For example, if a therapeutically effective amount comprises a 500 μg bolus, a divided dosage regimen would instead comprise, e.g., two 250 μg dosages, three ~166 μg dosages, four 125 μg dosages or five 100 μg dosages. The interval between such dosages will vary depending upon the factors enumerated supra, e.g., the particular active agent, its in vivo half life, clearance rate, among other factors. In general, the intervals between dosages will range from about 2 to 12 hours, preferably 2 to 8 hours, and more preferably about 3 to 5 hours.

It is also expected that administration of the therapeutic conjugate via infusion may be advantageous in therapeutic pretargeting protocols. For example, it should enable administration of a constant low dosage of the active agent, thereby providing for the desired delivery of active agent to target site, but reducing the potential for non-specific binding because of lower average concentration of the particular active agent conjugate which is contained in the patient's circulation. In general, efficacious infusion rates will range from about 10 μg/hr. to about 100 μg/hr.

However, this will of course depend upon the particular active agent, the disease being treated, the condition of patient, the therapeutic regimen (e.g., if other therapies are being utilized in combination with pretargeting protocol), etc Determination of optimal rates of infusion may be determined by one skilled in the art. It is especially believed that the above divided dosages and constant infusion will be advantageous for therapeutic pretargeting methods involving the administration of radioactive materials and other cytotoxins, e.g., the Y-90-DOTA-biotin conjugate.

Intraarterial administration pretargeting can be applied to targets present in organs or tissues for which supply arteries are accessible. Exemplary applications for intraarterial delivery aspects of the pretargeting methods of the present invention include treatment of liver tumors through hepatic artery administration, brain primary tumors and metastases through carotid artery administration, lung carcinomas through bronchial artery administration and kidney carcinomas through renal artery administration. Intraarterial administration pretargeting can be conducted using chemotherapeutic drug, toxin and anti-tumor active agents as discussed below. High potency drugs, lymphokines, such as IL-2 and tumor necrosis factor, gamma-interferon, drug/lymphokine-carrier-biotin molecules, biotinylated drugs/lymphokines, and drug/lymphokine/toxin-loaded, biotin-derivatized liposomes are exemplary of active agents and/or dosage forms useful for the delivery thereof in the practice of this embodiment of the present invention.

In embodiments of the present invention employing radionuclide therapeutic agents, the rapid clearance of nontargeted therapeutic agent decreases the exposure of non-target organs, such as bone marrow, to the therapeutic agent. Consequently, higher doses of radiation can be administered absent dose limiting bone marrow toxicity. In addition, pretargeting methods of the present invention optionally include administration of short duration bone marrow protecting agents, such as WR 2721, as well as other protective agents such as IL-3, GM-CSF, G-CSF or a combination of IL-3 and GM-CSF. As a result, even higher doses of radiation can be given, absent dose limiting bone marrow toxicity.

Also, pretargeting techniques are generally characterized by relatively rapid target site accretion of active agent, because of the high affinity binding between the members of a ligand-anti-ligand pair. For example, active agent accretion has reached a therapeutically or diagnostically significant level within from about 1 to about 8 hours following administration of active agent-containing conjugate. Consequently, radionuclides having appropriately short half-lives may be employed in pretargeting protocols of the present invention. In this manner, non-target toxicity is further reduced. Exemplary short half-life radionuclides include Cu-64, Cu-67, Lu-177, Rh-105, I-123, I-131, Sm-153, Re-186, Re-188, Bi-212, Pb-212, At-211, Y-90, In-111, Tc-99m and the like.

While the pretargeting protocols set forth above have been described primarily in combination with delivery of a radionuclide diagnostic or therapeutic moiety, the protocols are amenable to use for delivery of other moieties, including anti-tumor agents, chemotherapeutic drugs and the like. For example, most naturally occurring and recombinant cytokines have short in vivo half lives. This characteristic limits the clinical effectiveness of these molecules, because near toxic doses are often required. Dose-limiting toxicities in humans have been observed upon high dose IL-2 or tumor necrosis factor, gamma-interferon or lymphotoxin administrations, for example.

Anti-tumor agents, such as IL-2 and TNF, may be employed as active agents in the practice of two-step or three-step pretargeting protocols of the present invention. Some anti-tumor agents exhibit short circulation half-lives (less than about 1 hour post-administration), such as IL-2 (half-life of about 10 minutes), other interleukins, TNF, interferons and the like. Such short half-life active agents are amenable to use in pretargeting protocols of the present invention.

Anti-tumor agents having longer half-lives (ranging from about 2 hours to about 12 hours post-administration) are preferably employed at low doses, while conjugates incorporating such moieties at high doses preferably also incorporate a biodistribution directing moiety, such as a polymer, to direct the biodistribution of the conjugate and active agent-containing metabolites thereof to renal excretion. Ligand or anti-ligand derivatization of a long half-life anti-tumor agent may decrease the serum half-life sufficiently to permit higher doses of conjugate to be administered, however.

IL-2 has a molecular weight of 15,500 daltons and is formed of 133 amino acids (42% nonpolar and 58% polar). IL-2 is characterized by 12 free primary amines for reaction with a ligand or an anti-ligand (e.g., biotin or streptavidin) or with functional groups of a biodistribution directing molecule (e.g., polymer). A single disulfide Cys58–Cys105 appears essential for activity. The Cys125 residue appears not to be required for some uses and provides an additional functional group for derivatization. The three dimensional crystal structure of IL-2 has been solved to 3 angstrom resolution. Most of the secondary structure is alpha helical in nature. Three of the alpha helices (residues 11–19; residues 33–56; and residues 107–113) appear to be important for IL-2 binding and activity. Five of the twelve free amines are located in these helices, and, preferably, derivatization of IL-2 is not conducted via these amines. IL-2 is normally purified by mono-S and reverse phase high pressure liquid chromatography (RP). Elution conditions for RP (60% acetonitrile, pH 2–3) suggest a very stable or, at least, an elastic molecule. Consequently, IL-2 appears to be amenable to a number of conjugation techniques.

IL-2-biotin conjugates may be formed using biotinamidocaproate N-hydroxysuccinimide ester (commercially available from Sigma Chemical Co.). The reaction of IL-2 and biotinamidocaproate N-hydroxysuccinimde ester is conducted at room temperature for 0.5 hours in a 0.1M sodium borate buffer, pH 8.0–8.5, containing 0.1% sodium dodecyl sulfate to keep IL-2 in solution. When the IL-2 concentration is 5–10 mg/ml of reaction buffer, biotin is incorporated at 75–80% when imidate ester, dissolved in DMSO in a volume no greater than 5–10% of the total reaction volume, is added at a 2–4 biotin:IL-2 molar ratio. The product conjugate contains 1.5–3 biotins per IL-2 molecule. Biotin incorporation is assessed using the 2-(4-hydroxyazobenzene)benzoic acid (HABA displacement assay using pronase digested biotinylated IL-2.

Polymer-IL-2-biotin conjugates may be formed using commercially available biotinylated, lysine-derivatized dextran polymer (Sigma Chemical Co.) that is activated by reacting a lysine residue thereof with the bifunctional reagent SMCC, under conditions analogous to the biotinylation of IL-2 set forth above (e.g., molar ratio and the like). The SMCC-derivatized dextran polymer now contains the reactive maleimide functional group available for conjugation with the cysteine sulfhydryl moiety of IL-2 at pH 5–7 in acetate/phosphate buffer.

IL-2 receptor-bearing cells include activated T-cells, normal T-cells, activated B-cells, NK cells, LAK cells and thymocytes. High, intermediate and low affinity receptors for IL-2 exist. However, only about 10% of the receptors for IL-2 appear to be high affinity receptors ($K_d$ approximately $10^{-11}$M).

In the practice of a two-step pretargeting aspect of the present invention, IL-2 may be delivered to target cells as follows:

administering to the recipient a first conjugate comprising a targeting moiety and a member of a ligand-anti-ligand binding pair, wherein the first conjugate localizes to a target site;

optionally administering to the recipient a clearing agent capable of directing the clearance of circulating conjugate from the recipient or optionally treating the recipient with a clearing device or an alternative clearing procedure to substantially remove circulating conjugate from the recipient; and administering to the recipient a second conjugate comprising an anti-tumor agent, such as IL-2, and a ligand/anti-ligand binding pair member, wherein the second conjugate binding pair member is complementary to that of the first conjugate.

One alternative to the optional clearance step set forth above is simply to allow an amount of time to pass that is sufficient to permit the recipient's native clearance mechanisms to substantially remove circulating conjugate.

Concentrations of IL-2 effective in maintaining activated tumor infiltrating lymphocytes (TIL) and for other forms of anti-tumor therapy have also been found to be toxic to the recipient. Localization of IL-2 to the tumor microenvironment allows localized activation of effector cells to poorly immunogenic tumor antigens. Effector cells of the cytotoxic T-lymphocyte lineage and T-helper lineage are induced to recognize tumor antigens and clonally expand to seek out tumor metastases at other locations.

Furthermore, B cells may be induced to secrete antibody specifically recognizing tumor antigens. These B cells mature into IgG secretory cells and memory cells and continue to expand when tumor antigens are detected at other sites. In addition, natural killer cells are candidates for anti-tumor immunity, because such cells are also activated by IL-2. Studies in SCID-beige mice deficient in T and B cells but NK competent showed that such mice were effective hosts in rejecting an IL-2 transfected tumor cell line. See Alosco et al., *Cancer Immunol. Immunother.*, 36: 364–372, 1993.

Tumor necrosis factors (TNFs) have been isolated from a variety of mammalian species. For example, human, murine, rabbit and guinea pig exhibit at least alpha and beta forms of TNF. In humans, TNF-alpha exhibits a molecular weight of 45 (gel filtration) and 17 (SDS-PAGE), an isoelectric point of 5.6, no glycosylation, protease sensitivity, 2 cysteine residues, 157 amino acids and a terminal valine residue. TNF-beta exhibits a molecular weight of 65 (gel filtration) and 25 (SDS-PAGE), an isoelectric point of 5.8, glycosylation, protease resistance, no cysteine residues, 171 amino acids, and a terminal leucine residue. The serum half-lives of TNF-alpha and TNF-beta are approximately 10 to 15 minutes.

TNF-alpha and TNF-beta exhibit free primary amines for conjugation to the ligand biotin, for example, or to a functional group of a biodistribution directing molecule. TNF-biotin conjugates may be formed as follows: Biotinamidocaproate N-hydroxysuccinimidate (dissolved in a small volume of DMSO) is offered at a 4–8 biotin:TNF molar ratio with respect to TNF (dissolved in 0.1M borate buffer, pH 8.0–8.5, at a protein concentration of 0.5 mg/ml). After 2 hours at room temperature TNF has incorporated 1 biotin per TNF molecule as assessed by the HABA assay.

Polymer-TNF-biotin conjugates may be formed using commercially available biotinylated, lysine-derivatized dextran polymer (10 kD–70 kD glucan polymer supplied by Sigma Chemical Co.) that is reacted with N-succinimidyl-3-(2-pyridyl-dithio)propionate (SPDP), under conditions analogous to the biotinylation of TNF as described above to give rise to a pyridyl dithio-derivatized polymer. TNF is derivatized by a lysine residue thereof with the bifunctional reagent SMCC, under conditions analogous to the biotinylation of TNF set forth above to give rise to maleimidyl-derivatized TNF. To the pyridyl dithio polymer, dithiothreitol (DTT) is added in an oxygen free environment at a 2:1 DTT:polymer molar ratio to generate a free sulfhydryl moiety on the polymer. After purification of the derivatized polymer in the oxygen free environment, the maleimidyl-derivatized TNF is added, wherein the maleimidyl group reacts with the sulfhydryl moiety of the derivatized polymer to form the product conjugate.

TNF receptor-bearing cells include adipocytes, myotubes, cervical carcinoma, fetal lung, bladder carcinoma, histocytic leukemia, erthroleukemia, promyelocytic leukemia, epidermoid carcinoma, cervical carcinoma, T lymphoma, human lymphocytes, lymphoblastic leukemia (two receptors), monocytic leukemia, foreskin fibroblast, connective tissue (two receptors), murine macrophage, and bovine endothelium. High, intermediate and low affinity receptors for TNF exist.

TNF-alpha and TNF-beta have been shown to exhibit different biological effects on certain target cells, including endothelial cells (production of IL-1), myeloid cells (clonogenic survival), fibroblasts and macrophages (production of macrophage colony-stimulating factor), neutrophils (activation of neutrophils), osteoblasts (proliferation, release of $Ca^{+2}$ collagen degradation), vascular smooth muscle cells (interferon-gamma-dependent expression of human lymphocyte antigen-DR), T-cell hybridoma (MHC-I cell expression), and B lymphocytes (growth factor).

In the practice of a two-step pretargeting aspect of the present invention, TNF may be delivered to target cells essentially in the manner described above for IL-2.

TNF itself is cytotoxic to a narrow spectrum of tumor cells; however, this cytokine exhibits a broad range of immunologic modulating activities. One such activity is activation of tumor infiltrating macrophages or monocytes, thereby rendering the macrophages tumoricidal. One theory regarding the mechanism of TNF in this regard suggests that TNF stimulates monocytes to progress to macrophages which are, in turn, stimulated by TNF to release cytotoxic factors (e.g., oxidative burst or protease secretion or cytokine release). TNF release by activated macrophages can maintain or induce tumoricidal activity through an autocrine mechanism. Additional activation of monocytes or macrophages by other cytokines (e.g., gamma-interferon) may be employed to enhance the cytotoxic effect.

For example, membrane preparations from gamma-interferon-activated monocytes are cytotoxic to K562 (erythroleukemia cell line) or WEHI164 (murine fibrosarcoma cell line) target cells. Pretreatment of monocytes with recombinant TNF-alpha for 1 hour followed by treatment of medium alone or gamma-interferon led to increased killing of the aforementioned tumor cell types by the TNF-alpha/gamma-interferon-treated membrane preparations of monocytes. See, for example, Peck et al., *Cellular Immunol.*, 132: 308, 1991).

Burrows et al., *Proc. Natl. Acad. Sci. USA*, 90: 8996–9000, 1993, discuss the concept of vascular targeting. Tumor target vascular endothelial cells are accessible to circulating agents. Burrows et al. transfected a neuroblastoma cell line with the murine INF-gamma gene. These transfected cells as well as their non-transfected counterparts were grown subcutaneously in BALB/c nu/nu mice. The transfected cells secreted INF-gamma, which induced expression of class II antigens of the major histocompatibility complex by capillary and venular endothelial cells within the tumor mass. An immunotoxin targeted to such MHC class II antigens was then administered and rapid accretion to tumor and tumor regressions were observed. Relapses were observed 7–10 days after treatment and were attributed to surviving tumor cells that derived nutrition from the extratumoral blood supply.

The pretargeting approach may be employed in conducting vascular targeting diagnostic or therapeutic protocols. For example, a suitable two-step pretargeting method useful in practicing vascular targeting includes the following:

administering to the recipient a first conjugate comprising a targeting moiety specific for tumor endothelial cells and INF-gamma, wherein the first conjugate localizes to a target site and the INF-gamma induces expression of MHC class II antigens by tumor endothelial cells;

optionally administering to the recipient a clearing agent capable of directing the clearance of circulating conjugate from the recipient or optionally treating the recipient with a clearing device or an alternative clearing procedure to substantially remove circulating conjugate from the recipient; and administering to the recipient a second conjugate comprising an anti-tumor agent, such as a toxin, a radionuclide, an anti-tumor agent or the like, and a targeting agent specific for MHC class II antigens.

An alternative two-step pretargeting method useful in vascular targeting is as follows:

administering to the recipient a first conjugate comprising a targeting moiety specific for tumor endothelial cells and a member of a ligand-anti-ligand binding pair, wherein the first conjugate localizes to a target site;

optionally administering to the recipient a clearing agent capable of directing the clearance of circulating conjugate from the recipient or optionally treating the recipient with a clearing device or an alternative clearing procedure to substantially remove circulating conjugate from the recipient; and administering to the recipient a second conjugate comprising an anti-tumor agent, such as a toxin, a radionuclide or an anti-tumor agent, and a ligand/anti-ligand binding pair member, wherein the second conjugate binding pair member is complementary to that of the first conjugate. This latter protocol offers the advantages of not relying on tumor endothelial cells to express the antigen recognized by the active agent-bearing conjugate and of not exposing the recipient to systemically administered INF-gamma.

One alternative to the optional clearance step set forth above is simply to allow an amount of time to pass that is sufficient to permit the recipient's native clearance mechanisms to substantially remove circulating conjugate.

Also, an optional additional step is the administration of a conjugate incorporating a targeting moiety specific for tumor cells and a cytotoxic active agent. Alternatively, administration of a conjugate comprising a targeting moiety specific for tumor cells and the member of the ligand-anti-ligand binding pair incorporated in the first conjugate, wherein this conjugate localizes to a target site. In this manner, tumor cells that receive nutrition from the extratumoral vasculature can be addressed.

A protocol, such as administration of streptavidin-targeting moiety conjugate followed by administration of biotinylated cytokine, is also contemplated by the present invention. Such pretargeting of anti-ligand serves to improve the performance of cytokine therapeutics by increasing the amount of cytokine localized to target cells.

Streptavidin-antibody conjugates generally exhibit pharmacokinetics similar to the native antibody and localize well to target cells, depending upon their construction. Biotinylated cytokines retain a short in vivo half-life; however, cytokine may be localized to the target as a result of the affinity of biotin for avidin. In addition, biotin-avidin experience a pH-dependent dissociation which occurs at a slow rate, thereby permitting a relatively constant, sustained release of cytokine at the target site over time. Also, cytokines complexed to target cells through biotin-avidin association are available for extraction and internalization by cells involved in cellular-mediated cytotoxicity.

A pre-formed antibody-streptavidin-biotin-cytokine preparation may also be employed in the practice of these methods of the present invention. In addition, a three-step protocol of the present invention may also be employed to deliver a cytokine, such as IL-2, to a target site.

It is another object of the invention to increase the utilization of cytokine (ligand or anti-ligand) conjugates at targeted sites, e.g., a tumor. More particularly, it is an object of the invention to increase the utilization of TNF-biotin/(streptavidin or avidin)-antibody conjugate system as a delivery system for delivery of cytokines to tumor cells. This is accomplished by providing for the site specific release of biologically active, "free" cytokine, e.g., TNF at the targeted site.

This is accomplished by the administration of a complex of a targeting moiety—(ligand or anti-ligand) conjugate, and a cytokine (ligand or anti-ligand) conjugate or moieties which provide for formation of such a complex. The prototypical embodiment comprises the administration of a complex of NR-LU-10/streptavidin precomplexed with biotinylated TNF. This "premade" fusion construct is an effective means for site-specifically delivering a cytokine, e.g., TNF, to a tumor site. Moreover, it is believed that this may decrease systemic toxicity associated with TNF.

In this regard, the utilization of cytokines, including tumor necrosis factor (TNF), has been limited by both their systemic toxicity and the lack of effective targeting to desired sites of action. This application describes methods which utilize pretargeting to effect the site-specific delivery of cytokines to target sites. Another methodology which can be applied to both pretargeted (separately administered) and precomplexed (Ab-StrAv(Bt-cytokine)) should provide for the release of "free," more biologically active cytokine, e.g., TNF, at the target site, following cytokine localization at the target site by either of the aforementioned technologies. TNF is a protein synthesized and secreted by mononuclear phagocytes in response to stimulation by bacterial endotoxin and other agents. It has been shown to produce hemorrhagic necrosis of tumors in vivo. The delivery of TNF to target sites is plagued by its short half-life (11–30 min. in humans) and its toxic effects on the cardiovascular system, where hypotension is dose limiting. This hypotension is most likely a result of TNF-mediated release of nitric oxide by vascular endothelial cells, as is seen in septic shock. Pretargeting has been shown to be an effective methodology for "trapping" molecules with a relatively short serum half-life at the tumor, allowing their accretion to high concentrations within a short time. These molecules are then retained for long periods of time due to slow off-rate and/or diffusion of the antibody-streptavidin conjugate from the tumor.

Therefore, since TNF is toxic due to its effects on the vasculature, the same toxicity might be expected for biotinylated TNF (TNF-Bt) in a pretargeting approach. This could be addressed by a very slow infusion of this material, but one would potentially still be exposing the vasculature to some concentration of TNF. Accordingly, it is an object of the invention to "mask" this toxicity by precomplexing TNF-Bt with an antibody/StrAv, therefore allowing the accretion at the target to be antibody-dependent, in a pharmacokinetic sense. Assuming that this construct is less (or non-) toxic, there is a possibility that it might be less efficacious against target cells. If this is the case, to release "free", biologically active TNF-Bt at the target, one could allow TNF-Bt conjugate to accrete to peak levels at the target site, then administer systemically either biotin or a non-toxic small molecule biotinylated species which will act to disrupt the equilibrium of TNF-Bt which is coming off the Ab/StrAv, replacing the TNF-Bt as it comes off the Ab-StrAv, and allowing it to build up a concentration of "free" TNF-Bt. Since TNF is a protein of approximately 16 kD molecular weight, it should not diffuse away rapidly from the tumor, therefore allowing an effective local concentration to be achieved.

The idea for this embodiment of the invention was in vivo experimental data which demonstrated that a non-covalent conjugate of StrAv and biotinylated NR-LU-10 dissociated at a vary rapid rate (less than a day) in the presence of a high concentration of free biotin, but dissociated much more slowly in the absence of biotin. This result provided evidence that by administering a "pulse" of biotin should allow an "offloading" of a therapeutic species following target localization.

It is believed that free biotin administration should yield a corresponding increase in serum biotin levels to facilitate dissociation of free cytokine. However, assuming that enough concentrations of biotin cannot be attained by biotin administration, (because of tight in vivo biotin regulation) then administering a biotinylated species such as a small molecule, protein or polymer, with appropriate pharmacokinetics, should obviate this potential problem.

Thus, based on the foregoing, this embodiment of the invention essentially, comprises exploiting the non-covalent nature of TNF-Bt a cytokine-ligand or anti-ligand e.g.interaction at the target site, whether it was pretargeted or precomplexed, and to facilitate its release by competing it off with ligand or anti-ligand, e.g. biotin. Additional improvement of this embodiment further include the use of appropriate low-affinity analogs of the ligand or anti-ligand biotin to provide for the release of free cytokine, e.g. TNF.

Other anti-tumor agents that may be delivered in accordance with the pretargeting techniques of the present invention are selectins, including L-selectin, P-selectin and E-selectin. The presence of cytokines stimulates cells, such as endothelial cells, to express selectins on the surfaces thereof. Selectins bind to white blood cells and aid in delivering white blood cells where they are needed. Consequently, a protocol, such as administration of streptavidin- or avidin-targeting moiety conjugate followed by administration of biotinylated selectins, is also contemplated by the present invention. Such pretargeting of anti-ligand serves to improve the performance of selectin therapeutics by increasing the amount of selectin localized to target cells. In this manner, the necessity of cytokine induction of selectin expression is obviated by the localization and retention of selectin at a target cell population.

Chemotherapeutic drugs also generally exhibit short in vivo half-lives at a therapeutically effective dose. Consequently, another example of a protocol of the present invention includes administration of avidin-targeting moiety conjugate followed by administration of a biotin-chemotherapeutic drug conjugate or complex, such as a drug-carrier-biotin complex. A three-step protocol of the present invention may also be employed to deliver a chemotherapeutic drug, such as methotrexate, adriamycin, high potency adriamycin analogs, trichothecenes, potent enediynes, such as esperamycins and calicheamycins, cytoxan, vinca alkaloids, actinamycin D, taxol, taxotere or the like to a target site.

While the majority of the exemplary pretargeting protocols set forth above have been directed to the treatment of cancer, pretargeting protocols may be employed in the diagnosis or treatment of other conditions. Exemplary additional conditions are discussed below.

For example, active agents that are cytotoxic to activated cytotoxic T-cells, such as trichothecenes (e.g., Roridin A, Verrucarin A, anguidine, scirpenetriol and the like) as well as agents that decrease helper T-cell activity or helper T-cell number, such as TGF-beta, or increase Ts activity, and the like will facilitate the treatment of autoimmune diseases and transplantation rejection prevention. Tissue lesions in autoimmune disease are caused by the direct action of activated cytotoxic T-cells. Tissue transplantation is also, in part, mediated by the action of activated T-cells that bind to the cells of the new tissue and lyse them. Active agents that selectively de-activate or selectively kill activated cytotoxic T-cells can be employed as active agents in pretargeting protocols of the present invention directed at the treatment of autoimmune disease or the prevention of tissue rejection. Such active agents may also be administered in combination with a second active agent that disrupts antibody (produced by B cells with the assistance of helper T-cells and IL-2)-complement mediated cell lysis associated with graft rejection.

Targeting to the target tissues may be accomplished via antibodies directed to the IL-2 receptor such as anti-TAC, anti-IL-2 receptor antibodies (e.g., anti-P-55 receptor and anti-P-75 receptor) or by IL-2 itself or the like. IL-2 is rapidly internalized upon binding to its receptor and is otherwise primarily excreted via the renal pathway. Consequently, IL-2 would be a less desirable targeting moiety for pretargeting, as it may not remain on the surface of target cells long enough to allow completion of the protocol.

For example, delivery of active agents, such as interferon-gamma, tumor necrosis factor-alpha or a combination thereof, to monocytes or macrophages or tumor cells via pretargeting protocols will facilitate the treatment of cancer through the mechanism of activating the monocytes to cytotoxic macrophages. Activated macrophages excrete toxic moieties such as enzymes, lysozyme cathepsins and hydrolases. Tumor necrosis factor-alpha acts via activation of cytotoxic macrophages, direct tumor cell killing or rendering the tumor cells more susceptible to effector cell-mediated cytotoxicity. A combination of the two active agents serves to optimally prime macrophage tumoricidal activity. Targeting to the target tissues may be accomplished via antibodies directed to tumor specific antigens, such that the active agents are presented to the infiltrating monocyte population in a localized environment.

For example, delivery of active agents, such as interleukin-2, to cytotoxic T-cells via pretargeting protocols will facilitate the treatment of cancer through the mechanism of activating tumor infiltrating lymphocytes (TIL). Killing by cytotoxic T-cells is believed to be mediated by release of pore-forming moieties that insert into the membrane of the target cell and facilitate target cell lysis. Targeting to the target tissues may be accomplished via antibodies directed to tumor specific antigens.

For example, delivery of active agents, such as granulocyte monocyte colony stimulating factor (GM-CSF), to macrophages and polymorphonuclear neutrophils via pretargeting protocols will facilitate the treatment of cancer through the mechanism of activating infiltrating monocytes and polymorphonuclear leukocytes (PMNs). Killing by monocytes and polymorphonuclear leukocytes is the result of cytotoxic enzymes released by activated forms of these cells. Targeting to the target tissues may be accomplished via antibodies directed to tumor specific antigens.

For example, delivery of active agents, such as transforming growth factor-beta (TGF-beta), to pancreatic tissue via pretargeting protocols will facilitate the treatment of insulin-dependent diabetes mellitus through the mechanism of inhibition of cytotoxic T-cell maturation and inhibition of T-cell proliferation. Delivery to pancreatic tissue may be accomplished, for example, an antibody or other targeting moiety which recognizes an antigen present on islet cells. Killing by T-cells is the result of the release of pore-forming moieties by activated forms of these cells. Targeting to the target tissues may be accomplished via antibodies directed to the pancreas.

TGF-beta may also be employed in the treatment of inflammatory disease using pretargeting protocols of the present invention. Exemplary chronic inflammatory diseases which may be so treated are rheumatoid arthritis, thyroid disease in Hashimoto's thyroiditis, tuberculoid granuloma and the like. TGF-beta is delivered to target by an antibody or other targeting moiety which recognizes fibroblast activation protein or antigen 19 on stimulated stromal fibroblasts. See, for example, Rettig et al., *Cancer. Res.,* 53: 3327, 1993. In this manner, TGF-beta may be used to inhibit chronic inflammation by targeting stromal fibroblasts activated by peptide mediators and proteolytic enzymes.

For example, delivery of active agents, such as roridin A, verrucarin A, anguidine and like trichothecenes to RNA via pretargeting protocols will facilitate the treatment of insulin-dependent diabetes mellitus or cancer through the mechanism of protein synthesis inhibition. Targeting to the target tissues may be accomplished via antibodies directed to tumor specific antigens or to the pancreas.

An additional aspect of the present invention is directed to the use of targeting moieties that are monoclonal antibodies or fragments thereof that localize to an antigen that is recognized by the antibody NR-LU-10. Such monoclonal antibodies or fragments may be murine or of other non-human mammalian origin, chimeric, humanized or human.

NR-LU-10 is a 150 kilodalton molecular weight IgG2b monoclonal antibody that recognizes an approximately 40 kilodalton glycoprotein antigen expressed on most carcinomas. in vivo studies in mice using an antibody specific for the NR-LU-10 antigen revealed that such antibody was not rapidly internalized, which would have prevented localization of the subsequently administered active-agent-containing conjugate to the target site.

NR-LU-10 is a well characterized pancarcinoma antibody that has been safely administered to over 565 patients in human clinical trials. The hybridoma secreting NR-LU-10 was developed by fusing mouse splenocytes immunized with intact cells of a human small cell lung carcinoma with P3×63/Ag8UI murine myeloma cells. After establishing a seed lot, the hybridoma was grown via in vitro cell culture methods, purified and verified for purity and sterility.

Radioimmunoassays, immunoprecipitation and Fluorescence-Activated Cell Sorter (FACS) analysis were used to obtain reactivity profiles of NR-LU-10. The NR-LU-10 target antigen was present on either fixed cultured cells or in detergent extracts of various types of cancer cells. For example, the NR-LU-10 antigen is found in small cell lung, non-small cell lung, colon, breast, renal, ovarian, pancreatic, and other carcinoma tissues. Tumor reactivity of the NR-LU-10 antibody is set forth in Table A, while NR-LU-10 reactivity with normal tissues is set forth in Table B. The values in Table B are obtained as described below. Positive NR-LU-10 tissue reactivity indicates NR-LU-10 antigen expression by such tissues. The NR-LU-10 antigen has been further described by Varki et al., "Antigens Associated with a Human Lung Adenocarcinoma Defined by Monoclonal Antibodies," *Cancer Research,* 44: 681–687, 1984, and Okabe et al., "Monoclonal Antibodies to Surface Antigens of Small Cell Carcinoma of the Lung," *Cancer Research,* 44: 5273–5278, 1984.

The tissue specimens were scored in accordance with three reactivity parameters: (1) the intensity of the reaction; (2) the uniformity of the reaction within the cell type; and (3) the percentage of cells reactive with the antibody. These three values are combined into a single weighted comparative value between 0 and 500, with 500 being the most intense reactivity. This comparative value facilitates comparison of different tissues. Table B includes a summary reactivity value, the number of tissue samples examined and the number of samples that reacted positively with NR-LU-10.

Methods for preparing antibodies that bind to epitopes of the NR-LU-10 antigen are described in U.S. Pat. No. 5,084,396. Briefly, such antibodies may be prepared by the following procedure:

absorbing a first monoclonal antibody directed against a first epitope of a polyvalent antigen onto an inert, insoluble matrix capable of binding immunoglobulin, thereby forming an immunosorbent;

combining the immunosorbent with an extract containing polyvalent NR-LU-10 antigen, forming an insolubilized immune complex wherein the first epitope is masked by the first monoclonal antibody;

immunizing an animal with the insolubilized immune complex;

fusing spleen cells from the immunized animal to myeloma cells to form a hybridoma capable of producing a second monoclonal antibody directed against a second epitope of the polyvalent antigen;

culturing the hybridoma to produce the second monoclonal antibody; and collecting the second monoclonal antibody as a product of the hybridoma.

Consequently, monoclonal antibodies NR-LU-01, NR-LU-02 and NR-LU-03, prepared in accordance with the procedures described in the aforementioned patent, are exemplary targeting moieties useful in this aspect of the present invention.

Additional antibodies reactive with the NR-LU-10 antigen may also be prepared by standard hybridoma production and screening techniques. Any hybridoma clones so produced and identified may be further screened as described above to verify antigen and tissue reactivity.

TABLE A

TUMOR REACTIVITY OR ANTIBODY NR-LU-10

| Organ/Cell Type Tumor | # Pos/Exam | Intensity[a] Avg. | Intensity[a] Range | Percent[b] Avg. | Percent[b] Range | Uniformity[c] Avg. | Uniformity[c] Range |
|---|---|---|---|---|---|---|---|
| Pancreas Carcinoma | 6/6 | 3 | 3 | 100 | 100 | 2.3 | 2–3 |
| Prostate Carcinoma | 9/9 | 2.8 | 2–3 | 95 | 80–100 | 2 | 1–3 |
| Lung Adenocarcinoma | 8/8 | 3 | 3 | 100 | 100 | 2.2 | 1–3 |
| Lung Small Cell Carcinoma | 2/2 | 3 | 3 | 100 | 100 | 2 | 2 |
| Lung Squamous Cell Carcinoma | 8/8 | 2.3 | 2–3 | 73 | 5–100 | 1.8 | 1–3 |
| Renal Carcinoma | 8/9 | 2.2 | 2–3 | 83 | 75–100 | 1 | 1 |
| Breast Adenocarcinoma | 23/23 | 2.9 | 2–3 | 97 | 75–100 | 2.8 | 1–3 |
| Colon Carcinoma | 12/12 | 2.9 | 2–3 | 98 | 95–100 | 2.9 | 2–3 |
| Malignant Melanoma Ocular | 0/2 | 0 | 0 | 0 | 0 | 0 | 0 |
| Malignant Melanoma | 0/11 | 0 | 0 | 0 | 0 | 0 | 0 |
| Ovarian Carcinoma | 35/35 | 2.9 | 2–3 | 200 | 100 | 2.2 | 1–3 |
| Undifferentiated Carcinoma | 1/1 | 2 | 2 | 90 | 90 | 2 | 2 |
| Osteosarcoma | 1/1 | 2 | 2 | 20 | 20 | 1 | 1 |
| Synovial Sarcoma | 0/1 | 0 | 0 | 0 | 0 | 0 | 0 |
| Lymphoma | 0/2 | 0 | 0 | 0 | 0 | 0 | 0 |
| Liposarcoma | 0/2 | 0 | 0 | 0 | 0 | 0 | 0 |
| Uterine Leiomyosarcoma | 0/1 | 0 | 0 | 0 | 0 | 0 | 0 |

[a]Rated from 0–3, with 3 representing highest intensity.
[b]Percentage of cells stained within the examined tissue section.
[c]Rates from 0–3, with 3 representing highest uniformity.

TABLE B

| Organ/Cell Type | # Pos/Exam | Summary Reactivity |
|---|---|---|
| Adenoid | | |
| Epithelium | 3 | 433 |
| Lymphoid Follicle-Central | 0/3 | 0 |
| Lymphoid Follicle-Peripheral | 2/2 | 400 |
| Adipose Tissue | | |
| Fat Cells | 0/3 | 0 |
| Adrenal | | |
| Zona Fasciculata Cortex | 0/3 | 0 |
| Zona Glomerulosa Cortex | 0/3 | 0 |
| Zona Reticularis Cortex | 0/3 | 0 |
| Medulla | 0/3 | 0 |
| Aorta | | |
| Endothelium | 0/3 | 0 |
| Elastic Interna | 0/3 | 0 |
| Tunica Adventitia | 0/3 | 0 |
| Tunica Media | 0/3 | 0 |
| Brain-Cerebellum | | |
| Axons, Myelinated | 0/3 | 0 |
| Microglia | 0/3 | 0 |
| Neurons | 0/3 | 0 |
| Purkenje's Cells | 0/3 | 0 |
| Brain-Cerebrum | | |
| Axons, Myelinated | 0/3 | 0 |
| Microglia | 0/3 | 0 |
| Neurons | 0/3 | 0 |
| Brain-Midbrain | | |
| Axons, Myelinated | 0/3 | 0 |
| Microglia | 0/3 | 0 |
| Neurons | 0/3 | 0 |
| Colon | | |
| Mucosal Epithelium | 3/3 | 500 |
| Muscularis Externa | 0/3 | 0 |
| Muscularis Mucosa | 0/3 | 0 |
| Nerve Ganglia | 0/3 | 0 |
| Serosa | 0/1 | 0 |
| Duodenum | | |
| Mucosal Epithelium | 3/3 | 500 |
| Muscularis Mucosa | 0/3 | 0 |
| Epididymis | | |
| Epithelium | 3/3 | 419 |
| Smooth Muscle | 0/3 | 0 |
| Spermatozoa | 0/1 | 0 |
| Esophagus | | |
| Epithelium | 3/3 | 86 |
| Mucosal Gland | 2/2 | 450 |
| Smooth Muscle | 0/3 | 0 |
| Gall Bladder | | |
| Mucosal Epithelium | 0/3 | 467 |
| Smooth Muscle | 0/3 | 0 |
| Heart | | |
| Myocardium | 0/3 | 0 |
| Serosa | 0/1 | 0 |
| Ileum | | |

TABLE B-continued

| Organ/Cell Type | # Pos/Exam | Summary Reactivity |
|---|---|---|
| Lymph Node | 0/2 | 0 |
| Mucosal Epithelium | 0/2 | 0 |
| Muscularis Externa | 0/1 | 0 |
| Muscularis Mucosa | 0/2 | 0 |
| Nerve Ganglia | 0/1 | 0 |
| Serosa | 0/1 | 0 |
| Jejunum | | |
| Lymph Node | 0/1 | 0 |
| Mucosal Epithelium | 2/2 | 400 |
| Muscularis Externa | 0/2 | 0 |
| Muscularis Mucosa | 0/2 | 0 |
| Nerve Ganglia | 0/2 | 0 |
| Serosa | 0/1 | 0 |
| Kidney | | |
| Collecting Tubules | 2/3 | 160 |
| Distal Convoluted Tubules | 3/3 | 500 |
| Glomerular Eipthelium | 0/3 | 0 |
| Mesangial | 0/3 | 0 |
| Proximal Convoluted Tubules | 3/3 | 500 |
| Liver | | |
| Bile Duct | 3/3 | 500 |
| Central Lobular Hepatocyte | 1/3 | 4 |
| Periportal Hepatocyte | 1/3 | 40 |
| Kupffer Cells | 0/3 | 0 |
| Lung | | |
| Alveolar Macrophage | 0/3 | 0 |
| Bronchial Epithelium | 0/2 | 0 |
| Bronchial Smooth Muscle | 0/2 | 0 |
| Pneumocyte Type I | 3/3 | 354 |
| Pneumocyte Type II | 3/3 | 387 |
| Lymph Node | | |
| Lymphoid Follicle-Central | 0/3 | 0 |
| Lymphoid Follicle-Peripheral | 0/3 | 0 |
| Mammary Gland | | |
| Alveolar Epithelium | 3/3 | 500 |
| Duct Epithelium | 3/3 | 500 |
| Myoepithelium | 0/3 | 0 |
| Muscle Skeletal | | |
| Muscle Fiber | 0/3 | 0 |
| Nerve | | |
| Axon, Myelinated | 0/2 | 0 |
| Endoneurium | 0/2 | 0 |
| Neurolemma | 0/2 | 0 |
| Neuron | 0/2 | 0 |
| Perineurium | 0/2 | 0 |
| Ovary | | |
| Corpus Luteum | 0/3 | 0 |
| Eipthelium | 1/1 | 270 |
| Granulosa | 1/3 | 400 |
| Serosa | 0/3 | 0 |
| Theca | 0/3 | 0 |
| Oviduct | | |
| Epithelium | 1/1 | 500 |
| Smooth Muscle | 0/3 | 0 |
| Pancreas | | |
| Acinar Cell | 3/3 | 500 |
| Duct Epthelium | 3/3 | 500 |
| Islet Cell | 3/3 | 500 |
| Peritoneum | | |
| Mesothelium | 0/1 | 0 |
| Pituitary | | |
| Adenohypophysis | 2/2 | 500 |
| Neurohypophysis | 0/2 | 0 |
| Placenta | | |
| Trophoblasts | 0/3 | 0 |
| Prostate | | |
| Concretions | 0/3 | 0 |
| Glandular Epithelium | 3/3 | 400 |
| Smooth Muscle | 0/3 | 0 |
| Rectum | | |
| Lymph Node | 0/2 | 0 |
| Mucosal Epithelium | 0/2 | 0 |
| Muscularis Externa | 0/1 | 0 |
| Muscularis Mucosa | 0/3 | 0 |
| Nerve Ganglia | 0/3 | 0 |
| Salivary Gland | | |
| Acinar Epithelium | 3/3 | 500 |
| Duct Epithelium | 3/3 | 500 |
| Skin | | |
| Apocrine Glands | 3/3 | 280 |
| Basal Layer | 3/3 | 33 |
| Epithelium | 1/3 | 10 |
| Follicle | 1/1 | 190 |
| Stratum Corneum | 0/3 | 0 |
| Spinal Cord | | |
| Axons, Myelinated | 0/2 | 0 |
| Microglial | 0/2 | 0 |
| Neurons | 0/2 | 0 |
| Spleen | | |
| Lymphoid Follicle-Central | 0/3 | 0 |
| Lymphoid Follicle-Peripheral | 0/3 | 0 |
| Trabecular Smooth Muscle | 0/3 | 0 |
| Stomach | | |
| Chief Cells | 3/3 | 290 |
| Mucosal Epithelium | 3/3 | 367 |
| Muscularis Mucosa/Externa | 0/3 | 0 |
| Parietal Cells | 3/3 | 290 |
| Smooth Muscle | 0/3 | 0 |
| Stromal Tissue | | |
| Adipose | 0/63 | 0 |
| Arteriolar Smooth Muscle | 0/120 | 0 |
| Endothelium | 0/120 | 0 |
| Fibrous Connective Tissue | 0/120 | 0 |
| Macrophages | 0/117 | 0 |
| Mast Cells/Eosinophils | 0/86 | 0 |
| Testis | | |
| Interstitial Cells | 0/3 | 0 |
| Sertoli Cells | 3/3 | 93 |
| Thymus | | |
| Hassal's Epithelium | 3/3 | 147 |
| Hassal's Keratin | 3/3 | 333 |
| Lymphoid Cortex | 0/3 | 0 |
| Lymphoid Medulla | 3/3 | 167 |
| Thyroid | | |
| C-Cells | 0/3 | 0 |
| Colloid | 0/3 | 0 |
| Follicular Epithelium | 3/3 | 500 |
| Tonsil | | |
| Epithelium | 1/3 | 500 |
| Lymphoid Follicle-Central | 0/3 | 0 |
| Lymphoid Follicle-Peripheral | 0/3 | 0 |
| Mucus Gland | 1/1 | 300 |
| Striated Muscle | 0/3 | 0 |
| Umbilical Cord | | |
| Epithelium | 0/3 | 0 |
| Urinary Bladder | | |

TABLE B-continued

| Organ/Cell Type | # Pos/Exam | Summary Reactivity |
| --- | --- | --- |
| Mucosal Epithelium | 3/3 | 433 |
| Serosa | 0/1 | 0 |
| Smooth Muscle | 0/3 | 0 |
| Uterus | | |
| Endometrial Epithelium | 3/3 | 500 |
| Endometrial Glands | 3/3 | 500 |
| Smooth Muscle | 0/3 | 0 |
| Vagina/Cervix | | |
| Epithelial Glands | 1/1 | 500 |
| Smooth Muscle | 0/2 | 0 |
| Squamous Epithelium | 1/1 | 200 |

It is another object of the present invention to produce novel biotin-chelate conjugates for use in pretargeting which contain a metastable linkage between the ligand and the chelate portion of the molecule.

Previous experiments have been conducted in house to identify ligands which, as radioimmunoconjugates, display superior properties to ligands already evaluated in clinical trials ($N_2S_2$, $N_3S$, MAGG-GABA) with respect to minimizing intestinal uptake. These experiments demonstrated that ligands, when radiolabeled and conjugated to antibodies and fragments thereof through lysine residues, exhibited less than optimal localization to the intestines. This was believed to be the result of ligand-lysine adducts produced through catabolic breakdown of the ligand-Ab conjugate in the liver. In an effort to decrease intestinal activity, as well as to enhance kidney clearance, it was decided to incorporate an ester linkage between the ligand and the antibody molecule. The antibody conjugate would then be expected to catabolize to release a small molecule which can be excreted through the kidney (as it would be lacking the lysine residue). To test this hypothesis, s-ethoxyethylmercaptoacetylglycyl-glycylseryl-o-succinyl-tetrafluorophenyl ester (1) was synthesized, radiolabeled (2) and conjugated to NR-LU-10 Fab (3).

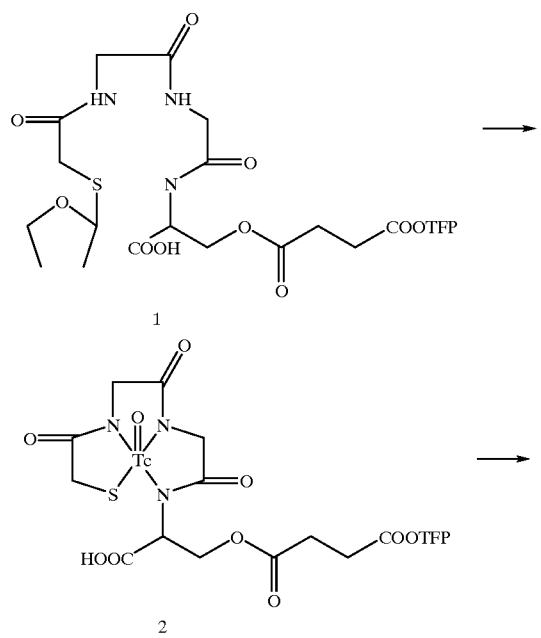

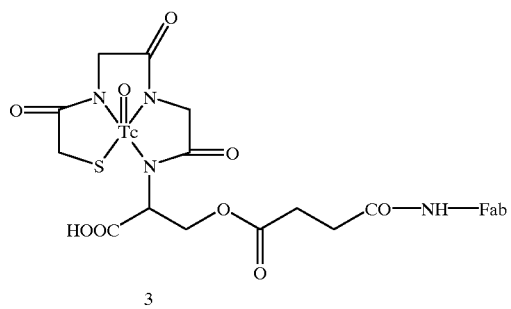

As predicted, in the rat model, the conjugate (3) showed approximately 50% reduction of radioactivity in the intestines and 60% in the kidneys. The conjugate (3) exhibited similar biodistribution in tumor bearing mice for tumor uptake and radiolabel clearance from the blood compared to the many other conjugates suggesting that the serylsuccinate linkage is serum stable.

By contrast, conjugation studies of labeled ligand (2) indicate that the resulting conjugate (3) is much less stable at basic pH (8.3–9.5) than at pH 7.5 (7.0–7.5 is physiologic). This instability is believed to be due to greater chemical instability of the serylsuccinate ester linkage at basic pH over stability at pH approaching neutrality.

Though the use of the NR-LU-10-streptavidin conjugate and Y-DOTA-biotin in therapeutic pretargeting methods affords numerous intrinsic benefits, over conventional RIT as it still suffers from one noteworthy disadvantage. Specifically, the NR-LU-10-streptavidin conjugate when used as the primary targeting vehicle followed, eventually, by the stable Y-DOTA-biotin chelate results in less than optimal levels of radiolabel at the kidneys. This is believed to be the result of cross-reactivity of the conjugate to antigen expressed at the collecting tubules. As a result of this cross-reactivity, introduction of biotinylated ligand results in binding to the streptavidin pretargeted to this site as well as to tumor.

Therefore, this embodiment of the present invention will minimize or alleviate exposure of the kidneys to the radiolabeled chelate by the use of ligands which possess a metastable linkage between the biotin portion of the ligand and the chelate portion. For example, a linkage may be incorporated which is stable under normal physiological conditions, but is labile under site specific alteration of these conditions. In this regard, it is known that the pH of the urine, to which the renal collecting tubules are exposed, may be elevated to 8.5 using intravenously administered bicarbonate solution without significantly altering the serum pH. Therefor, applying such a protocol to elevate urine pH, a ligand which incorporates a base labile linkage should initially bind to renally targeted conjugate, but then release the radiolabeled chelate portion upon chemical cleavage of the linkage (as opposed to metabolic cleavage) when the conjugate is exposed to the basic urine environment. One such ligand is illustrated below.

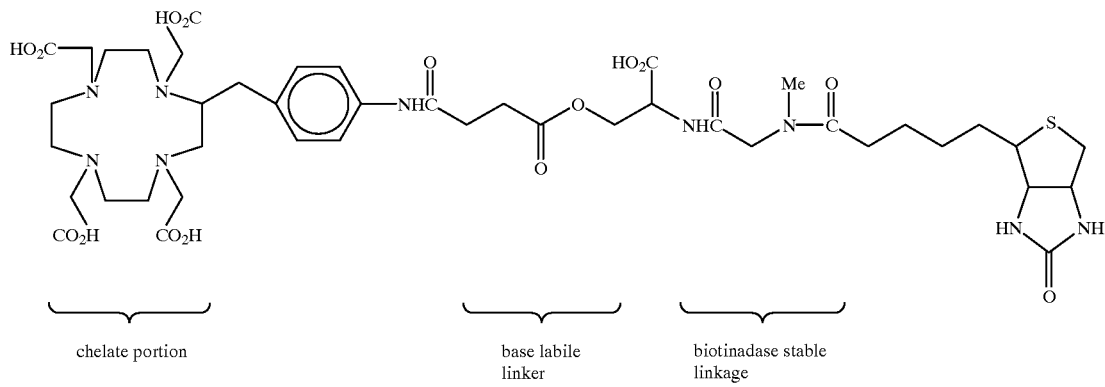

| chelate portion | base labile linker | biotinadase stable linkage |

The ligand incorporates a DOTA macrocycle to stably bind the radioisotope, a biotinadase stabilizing linkage (the N-methyl amide linkage) and a base labile linkage, the serylsuccinate ester. A proposed synthesis of this ligand is illustrated below. Proposed synthetic route to Biotinamido-N-Methylglycl-Seryl-O-Succinamido-Benzyl-DOTA (9).

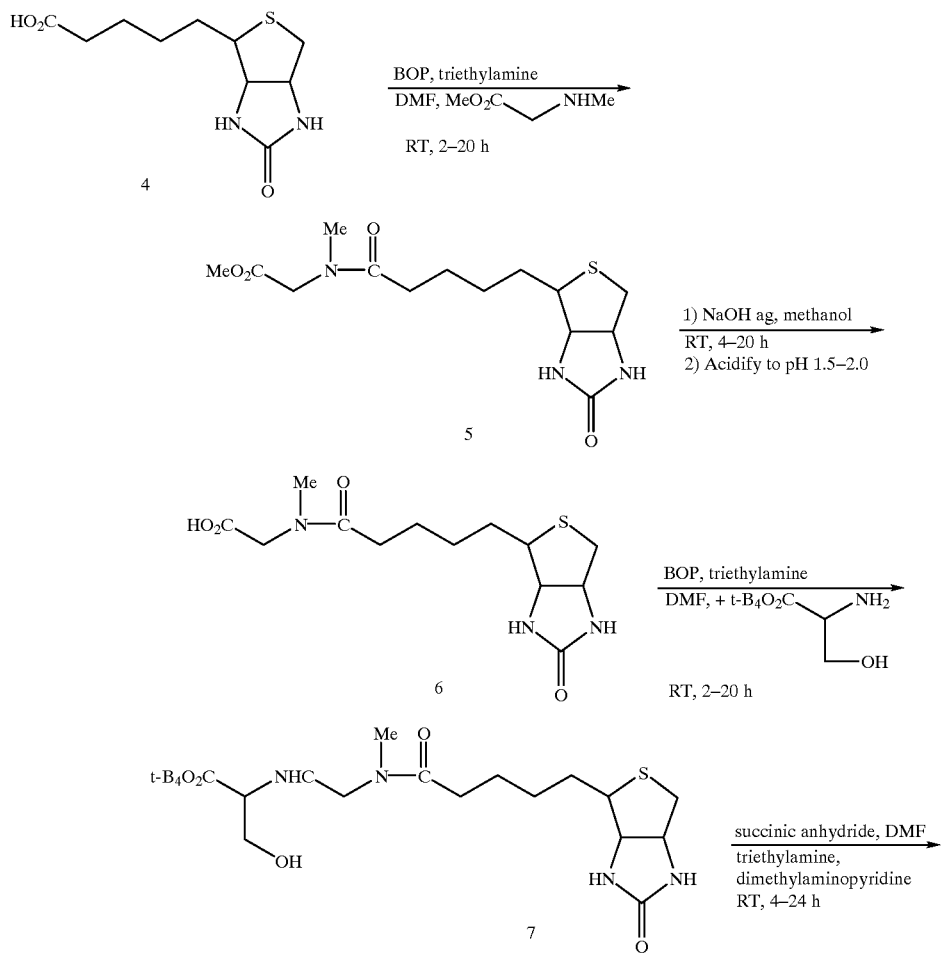

-continued

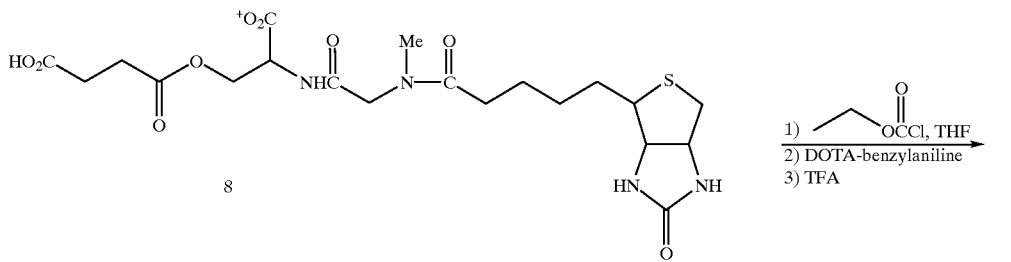

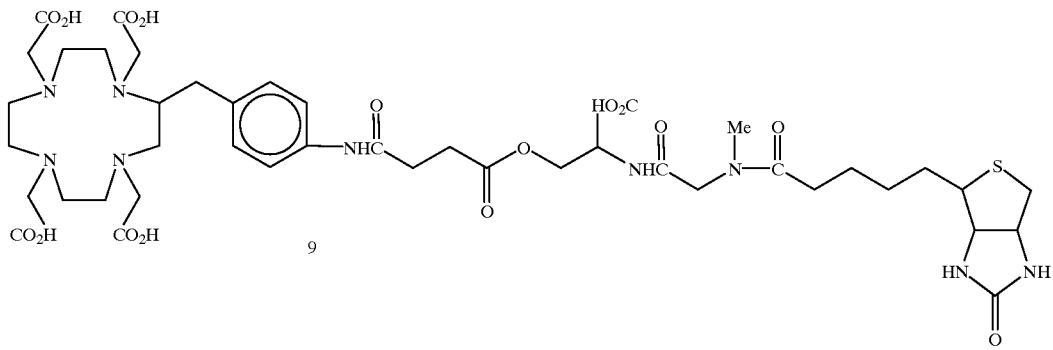

It is another object of the present invention to produce therapeutic conjugates containing radioactive chelates and biotin, wherein the chelate and biotin moieties are separated by a cleavable linker. A problem with pretargeted RIT is the accumulation of radioactivity in normal tissue. The ideal carrier should, by itself, have excellent renal excretion.

Cleavable linkers are advantageous because they should reduce the absorbed dose delivered to the kidney and/or gut. Essentially, this comprises selection of a conjugate which is serum stable, but which provides for enhanced renal and intestinal excretion of radioactive catabolites. Potential compounds with cleavable linkers include, e.g., set the compounds forth in the Table below.

| | Rxn. Temp (° C.) | Rxn. Time (min) | Re(V)/ (VII) | Others | Ester |
|---|---|---|---|---|---|
| $N_3S$-Adipate | 75 | 30 | 4% | 16% | 80% |
| $N_3S$-1-Seryl-succinate | 75 | 30 | 1% | 23% | 76% |
| $N_3S$-2-Seryl-succinate | 75 | 30 | 14% | 49% | 37% |
| $N_3S$-3-Seryl-succinate | 75 | 30 | 10% | 26% | 64% |
| $N_3S$-Amino-Ethanol | 95 | 30 | <1% | 87% | 13% |
| $N_3S$-Amino-Ethanol | 75 | 30 | 12% | 67% | 21% |

For example, when tested, the $N_3S$-3-Seryl-succinate (3-55) provided for good overall radiochemical yield and biodistribution of its Techenitium NR-LU-10 Fab conjugate.

To be efficacious, the ligand ideally should be storage stable. This can be determined by one skilled in the art. For example, this can be effected by incubating a radiolabelled conjugate in vitro in various challenging solutions at 37° C. Commonly used challenging solutions include fresh serum, 50 mg/ml HSA, 5 mg/ml Diethylenetetramine pentacetric acid (DTPA) at pH 7.5 and 10 mm cysteine at pH 7.5.

To alleviate the delivery of radioactivity to pretargeted Ab-StAv on normal tissues, it may be desirable to have a cleavable linkage between the radioactive chelate and biotin. This requires the selection of a linker that is selectively cleaved in normal tissue, but not in tumors. There has been substantial investigation in this area. Ester linkages have been reported to give higher tumor to blood ratios (See, Haseman, M. K. et al., *Eur. J. Nucl. Med.*, Metabolizable In-III chelate conjugated anti-idiotype monoclonal antibody for radioimmunodetection of lymphoma in mice, 12: 455–60 (1986); Gestin, J. F., et al., *Nuclear Med. Biol*; Introduction of Five Potentially Metabolizable Linking Groups Between In-III Cyclohexyl EDTA Derivatives and F(ab')$_2$ Fragments of Anti-Carcinoambryonic Antigen Antibody—I. A New Reproducible Method, 20(6): 755–62 (1993); Mark Hylarides et al., Bioconjugate Chemistry on PIP Ester-linked Fab Conjugates; and Kasina, S., et al., The Third Conference on Radioimmunodetection and Radioimmunotherapy of Cancer, Princeton, N.J., 1990). The ester linked MAG$_3$ Fab' conjugate 1, shown below, reportedly gave a two-fold improvement in clearance from the kidney compared to the amide linked conjugate (Weber, R. W., *Biocon;. Chem.*, Enhanced kidney clearance with an ester-linked $^{99}$TC-radiolabeled antibody Fab'-chelator conjugate, 1, 431–437 (1990)).

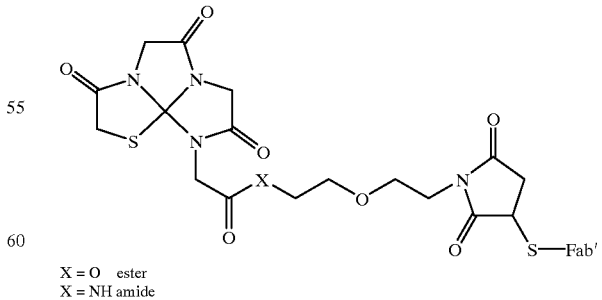

X = O ester
X = NH amide

Therefore, it is believed that the following ester linked biotin DOTA conjugates should provide for improved normal tissue excretion.

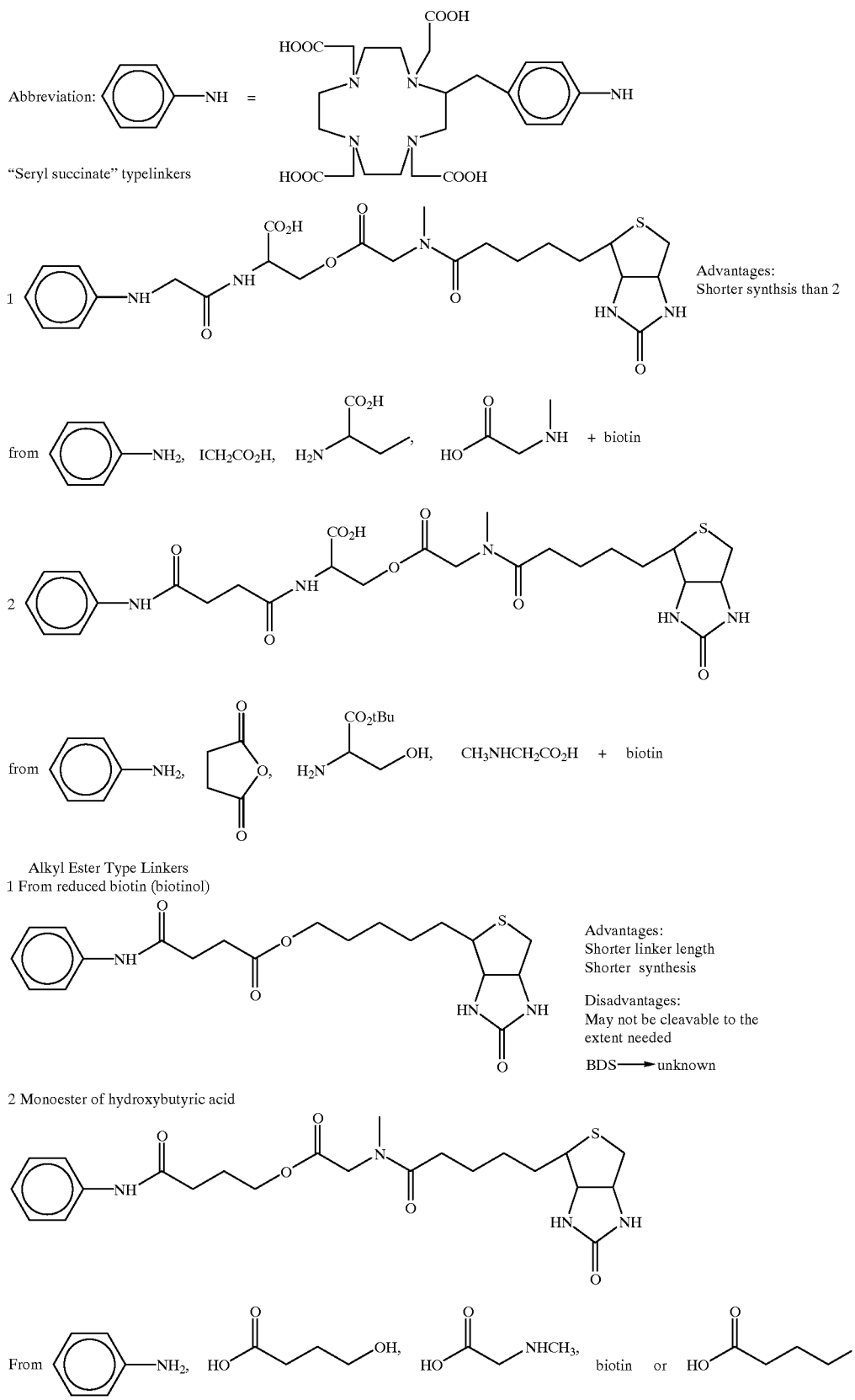

3 Diester of hydroxybutyric acid

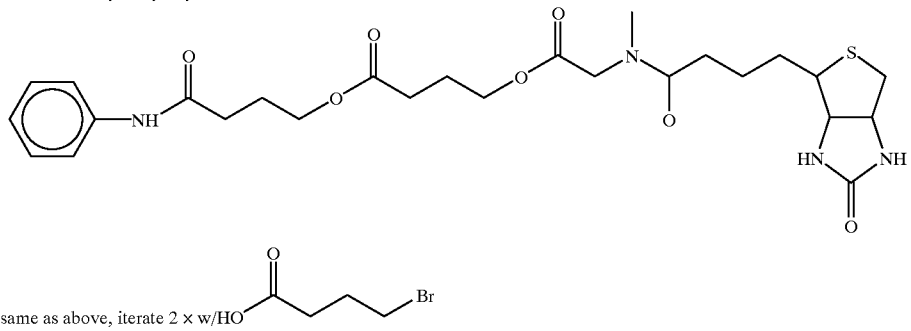

same as above, iterate 2 × w/HO

With respect to these linkers, the first "seryl succinate" liker is advantageous in that it comprises a relatively short synthesis procedure. Of the alkyl ester type linkers, it is further noted that the biotinol linker is advantageous in the fact that the linker is relatively short and synthesis should be fairly routine. The ordinary skilled artisan can synthesize linkers such as depicted above and determine those which exhibit optimal properties, i.e., release rate. It should be noted that these structures are only representative of cleavable ester linkages which can be constructed to provide for improved normal tissue excretion. The invention embraces any cleavable ester linked biotin DOTA conjugate which upon vivo administration provides for satisfactory delivery of radioactive material to targeted tissue and tolerable levels of toxicity to normal tissues. Synthesis of the above-identified linkers can be effected by the ordinary skilled artisan using known synthesis techniques.

The invention is further described through presentation of the following examples. These examples are offered by way of illustration, and not by way of limitation.

EXAMPLE I

Synthesis of a Chelate-Biotin Conjugate

A chelating compound that contains an $N_3S$ chelating core was attached via an amide linkage to biotin. Radiometal labeling of an exemplary chelate-biotin conjugate is illustrated below.

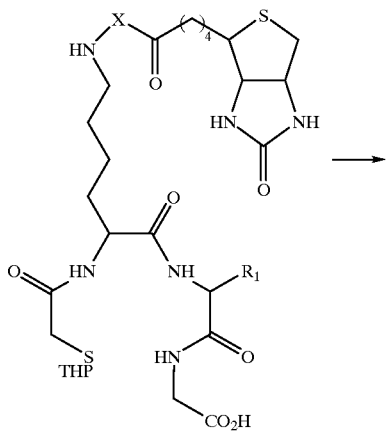

X = $(CH_2)_0$, short chain
X = $CO(CH_2)_5NH$, long chain
$R^1$ = H or $CH_2CO_2H$

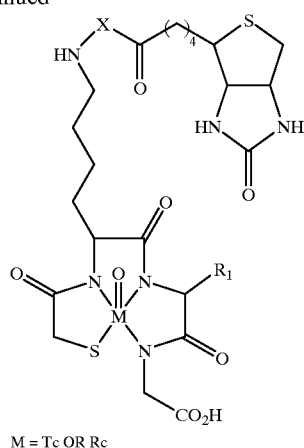

M = Tc OR Rc

The spacer group "X" permits the biotin portion of the conjugate to be sterically available for avidin binding. When "$R^1$" is a carboxylic acid substituent (for instance, $CH_2COOH$), the conjugate exhibits improved water solubility, and further directs in vivo excretion of the radiolabeled biotin conjugate toward renal rather than hepatobiliary clearance.

Briefly, N-α-Cbz-N-Σ-t-BOC protected lysine was converted to the succinimidyl ester with NHS and DCC, and then condensed with aspartic acid β—t-butyl ester. The resultant dipeptide was activated with NHS and DCC, and then condensed with glycine t-butyl ester. The Cbz group was removed by hydrogenolysis, and the amine was acylated using tetrahydropyranyl mercaptoacetic acid succinimidyl ester, yielding S-(tetrahydropyranyl)-mercaptoacetyl-lysine. Trifluoroacetic acid cleavage of the N-t-BOC group and t-butyl esters, followed by condensation with LC-biotin-NHS ester provided (Σ-caproylamide biotin)-aspartyl glycine. This synthetic method is illustrated below.

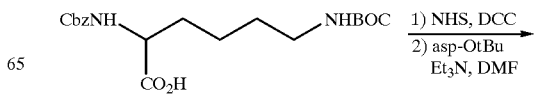

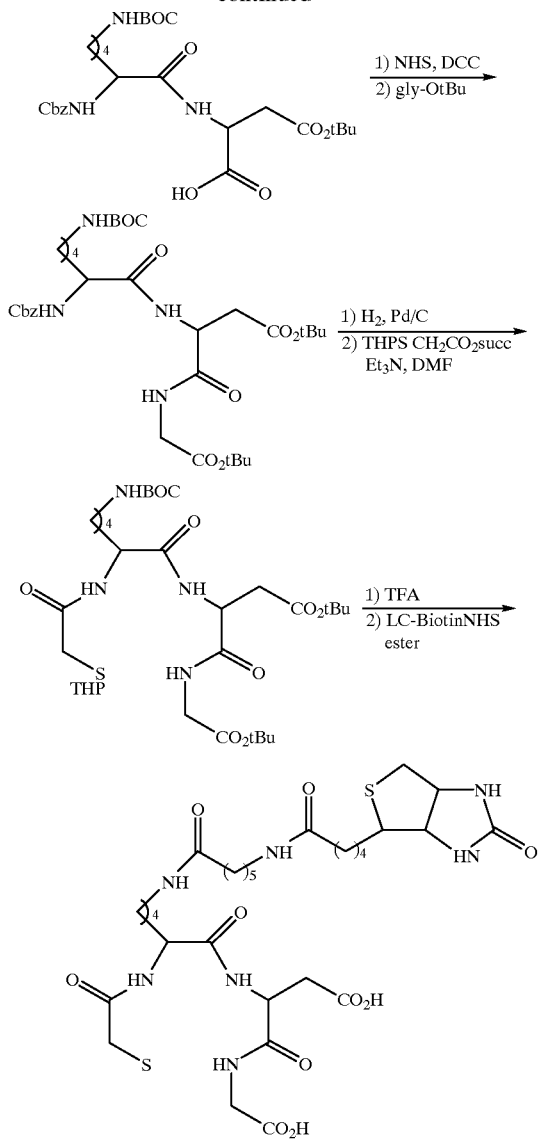

¹H NMR: (CD₃OD, 200 MHz Varian) : 1.25–1.95 (m, 24H), 2.15–2.25 (broad t, 4H), 2.65–3.05 (m, 4H), 3.30–3.45 (dd, 2H), 3.50–3.65 (ddd, 2H), 3.95 (broad s, 2H), 4.00–4.15 (m, 1H), 4.25–4.35 (m, 1H), 4.45–4.55 (m, 1H), 4.7–5.05 (m overlapping with HOD).

Elemental Analysis: C, H, N for $C_{35}H_{57}N_7O_{11}S_2 \cdot H_2O$ calculated: 50.41, 7.13, 11.76 found: 50.13, 7.14, 11.40

EXAMPLE II

Preparation of a Technetium or Rhenium Radiolabeled Chelate-Biotin Conjugate The chelate-biotin conjugate of Example I was radiolabeled with either $^{99m}$Tc pertechnetate or $^{186}$Re perrhenate. Briefly, $^{99m}$Tc pertechnetate was reduced with stannous chloride in the presence of sodium gluconate to form an intermediate Tc-gluconate complex. The chelate-biotin conjugate of Example I was added and heated to 100° C. for 10 min at a pH of about 1.8 to about 3.3. The solution was neutralized to a pH of about 6 to about 8, and yielded an N₃S-coordinated $^{99m}$Tc-chelate-biotin conjugate. C-18 HPLC gradient elution using 5–60% acetonitrile in 1% acetic acid demonstrated two anomers at 97% or greater radiochemical yield using δ (gamma ray) detection.

Alternatively, $^{186}$Re perrhenate was spiked with cold ammonium perrhenate, reduced with stannous chloride, and complexed with citrate. The chelate-biotin conjugate of Example I was added and heated to 90° C. for 30 min at a pH of about 2 to 3. The solution was neutralized to a pH of about 6 to about 8, and yielded an N₃S-coordinated $^{186}$Re-chelate-biotin conjugate. C-18 HPLC gradient elution using 5–60% acetonitrile in 1% acetic acid resulted in radiochemical yields of 85–90%. Subsequent purification over a C-18 reverse phase hydrophobic column yielded material of 99% purity.

EXAMPLE III

In vitro Analysis of Radiolabeled Chelate-Biotin Conjugates

Both the $^{99m}$Tc- and $^{186}$Re-chelate-biotin conjugates were evaluated in vitro. When combined with excess avidin (about 100-fold molar excess), 100%- of both radiolabeled biotin conjugates complexed with avidin.

A $^{99m}$Tc-biotin conjugate was subjected to various chemical challenge conditions. Briefly, $^{99m}$Tc-chelate-biotin conjugates were combined with avidin and passed over a 5 cm size exclusion gel filtration column. The radiolabeled biotin-avidin complexes were subjected to various chemical challenges (see Table 1), and the incubation mixtures were centrifuged through a size exclusion filter. The percent of radioactivity retained (indicating avidin-biotin-associated radiolabel) is presented in Table 1. Thus, upon chemical challenge, the radiometal remained associated with the macromolecular complex.

TABLE 1

| Chemical Challenge of $^{99m}$Tc-Chelate-Biotin-Avidin Complexes | | | |
|---|---|---|---|
| Challenge | | % Radioactivity Retained | |
| Medium | pH | 1 h, 37° C. | 18 h, RT |
| PBS | 7.2 | 99 | 99 |
| Phosphate | 8.0 | 97 | 97 |
| 10 mM cysteine | 8.0 | 92 | 95 |
| 10 mM DTPA | 8.0 | 99 | 98 |
| 0.2M carbonate | 10.0 | 97 | 94 |

In addition, each radiolabeled biotin conjugate was incubated at about 50 μg/ml with serum; upon completion of the incubation, the samples were subjected to instant thin layer chromatography (ITLC) in 80% methanol. Only 2–4% of the radioactivity remained at the origin (i.e., associated with protein); this percentage was unaffected by the addition of exogenous biotin. When the samples were analyzed using size exclusion H-12 FPLC with 0.2 M phosphate as mobile phase, no association of radioactivity with serum macromolecules was observed.

Each radiolabeled biotin conjugate was further examined using a competitive biotin binding assay. Briefly, solutions containing varying ratios of D-biotin to radiolabeled biotin conjugate were combined with limiting avidin at a constant total biotin:avidin ratio. Avidin binding of each radiolabeled biotin conjugate was determined by ITLC, and was compared to the theoretical maximum stoichiometric binding (as determined by the HABA spectrophotometric assay of Green, *Biochem. J.* 94: 23c–24c, 1965). No significant difference in avidin binding was observed between each radiolabeled biotin conjugate and D-biotin.

EXAMPLE IV

In vivo Analysis of Radiolabeled Chelate-Biotin Conjugates Administered After Antibody Pretargeting The $^{186}$Re-chelate-biotin conjugate of Example I was studied in an animal model of a three-step antibody pretargeting protocol. Generally, this protocol involved: (i) prelocalization of biotinylated monoclonal antibody; (ii) administration of avidin for formation of a "sandwich" at the target site and for clearance of residual circulating biotinylated antibody; and (iii) administration of the 186Re-biotin conjugate for target site localization and rapid blood clearance.

A. Preparation and Characterization of Biotinylated Antibody

Biotinylated NR-LU-10 was prepared according to either of the following procedures. The first procedure involved derivitization of antibody via lysine ε-amino groups. NR-LU-10 was radioiodinated at tyrosines using chloramine T and either $^{125}$I or $^{131}$I sodium iodide. The radioiodinated antibody (5–10 mg/ml) was then biotinylated using biotinamido caproate NHS ester in carbonate buffer, pH 8.5, containing 5% DMSO, according to the scheme below.

TABLE 2

Effect of Lysine Biotinylation on Immunoreactivity

| Molar Offering | Measured Derivitization | Immunoassessment (%) | |
|---|---|---|---|
| (Biotins/Ab) | (Biotins/Ab) | ELISA | Cell Binding |
| 5:1 | 3.4 | 86 | |
| 10:1 | 8.5 | 73 | 100 |
| 13:1 | 11.1 | 69 | 102 |
| 20:1 | 13.4 | 36 | 106 |
| 40:1 | 23.1 | 27 | |

Alternatively, NR-LU-10 was biotinylated using thiol groups generated by reduction of cystines. Derivitization of thiol groups was hypothesized to be less compromising to antibody immunoreactivity. NR-LU-10 was radioiodinated using p-aryltin phenylate NHS ester (PIP-NHS) and either $^{125}$I or $^{131}$I sodium iodide. Radioiodinated NR-LU-10 was incubated with 25 mM dithiothreitol and purified using size exclusion chromatography. The reduced antibody (containing free thiol groups) was then reacted with a 10- to 100-fold molar excess of N-iodoacetyl-n'-biotinyl hexylene diamine in phosphate-buffered saline (PBS), pH 7.5, containing 5% DMSO (v/v).

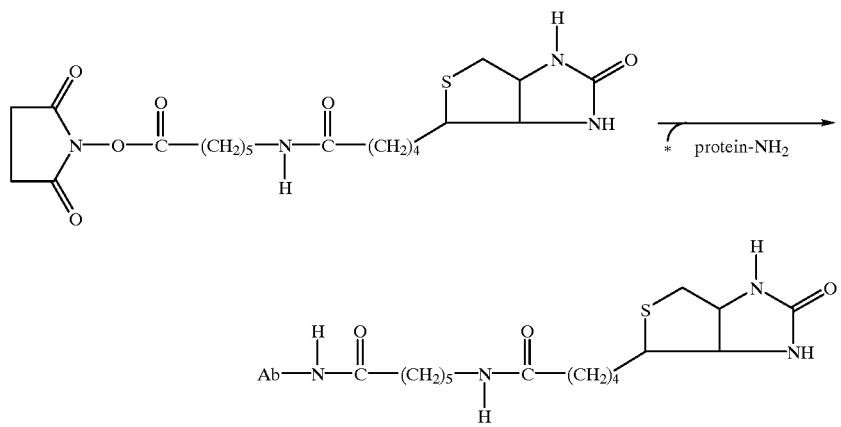

The impact of lysine biotinylation on antibody immunoreactivity was examined. As the molar offering of biotin:antibody increased from 5:1 to 40:1, biotin incorporation increased as expected (measured using the HABA assay and pronase-digested product) (Table 2, below). Percent of biotinylated antibody immunoreactivity as compared to native antibody was assessed in a limiting antigen ELISA assay. The immunoreactivity percentage dropped below 70% at a measured derivitization of 11.1:1; however, at this level of derivitization, no decrease was observed in antigen-positive cell binding (performed with LS-180 tumor cells at antigen excess). Subsequent experiments used antibody derivatized at a biotin:antibody ratio of 10:1.

TABLE 3

Effect of Thiol Biotinylation on Immunoreactivity

| Molar Offering | Measured Derivitization | Immunoassessment (%) | |
|---|---|---|---|
| (Biotins/Ab) | (Biotins/Ab) | ELISA | Cell Binding |
| 10:1 | 4.7 | 114 | |
| 50:1 | 6.5 | 102 | 100 |
| 100:1 | 6.1 | 95 | 100 |

As shown in Table 3, at a 50:1 or greater biotin:antibody molar offering, only 6 biotins per antibody were incorporated. No significant impact on immunoreactivity was observed.

The lysine- and thiol-derivatized biotinylated antibodies ("antibody (lysine)" and "antibody (thiol)", respectively) were compared. Molecular sizing on size exclusion FPLC demonstrated that both biotinylation protocols yielded monomolecular (monomeric) IgGs. Biotinylated antibody (lysine) had an apparent molecular weight of 160 kD, while biotinylated antibody (thiol) had an apparent molecular weight of 180 kD. Reduction of endogenous sulfhydryls (i.e., disulfides) to thiol groups, followed by conjugation with biotin, may produce a somewhat unfolded macromolecule. If so, the antibody (thiol) may display a larger hydrodynamic radius and exhibit an apparent increase in molecular weight by chromatographic analysis. Both biotinylated antibody species exhibited 98% specific binding to immobilized avidin-agarose.

Further comparison of the biotinylated antibody species was performed using non-reducing SDS-PAGE, using a 4% stacking gel and a 5% resolving gel. Biotinylated samples were either radiolabeled or unlabeled and were combined with either radiolabeled or unlabeled avidin or streptavidin. Samples were not boiled prior to SDS-PAGE analysis. The native antibody and biotinylated antibody (lysine) showed similar migrations; the biotinylated antibody (thiol) produced two species in the 50–75 kD range. These species may represent two thiol-capped species. Under these SDS-PAGE conditions, radiolabeled streptavidin migrates as a 60 kD tetramer. When 400 µg/ml radiolabeled streptavidin was combined with 50 µg/ml biotinylated antibody (analogous to "sandwiching" conditions in vivo), both antibody species formed large molecular weight complexes. However, only the biotinylated antibody (thiol)-streptavidin complex moved from the stacking gel into the resolving gel, indicating a decreased molecular weight as compared to the biotinylated antibody (lysine)-streptavidin complex.

B. Blood Clearance of Biotinylated Antibody Species

Radioiodinated biotinylated NR-LU-10 (lysine or thiol) was intravenously administered to non-tumored nude mice at a dose of 100 µg. At 24 h post-administration of radioiodinated biotinylated NR-LU-10, mice were intravenously injected with either saline or 400 µg of avidin. With saline administration, blood clearances for both biotinylated antibody species were biphasic and similar to the clearance of native NR-LU-10 antibody.

In the animals that received avidin intravenously at 24 h, the biotinylated antibody (lysine) was cleared (to a level of 5% of injected dose) within 15 min of avidin administration (avidin:biotin =10:1). With the biotinylated antibody (thiol), avidin administration (10:1 or 25:1) reduced the circulating antibody level to about 35% of injected dose after two hours. Residual radiolabeled antibody activity in the circulation after avidin administration was examined in vitro using immobilized biotin. This analysis revealed that 85% of the biotinylated antibody was complexed with avidin. These data suggest that the biotinylated antibody (thiol)-avidin complexes that were formed were insufficiently crosslinked to be cleared by the RES.

Blood clearance and biodistribution studies of biotinylated antibody (lysine) 2 h post-avidin or post-saline administration were performed. Avidin administration significantly reduced the level of biotinylated antibody in the blood (see FIG. 1), and increased the level of biotinylated antibody in the liver and spleen. Kidney levels of biotinylated antibody were similar.

EXAMPLE V

In vivo Characterization of $^{186}$Re-Chelate-Biotin Conjugates In a Three-Step Pretargeting Protocol A $^{186}$Re-chelate-biotin conjugate of Example I (MW≈1000; specific activity =1–2 mCi/mg) was examined in a three-step pretargeting protocol in an animal model. More specifically, 18–22 g female nude mice were implanted subcutaneously with LS-180 human colon tumor xenografts, yielding 100–200 mg tumors within 10 days of implantation.

NR-LU-10 antibody (MW≈150 kD) was radiolabeled with $^{125}$I/Chloramine T and biotinylated via lysine residues (as described in Example IV.A, above). Avidin (MW≈66 kD) was radiolabeled with $^{131}$I/PIP-NHS (as described for radioiodination of NR-LU-10 in Example IV.A., above). The experimental protocol was as follows:

| Group 1: | Time 0, inject 100 µg $^{125}$I-labeled, biotinylated NR-LU-10 |
| --- | --- |
| | Time 24 h, inject 400 µg $^{131}$I-labeled avidin |
| | Time 26 h, inject 60 µg $^{186}$Re-chelate-biotin conjugate |
| Group 2: (control) | Time 0, inject 400 µg $^{131}$I-labeled avidin |
| | Time 2 h, inject 60 µg $^{186}$Re-chelate-biotin conjugate |
| Group 3: (control) | Time 0, inject 60 µg $^{186}$Re-chelate-biotin conjugate |

The three radiolabels employed in this protocol are capable of detection in the presence of each other. It is also noteworthy that the sizes of the three elements involved are logarithmically different—antibody≡150,000; avidin≡66,000; and biotin≈1,000. Biodistribution analyses were performed at 2, 6, 24, 72 and 120 h after administration of the $^{186}$Re-chelate-biotin conjugate.

Certain preliminary studies were performed in the animal model prior to analyzing the $^{186}$Re-chelate-biotin conjugate in a three-step pretargeting protocol. First, the effect of biotinylated antibody on blood clearance of avidin was examined. These experiments showed that the rate and extent of avidin clearance was similar in the presence or absence of biotinylated antibody. Second, the effect of biotinylated antibody and avidin on blood clearance of the $^{186}$Re-chelate-biotin conjugate was examined; blood clearance was similar in the presence or absence of biotinylated antibody and avidin. Further, antibody immunoreactivity was found to be uncompromised by biotinylation at the level tested.

Third, tumor uptake of biotinylated antibody administered at time 0 or of avidin administered at time 24 h was examined. The results of this experimentation are shown in FIG. 1. At 25 h, about 350 pmol/g biotinylated antibody was present at the tumor; at 32 h the level was about 300 pmol/g; at 48 h, about 200 pmol/g; and at 120 h, about 100 pmol/g. Avidin uptake at the same time points was about 250, 150, 50 and 0 pmol/g, respectively. From the same experiment, tumor to blood ratios were determined for biotinylated antibody and for avidin. From 32 h to 120 h, the ratios of tumor to blood were very similar. Rapid and efficient removal of biotinylated antibody from the blood by complexation with avidin was observed. Within two hours of avidin administration, a 10-fold reduction in blood pool antibody concentration was noted (FIG. 1), resulting in a sharp increase in tumor to blood ratios. Avidin is cleared rapidly, with greater than 90% of the injected dose cleared from the blood within 1 hour after administration. The Re-186-biotin chelate is also very rapidly cleared, with greater than 99% of the injected dose cleared from the blood by 1 hour after administration.

The three-step pretargeting protocol (described for Group 1, above) was then examined. More specifically, tumor uptake of the $^{186}$Re-chelate-biotin conjugate in the presence or absence of biotinylated antibody and avidin was determined. In the absence of biotinylated antibody and avidin, the $^{186}$Re-chelate-biotin conjugate displayed a slight peak 2 h post-injection, which was substantially cleared from the tumor by about 5 h. In contrast, at 2 h post-injection in the presence of biotinylated antibody and avidin (specific), the $^{186}$Re-chelate-biotin conjugate reached a peak in tumor approximately 7 times greater than that observed in the absence of biotinylated antibody and avidin. Further, the specifically bound $^{186}$Re-chelate-biotin conjugate was retained at the tumor at significant levels for more than 50 h. Tumor to blood ratios determined in the same experiment increased significantly over time (i.e., T:B=≈8 at 30 h; ≈15 at 100 h; ≈35 at 140 h).

Tumor uptake of the $^{186}$Re-chelate-biotin conjugate has further been shown to be dependent on the dose of biotinylated antibody administered. At 0 µg of biotinylated antibody, about 200 pmol/g of $^{186}$Re-chelate-biotin conjugate was present at the tumor at 2 h after administration; at 50 µg antibody, about 500 pmol/g of $^{186}$Re-chelate-biotin conjugate; and at 100 µg antibody, about 1,300 pmol/g of $^{186}$Re-chelate-biotin conjugate.

Figure 2:
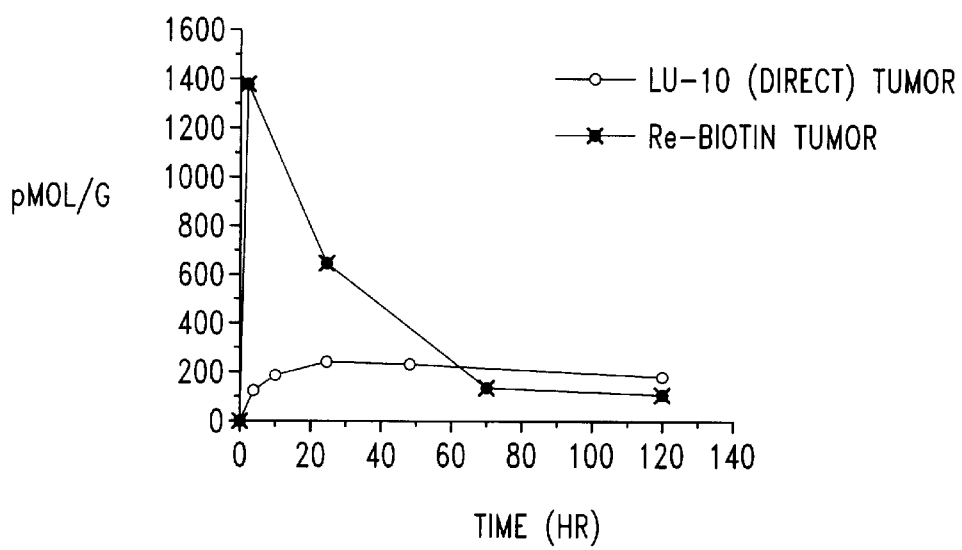
FIG. 2 depicts radiorhenium tumor uptake in a three-step pretargeting protocol, as compared to administration of radiolabeled antibody (conventional means involving antibody that is covalently linked to chelated radiorhenium).

Rhenium tumor uptake via the three-step pretargeting protocol was compared to tumor uptake of the same antibody radiolabeled through chelate covalently attached to the antibody (conventional procedure). The results of this comparison are depicted in FIG. 2. Blood clearance and tumor uptake were compared for the chelate directly labeled rhenium antibody conjugate and for the three-step pretargeted sandwich. Areas under the curves (AUC) and the ratio of $AUC_{tumor}/AUC_{blood}$ were determined. For the chelate directly labeled rhenium antibody conjugate, the ratio of $AUC_{tumor}/AUC_{blood}$=24055/10235 or 2.35; for the three-step pretargeted sandwich, the ratio of $AUC_{tumor}/AUC_{blood}$= 46764/6555 or 7.13.

Tumor uptake results are best taken in context with radioactivity exposure to the blood compartment, which directly correlates with bone marrow exposure. Despite the fact that 100-fold more rhenium was administered to animals in the three-step protocol, the very rapid clearance of the small molecule (Re-186-biotin) from the blood minimizes the exposure to Re-186 given in this manner. In the same matched antibody dose format, direct labeled (conventional procedure) NR-LU-10 whole antibody yielded greater exposure to rhenium than did the 100-fold higher dose given in the three-step protocol. A clear increase in the targeting ratio (tumor exposure to radioactivity:blood exposure to radioactivity—$AUC_{tumor}$:$AUC_{blood}$) was observed for three-step pretargeting (approximately 7:1) in comparison to the direct labeled antibody approach (approximately 2.4:1).

EXAMPLE VI

Preparation of Chelate-Biotin Conjugates Having Improved Biodistribution Properties The biodistribution of $^{111}$In-labeled-biotin derivatives varies greatly with structural changes in the chelate and the conjugating group. Similar structural changes may affect the biodistribution of technetium- and rhenium-biotin conjugates. Accordingly, methods for preparing technetium- and rhenium-biotin conjugates having optimal clearance from normal tissue are advantageous.

A. Neutral MAMA Chelate/Conjugate

A neutral MAMA chelate-biotin conjugate is prepared according to the following scheme.

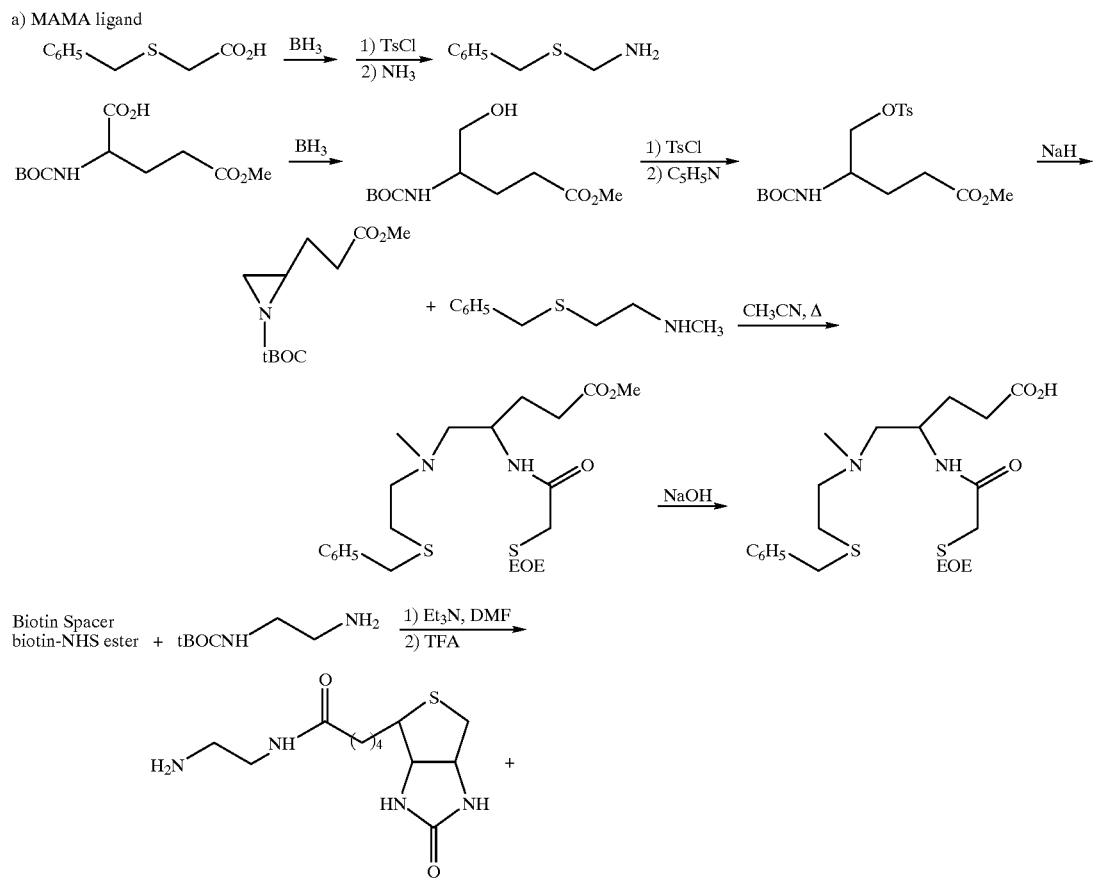

a) MAMA ligand

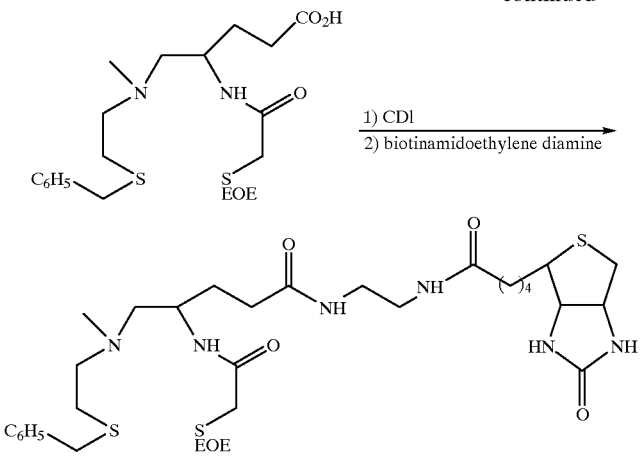

The resultant chelate-biotin conjugate shows superior kidney excretion. Although the net overall charge of the conjugate is neutral, the polycarboxylate nature of the molecule generates regions of hydrophilicity and hydrophobicity. By altering the number and nature of the carboxylate groups within the conjugate, excretion may be shifted from kidney to gastrointestinal routes. For instance, neutral compounds are generally cleared by the kidneys; anionic compounds are generally cleared through the GI system.

B. Polylysine Derivitization

Conjugates containing polylysine may also exhibit beneficial biodistribution properties. With whole antibodies, derivitization with polylysine may skew the biodistribution of conjugate toward liver uptake. In contrast, derivitization of Fab fragments with polylysine results in lower levels of both liver and kidney uptake; blood clearance of these conjugates is similar to that of Fab covalently linked to chelate. An exemplary polylysine derivatized chelate-biotin conjugate is illustrated below.

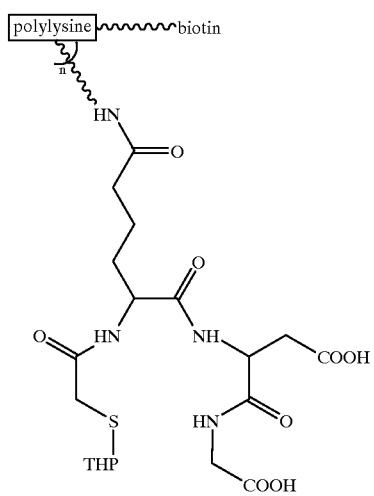

Inclusion of polylysine in radiometal-chelate-biotin conjugates is therefore useful for minimizing or eliminating RES sequestration while maintaining good liver and kidney clearance of the conjugate. For improved renal excretion properties, polylysine derivatives are preferably succinylated following biotinylation. Polylysine derivatives offer the further advantages of: (1) increasing the specific activity of the radiometal-chelate-biotin conjugate; (2) permitting control of rate and route of blood clearance by varying the molecular weight of the polylysine polymer; and (3) increasing the circulation half-life of the conjugate for optimal tumor interaction.

Polylysine derivitization is accomplished by standard methodologies. Briefly, poly-L-lysine is acylated according to standard amino group acylation procedures (aqueous bicarbonate buffer, pH 8, added biotin-NHS ester, followed by chelate NHS ester). Alternative methodology involves anhydrous conditions using nitrophenyl esters in DMSO and triethyl amine. The resultant conjugates are characterized by UV and NMR spectra.

The number of biotins attached to polylysine is determined by the HABA assay. Spectrophotometric titration is used to assess the extent of amino group derivitization. The radiometal-chelate-biotin conjugate is characterized by size exclusion.

C. Cleavable Linkage

Through insertion of a cleavable linker between the chelate and biotin portion of a radiometal-chelate-biotin conjugate, retention of the conjugate at the tumor relative to normal tissue may be enhanced. More specifically, linkers that are cleaved by enzymes present in normal tissue but deficient or absent in tumor tissue can increase tumor retention. As an example, the kidney has high levels of γ-glutamyl transferase; other normal tissues exhibit in vivo cleavage of γ-glutamyl prodrugs. In contrast, tumors are generally deficient in enzyme peptidases. The glutamyl-denked biotin conjugate depicted below is cleaved in normal tissue and retained in the tumor.

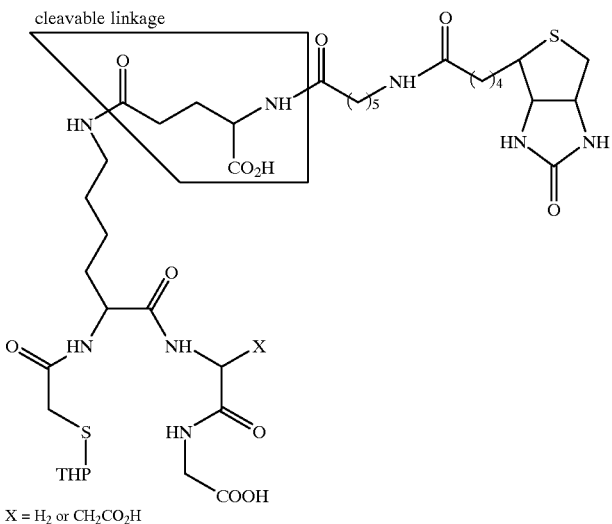

X = H₂ or CH₂CO₂H

D. Serine Linker With O-Polar Substituent

Sugar substitution of N₃S chelates renders such chelates water soluble. Sulfonates, which are fully ionized at physiological pH, improve water solubility of the chelate-biotin conjugate depicted below.

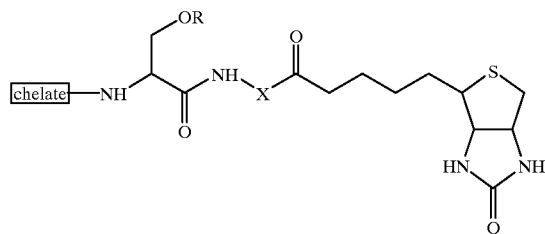

R = a sugar such as ribose or glucose or SO₂OH
X = (CH₂)₀ or CO(CH₂)₄

This compound is synthesized according to the standard reaction procedures. Briefly, biocytin is condensed with N-t-BOC-(O-sulfonate or O-glucose) serine NHS ester to give N-t-BOC-(O-sulfonate or O-glucose) serine biocytinamide. Subsequent cleavage of the N-t-BOC group with TFA and condensation with ligand NHS ester in DMF with triethylamine provides ligand- amidoserine(O-sulfonate or O-glucose)biocytinamide.

EXAMPLE VII

Preparation and Characterization of PIP-Radioiodinated Biotin

Radioiodinated biotin derivatives prepared by exposure of poly-L-lysine to excess NHS-LC-biotin and then to Bolton-Hunter N-hydroxysuccinimide esters in DMSO has been reported. After purification, this product was radiolabeled by the iodogen method (see, for instance, Del Rosario et al., *J. Nucl. Med.* 32: 5, 1991, 993 (abstr.)). Because of the high molecular weight of the resultant radioiodinated biotin derivative, only limited characterization of product (i.e., radio-HPLC and binding to immobilized streptavidin) was possible.

Preparation of radioiodinated biotin according to the present invention provides certain advantages. First, the radioiodobiotin derivative is a low molecular weight compound that is amenable to complete chemical characterization. Second, the disclosed methods for preparation involve a single step and eliminate the need for a purification step.

Briefly, iodobenzamide derivatives corresponding to biocytin (R=COOH) and biotinamidopentylamine (R=H) were prepared according to the following scheme. In this scheme, "X" may be any radiohalogen, including $^{125}$I, $^{131}$I, $^{123}$I, $^{211}$At and the like.

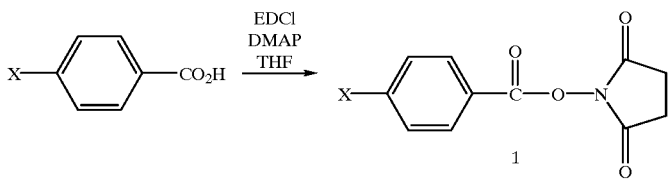

1

-continued

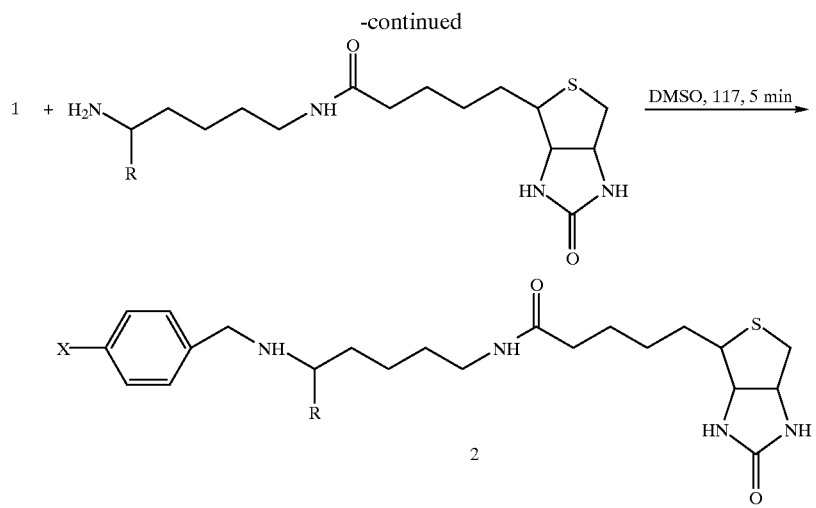

Preparation of 1 was generally according to Wilbur et al., *J. Nucl. Med.* 30: 216–26, 1989, using a tributyltin intermediate. Water soluble carbodiimide was used in the above-depicted reaction, since the NHS ester 1 formed intractable mixtures with DCU. The NHS ester was not compatible with chromatography; it was insoluble in organic and aqueous solvents and did not react with biocytin in DMF or in buffered aqueous acetonitrile. The reaction between 1 and biocytin or 5-(biotinamido) pentylamine was sensitive to base. When the reaction of 1 and biocytin or the pentylamine was performed in the presence of triethylamine in hot DMSO, formation of more than one biotinylated product resulted. In contrast, the reaction was extremely clean and complete when a suspension of 1 and biocytin (4 mg/ml) or the pentylamine (4 mg/ml) was heated in DMSO at 117° C. for about 5 to about 10 min. The resultant $^{125}$I-biotin derivatives were obtained in 94% radiochemical yield. Optionally, the radioiodinated products may be purified using C-18 HPLC and a reverse phase hydrophobic column. Hereinafter, the resultant radioiodinated products 2 are referred to as PIP-biocytin (R=COOH) and PIP-pentylamine (R=H).

Both iodobiotin derivatives 2 exhibited ≧95% binding to immobilized avidin. Incubation of the products 2 with mouse serum resulted in no loss of the ability of 2 to bind to immobilized avidin. Biodistribution studies of 2 in male BALB/c mice showed rapid clearance from the blood (similar to $^{186}$Re-chelate-biotin conjugates described above). The radioiodobiotin 2 had decreased hepatobiliary excretion as compared to the $^{186}$Re-chelate-biotin conjugate; urinary excretion was increased as compared to the $^{186}$Re-chelate-biotin conjugate. Analysis of urinary metabolites of 2 indicated deiodination and cleavage of the biotin amide bond; the metabolites showed no binding to immobilized avidin. In contrast, metabolites of the $^{186}$Re-chelate-biotin conjugate appear to be excreted in urine as intact biotin conjugates. Intestinal uptake of 2 is <50% that of the $^{186}$Re-chelate-biotin conjugate. These biodistribution properties of 2 provided enhanced whole body clearance of radioisotope and indicate the advantageous use of 2 within pretargeting protocols.

$^{131}$I-PIP-biocytin was evaluated in a two-step pretargeting procedure in tumor-bearing mice. Briefly, female nude mice were injected subcutaneously with LS-180 tumor cells; after 7 d, the mice displayed 50–100 mg tumor xenografts. At t=0, the mice were injected with 200 μg of NR-LU-10-streptavidin conjugate labeled with $^{125}$I using PIP-NHS (see Example IV.A.). At t=36 h, the mice received 42 μg of $^{131}$I-PIP-biocytin. The data showed immediate, specific tumor localization, corresponding to ≈1.5 $^{131}$I-PIP-biocytin molecules per avidin molecule.

The described radiohalogenated biotin compounds are amenable to the same types of modifications described in Example VI above for $^{186}$Re-chelate-biotin conjugates. In particular, the following PIP-polylysine-biotin molecule is made by trace labeling polylysine with $^{125}$I-PIP, followed by extensive biotinylation of the polylysine.

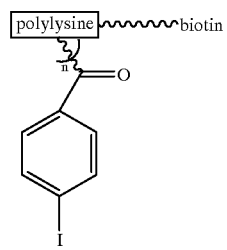

Assessment of $^{125}$I binding to immobilized avidin ensures that all radioiodinated species also contain at least an equivalent of biotin.

EXAMPLE VIII

Preparation of Biotinylated Antibody (Thiol) Through Endogenous Antibody Sulfhydryl Groups or Sulfhydryl-Generating Compounds Certain antibodies have available for reaction endogenous sulfhydryl groups. If the antibody to be biotinylated contains endogenous sulfhydryl groups, such antibody is reacted with N-iodoacetyl-n'-biotinyl hexylene diamine (as described in Example IV.A., above). The availability of one or more endogenous sulfhydryl groups obviates the need to expose the antibody to a reducing agent, such as DTT, which can have other detrimental effects on the biotinylated antibody.

Alternatively, one or more sulfhydryl groups are attached to a targeting moiety through the use of chemical compounds or linkers that contain a terminal sulfhydryl group. An exemplary compound for this purpose is iminothiolane. As with endogenous sulfhydryl groups (discussed above), the detrimental effects of reducing agents on antibody are thereby avoided.

EXAMPLE IX

Two-Step Pretargeting Methodology That Does Not Induce Internalization

A NR-LU-13-avidin conjugate is prepared as follows. Initially, avidin is derivatized with N-succinimidyl 4-(N-maleimidomethyl)cyclohexane-1-carboxylate (SMCC). SMCC-derived avidin is then incubated with NR-LU-13 in a 1:1 molar ratio at pH 8.5 for 16 h. Unreacted NR-LU-13 and SMCC-derived avidin are removed from the mixture using preparative size exclusion HPLC. Two conjugates are obtained as products—the desired 1:1 NR-LU-13-avidin conjugate as the major product; and an incompletely characterized component as the minor product.

A $^{99m}$Tc-chelate-biotin conjugate is prepared as in Example II, above. The NR-LU-13-avidin conjugate is administered to a recipient and allowed to clear from the circulation. One of ordinary skill in the art of radioimmunoscintigraphy is readily able to determine the optimal time for NR-LU-13-avidin conjugate tumor localization and clearance from the circulation. At such time, the $^{99m}$Tc-chelate-biotin conjugate is administered to the recipient. Because the $^{99m}$Tc-chelate-biotin conjugate has a molecular weight of ≈1,000 crosslinking of NR-LU-13-avidin molecules on the surface of the tumor cells is dramatically reduced or eliminated. As a result, the $^{99m}$Tc diagnostic agent is retained at the tumor cell surface for an extended period of time.

Accordingly, detection of the diagnostic agent by imaging techniques is optimized; further, a lower dose of radioisotope provides an image comparable to that resulting from the typical three-step pretargeting protocol.

Optionally, clearance of NR-LU-13-avidin from the circulation may be accelerated by plasmapheresis in combination with a biotin affinity column. Through use of such column, circulating NR-LU-13-avidin will be retained extracorporeally, and the recipient's immune system exposure to a large, proteinaceous immunogen (i.e., avidin) is minimized.

Exemplary methodology for plasmapheresis/column purification useful in the practice of the present invention is discussed in the context of reducing radiolabeled antibody titer in imaging and in treating tumor target sites in U.S. Pat. No. 5,078,673. Briefly, for the purposes of the present invention, an example of an extracorporeal clearance methodology may include the following steps:

administering a ligand- or anti-ligand-targeting moiety conjugate to a recipient;

after a time sufficient for localization of the administered conjugate to the target site, withdrawing blood from the recipient by, for example, plasmapheresis;

separating cellular element from said blood to produce a serum fraction and returning the cellular elements to the recipient; and reducing the titer of the administered conjugate in the serum fraction to produce purified serum;

infusing the purified serum back into the recipient.

Clearance of NR-LU-13-avidin is also facilitated by administration of a particulate-type clearing agent (e.g., a polymeric particle having a plurality of biotin molecules bound thereto). Such a particulate clearing agent preferably constitutes a biodegradable polymeric carrier having a plurality of biotin molecules bound thereto. Particulate clearing agents of the present invention exhibit the capability of binding to circulating administered conjugate and removing that conjugate from the recipient. Particulate clearing agents of this aspect of the present invention may be of any configuration suitable for this purpose. Preferred particulate clearing agents exhibit one or more of the following characteristics:

microparticulate (e.g., from about 0.5 micrometers to about 100 micrometers in diameter, with from about 0.5 to about 2 micrometers more preferred), free flowing powder structure;

biodegradable structure designed to biodegrade over a period of time between from about 3 to about 180 days, with from about 10 to about 21 days more preferred, or non-biodegradable structure;

biocompatible with the recipients physiology over the course of distribution, metabolism and excretion of the clearing agent, more preferably including biocompatible biodegradation products;

and capability to bind with one or more circulating conjugates to facilitate the elimination or removal thereof from the recipient through one or more binding moieties (preferably, the complementary member of the ligand/anti-ligand pair). The total molar binding capacity of the particulate clearing agents depends upon the particle size selected and the ligand or anti-ligand substitution ratio. The binding moieties are capable of coupling to the surface structure of the particulate dosage form through covalent or non-covalent modalities as set forth herein to provide accessible ligand or anti-ligand for binding to its previously administered circulating binding pair member.

Preferable particulate clearing agents of the present invention are biodegradable or non-biodegradable microparticulates. More preferably, the particulate clearing agents are formed of a polymer containing matrix that biodegrades by random, nonenzymatic, hydrolytic scissioning.

Polymers derived from the condensation of alpha hydroxycarboxylic acids and related lactones are more preferred for use in the present invention. A particularly preferred moiety is formed of a mixture of thermoplastic polyesters (e.g., polylactide or polyglycolide) or a copolymer of lactide and glycolide components, such as poly (lactide-co-glycolide). An exemplary structure, a random poly(DL-lactide-co-glycolide), is shown below, with the values of x and y being manipulable by a practitioner in the art to achieve desirable microparticulate properties.

$$H \left[ O-CH(CH_3)-\overset{O}{\underset{\|}{C}}-O-CH(CH_3)-\overset{O}{\underset{\|}{C}} \right]_x \left[ O-CH_2-\overset{O}{\underset{\|}{C}}-O-CH_2-\overset{O}{\underset{\|}{C}} \right]_y OH$$

Other agents suitable for forming particulate clearing agents of the present invention include polyorthoesters and polyacetals (*Polymer Letters,* 18: 293, 1980) and polyorthocarbonates (U.S. Pat. No. 4,093,709) and the like.

Preferred lactic acid/glycolic acid polymer containing matrix particulates of the present invention are prepared by emulsion-based processes, that constitute modified solvent extraction processes such as those described by Cowsar et al., "Poly(Lactide-Co-Glycolide) Microcapsules for Controlled Release of Steroids," *Methods Enzymology,* 112: 101–116, 1985 (steroid entrapment in microparticulates); Eldridge et al., "Biodegradable and Biocompatible Poly (DL-Lactide-Co-Glycolide) Microspheres as an Adjuvant for Staphylococcal Enterotoxin B Toxoid Which Enhances the Level of Toxin-Neutralizing Antibodies," *Infection and Immunity,* 59: 2978–2986, 1991 (toxoid entrapment); Cohen et al., "Controlled Delivery Systems for Proteins Based on Poly(Lactic/Glycolic Acid) Microspheres," *Pharmaceutical Research,* 8(6): 713–720, 1991 (enzyme entrapment); and Sanders et al., "Controlled Release of a Luteinizing Hormone-Releasing Hormone Analogue from Poly(D,L-Lactide-Co-Glycolide) Microspheres," *J. Pharmaceutical Science,* 73(9): 1294–1297, 1984 (peptide entrapment).

In general, the procedure for forming particulate clearing agents of the present invention involves dissolving the polymer in a halogenated hydrocarbon solvent and adding an additional agent that acts as a solvent for the halogenated hydrocarbon solvent but not for the polymer. The polymer precipitates out from the polymer-halogenated hydrocarbon solution. Following particulate formation, they are washed and hardened with an organic solvent. Water washing and aqueous non-ionic surfactant washing steps follow, prior to drying at room temperature under vacuum.

For biocompatibility purposes, particulate clearing agents are sterilized prior to packaging, storage or administration. Sterilization may be conducted in any convenient manner therefor. For example, the particulates can be irradiated with gamma radiation, provided that exposure to such radiation does not adversely impact the structure or function of the binding moiety attached thereto. If the binding moiety is so adversely impacted, the particulate clearing agents can be produced under sterile conditions.

The preferred lactide/glycolide structure is biocompatible with the mammalian physiological environment. Also, these preferred sustained release dosage forms have the advantage that biodegradation thereof forms lactic acid and glycolic acid, both normal metabolic products of mammals.

Functional groups required for binding moiety—particulate bonding, are optionally included in the particulate structure, along with the non-degradable or biodegradable polymeric units. Functional groups that are exploitable for this purpose include those that are reactive with ligands or anti-ligands, such as carboxyl groups, amine groups, sulfhydryl groups and the like. Preferred binding enhancement moieties include the terminal carboxyl groups of the preferred (lactide-glycolide) polymer containing matrix or the like. A practitioner in the art is capable of selecting appropriate functional groups and monitoring conjugation reactions involving those functional groups.

Advantages garnered through the use of particulate clearing agents of the type described above are as follows:

particles in the "micron" size range localize in the RES and liver, with galactose derivatization or charge modification enhancement methods for this capability available, and, preferably, are designed to remain in circulation for a time sufficient to perform the clearance function;

the size of the particulates facilitates central vascular compartment retention thereof, substantially precluding equilibration into the peripheral or extravascular compartment;

desired substituents for ligand or anti-ligand binding to the particulates can be introduced into the polymeric structure;

ligand- or anti-ligand-particulate linkages having desired properties (e.g., serum biotinidase resistance thereby reducing the release of biotin metabolite from a particle-biotin clearing agent) and multiple ligands or anti-ligands can be bound to the particles to achieve optimal cross-linking of circulating targeting agent-ligand or -anti-ligand conjugate and efficient clearance of cross-linked species. This advantage is best achieved when care is taken to prevent particulate aggregation both in storage and upon in vivo administration.

Clearance of NR-LU-13-avidin may also be accelerated by an arterially inserted proteinaceous or polymeric multi-loop device. A catheter-like device, consisting of thin loops of synthetic polymer or protein fibers derivatized with biotin, is inserted into a major artery (e.g., femoral artery) to capture NR-LU-13-avidin. Since the total blood volume passes through a major artery every 70 seconds, the in situ clearing device is effective to reduce circulating NR-LU-13-avidin within a short period of time. This device offers the advantages that NR-LU-13-avidin is not processed through the RES; removal of NR-LU-13-avidin is controllable and measurable; and fresh devices with undiminished binding capacity are insertable as necessary. This methodology is also useful with intraarterial administration embodiments of the present invention.

An alternative procedure for clearing NR-LU-13-avidin from the circulation without induction of internalization involves administration of biotinylated, high molecular weight molecules, such as liposomes, IgM and other molecules that are size excluded from ready permeability to tumor sites. When such biotinylated, high molecular weight molecules aggregate with NR-LU-13-avidin, the aggregated complexes are readily cleared from the circulation via the RES.

EXAMPLE X

Enhancement of Therapeutic Agent Internalization Through Avidin Crosslinking The ability of multivalent avidin to crosslink two or more biotin molecules (or chelate-biotin conjugates) is advantageously used to improve delivery of therapeutic agents. More specifically, avidin crosslinking induces internalization of crosslinked complexes at the target cell surface.

Biotinylated NR-CO-04 (lysine) is prepared according to the methods described in Example IV.A., above. Doxorubicin-avidin conjugates are prepared by standard conjugation chemistry. The biotinylated NR-CO-04 is administered to a recipient and allowed to clear from the circulation. One of ordinary skill in the art of radioimmunotherapy is readily able to determine the optimal time for biotinylated NR-CO-04 tumor localization and clearance from the circulation. At such time, the doxorubicin-avidin conjugate is administered to the recipient. The avidin portion of the doxorubicin-avidin conjugate crosslinks the biotinylated NR-CO-04 on the cell surface, inducing internalization of the complex. Thus, doxorubicin is more efficiently delivered to the target cell.

In a first alternative protocol, a standard three-step pretargeting methodology is used to enhance intracellular delivery of a drug to a tumor target cell. By analogy to the description above, biotinylated NR-LU-05 is administered, followed by avidin (for blood clearance and to form the middle layer of the sandwich at the target cell-bound biotinylated antibody). Shortly thereafter, and prior to internalization of the biotinylated NR-LU-05-avidin complex, a methotrexate-biotin conjugate is administered.

In a second alternative protocol, biotinylated NR-LU-05 is further covalently linked to methotrexate. Subsequent administration of avidin induces internalization of the complex and enhances intracellular delivery of drug to the tumor target cell.

In a third alternative protocol, NR-CO-04-avidin is administered to a recipient and allowed to clear from the circulation and localize at the target site. Thereafter, a polybiotinylated species (such as biotinylated poly-L-lysine, as in Example IV.B., above) is administered. In this protocol, the drug to be delivered may be covalently attached to either the antibody-avidin component or to the polybiotinylated species. The polybiotinylated species induces internalization of the (drug)-antibody-avidin-polybiotin-(drug) complex.

EXAMPLE XI

Targeting Moiety-Anti-Ligand Conjugate for Two-Step Pretargeting In Vivo

A. Preparation of SMCC-derivatized Streptavidin.

31 mg (0.48 $\mu$mol) streptavidin was dissolved in 9.0 ml PBS to prepare a final solution at 3.5 mg/ml. The pH of the solution was adjusted to 8.5 by addition of 0.9 ml of 0.5 M borate buffer, pH 8.5. A DMSO solution of SMCC (3.5 mg/ml) was prepared, and 477 $\mu$l (4.8 $\mu$mol) of this solution was added dropwise to the vortexing protein solution. After 30 minutes of stirring, the solution was purified by G-25 (PD-10, Pharmacia, Piscataway, N.J.) column chromatography to remove unreacted or hydrolyzed SMCC. The purified SMCC-derivatized streptavidin was isolated (28 mg, 1.67 mg/ml).

B. Preparation of DTT-reduced NR-LU-10. To 77 mg NR-LU-10 (0.42 $\mu$mol) in 15.0 ml PBS was added 1.5 ml of 0.5 M borate buffer, pH 8.5. A DTT solution, at 400 mg/ml (165 $\mu$l) was added to the protein solution. After stirring at room temperature for 30 minutes, the reduced antibody was purified by G-25 size exclusion chromatography. Purified DTT-reduced NR-LU-10 was obtained (74 mg, 2.17 mg/ml).

C. Conjugation of SMCC-streptavidin to DTT- reduced NR-LU-10. DTT-reduced NR-LU-10 (63 mg, 29 ml, 0.42 $\mu$mol) was diluted with 44.5 ml PBS. The solution of SMCC-streptavidin (28 mg, 17 ml, 0.42 $\mu$mol) was added rapidly to the stirring solution of NR-LU-10. Total protein concentration in the reaction mixture was 1.0 mg/ml. The progress of the reaction was monitored by HPLC (Zorbax® GF-250, available from MacMod). After approximately 45 minutes, the reaction was quenched by adding solid sodium tetrathionate to a final concentration of 5 mM.

D. Purification of conjugate. For small scale reactions, monosubstituted or disubstituted with regard to streptavidin conjugate was obtained using HPLC Zorbax (preparative) size exclusion chromatography. The desired monosubstituted or disubstituted conjugate product eluted at 14.0–14.5 min (3.0 ml/min flow rate), while unreacted NR-LU-10 eluted at 14.5–15 min and unreacted derivatized streptavidin eluted at 19–20 min.

For larger scale conjugation reactions, monosubstituted or disubstituted adduct is isolatable using DEAE ion exchange chromatography. After concentration of the crude conjugate mixture, free streptavidin was removed therefrom by eluting the column with 2.5% xylitol in sodium borate buffer, pH 8.6. The bound unreacted antibody and desired conjugate were then sequentially eluted from the column using an increasing salt gradient in 20 mM diethanolamine adjusted to pH 8.6 with sodium hydroxide.

E. Characterization of Conjugate.

1. HPLC size exclusion was conducted as described above with respect to small scale purification.

2. SDS-PAGE analysis was performed using 5% polyacrylamide gels under non-denaturing conditions. Conjugates to be evaluated were not boiled in sample buffer containing SDS to avoid dissociation of streptavidin into its 15 kD subunits. Two product bands were observed on the gel, which correspond to the mono- and di- substituted conjugates.

3. Immunoreactivity was assessed, for example, by competitive binding ELISA as compared to free antibody. Values obtained were within 10% of those for the free antibody.

4. Biotin binding capacity was assessed, for example, by titrating a known quantity of conjugate with p-[I-125] iodobenzoylbiocytin. Saturation of the biotin binding sites was observed upon addition of 4 equivalences of the labeled biocytin.

5. in vivo studies are useful to characterize the reaction product, which studies include, for example, serum clearance profiles, ability of the conjugate to target antigen-positive tumors, tumor retention of the conjugate over time and the ability of a biotinylated molecule to bind streptavidin conjugate at the tumor. These data facilitate determination that the synthesis resulted in the formation of a 1:1 streptavidin-NR-LU-10 whole antibody conjugate that exhibits blood clearance properties similar to native NR-LU-10 whole antibody, and tumor uptake and retention properties at least equal to native NR-LU-10.

Figure 3:
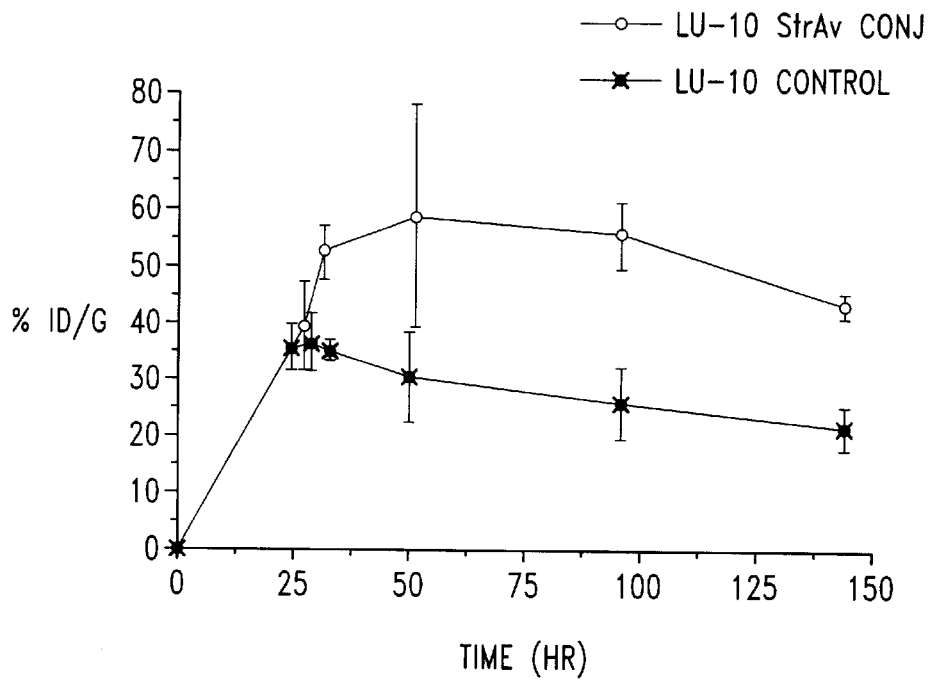
FIG. 3 depicts the tumor uptake profile of NR-LU-10-streptavidin conjugate (LU-10-StrAv) in comparison to a control profile of native NR-LU-10 whole antibody.

For example, FIG. 3 depicts the tumor uptake profile of the NR-LU-10-streptavidin conjugate (LU-10-StrAv) in comparison to a control profile of native NR-LU-10 whole antibody. LU-10-StrAv was radiolabeled on the streptavidin component only, giving a clear indication that LU-10-StrAv localizes to target cells as efficiently as NR-LU-10 whole antibody itself.

EXAMPLE XII

Two-Step Pretargeting In Vivo

A $^{186}$Re-chelate-biotin conjugate (Re-BT) of Example I (MW$\approx$1000; specific activity =1–2 mCi/mg) and a biotin-iodine-131 small molecule, PIP-Biocytin (PIP-BT, MW approximately equal to 602; specific activity =0.5–1.0 mCi/ mg), as discussed in Example VII above, were examined in a three-step pretargeting protocol in an animal model, as described in Example V above. Like Re-BT, PIP-BT has the ability to bind well to avidin and is rapidly cleared from the blood, with a serum half-life of about 5 minutes. Equivalent results were observed for both molecules in the two-step pretargeting experiments described herein.

Figure 4:
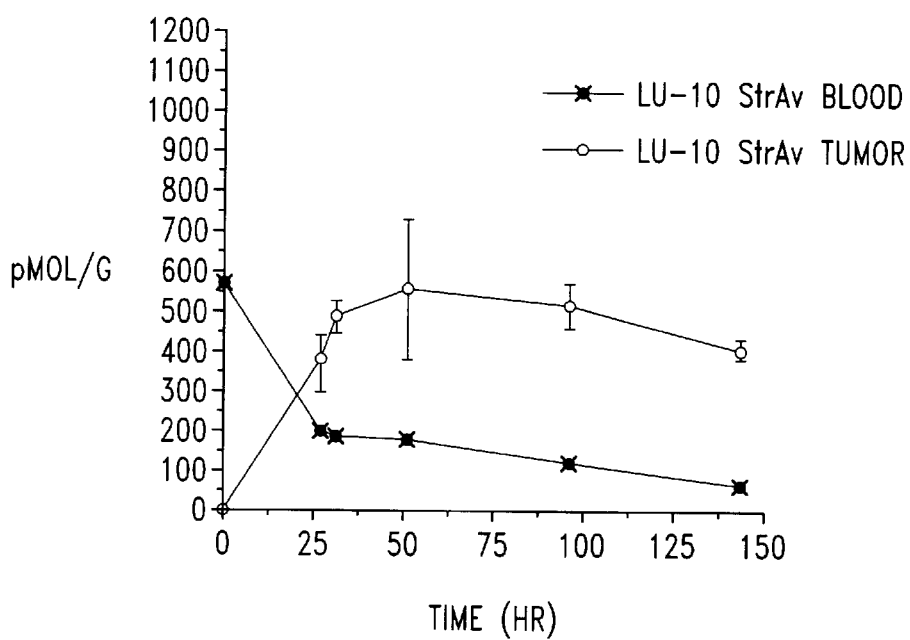
FIG. 4 depicts the tumor uptake and blood clearance profiles of NR-LU-10-streptavidin conjugate.

NR-LU-10 antibody (MW≈150 kD) was conjugated to streptavidin (MW≈66 kD) (as described in Example XI above) and radiolabeled with $^{125}$I/PIP-NHS (as described for radioiodination of NR-LU-10 in Example IV.A., above). The experimental protocol was as follows:

| Time 0 | inject (i.v.) 200 μg NR-LU-10-StrAv conjugate; |
|---|---|
| Time 24–48 h | inject (i.v.) 60–70 fold molar excess of radiolabeled biotinyl molecule; | and perform biodistributions at 2, 6, 24, 72, 120 hours after injection of radiolabeled biotinyl molecule NR-LU-10-streptavidin has shown very consistent patterns of blood clearance and tumor uptake in the LS-180 animal model. A representative profile is shown in FIG. 4. When either PIP-BT or Re-BT is administered after allowing the LU-10-StrAv conjugate to localize to target cell sites for at least 24 hours, the tumor uptake of therapeutic radionuclide is high in both absolute amount and rapidity. For PIP-BT administered at 37 hours following LU-10-StrAv (I-125) administration, tumor uptake was above 500 pMOL/G at the 40 hour time point and peaked at about 700 pMOL/G at 45 hours post-LU-10-StrAv administration.

This almost instantaneous uptake of a small molecule therapeutic into tumor in stoichiometric amounts comparable to the antibody targeting moiety facilitates utilization of the therapeutic radionuclide at its highest specific activity. Also, the rapid clearance of radionuclide that is not bound to LU-10-StrAv conjugate permits an increased targeting ratio (tumor:blood) by eliminating the slow tumor accretion phase observed with directly labeled antibody conjugates. The pattern of radionuclide tumor retention is that of whole antibody, which is very persistent.

Experimentation using the two-step pretargeting approach and progressively lower molar doses of radiolabeled biotinyl molecule was also conducted. Uptake values of about 20% ID/G were achieved at no-carrier added (high specific activity) doses of radiolabeled biotinyl molecules. At less than saturating doses, circulating LU-10-StrAv was observed to bind significant amounts of administered radiolabeled biotinyl molecule in the blood compartment.

EXAMPLE XIII

Asialoorosomucoid Clearing Agent and Two-Step Pretargeting

In order to maximize the targeting ratio (tumor:blood), clearing agents were sought that are capable of clearing the blood pool of targeting moiety-anti-ligand conjugate (e.g., LU-10-StrAv), without compromising the ligand binding capacity thereof at the target sites. One such agent, biotinylated asialoorosomucoid, which employs the avidin-biotin interaction to conjugate to circulating LU-10-StrAv, was tested.

A. Derivitization of orosomucoid. 10 mg human orosomucoid (Sigma N-9885) was dissolved in 3.5 ml of pH 5.5 0.1 M sodium acetate buffer containing 160 mM NaCl. 70 μl of a 2% (w/v) CaCl solution in deionized (D.I.) water was added and 11 μl of neuraminidase (Sigma N-7885), 4.6 U/ml, was added. The mixture was incubated at 37° C. for 2 hours, and the entire sample was exchanged over a Centricon-10® ultrafiltration device (available from Amicon, Danvers, Massachusetts) with 2 volumes of PBS. The asialoorosomucoid and orosomucoid starting material were radiolabeled with I-125 using PIP technology, as described in Example IV above.

Figure 5:
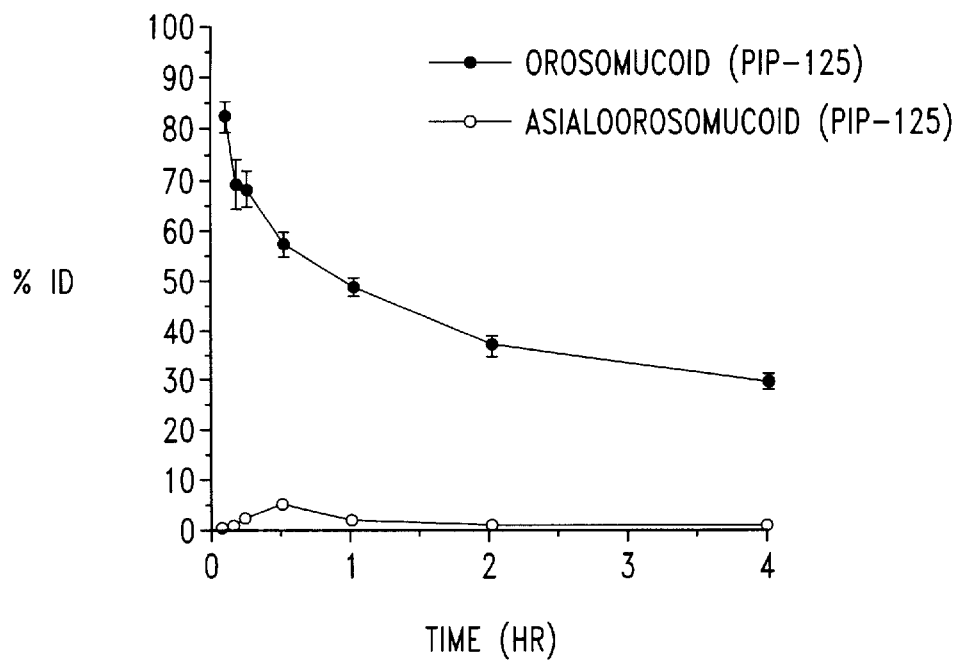
FIG. 5 depicts the rapid clearance from the blood of asialoorosomucoid in comparison with orosomucoid in terms of percent injected dose of I-125-labeled protein.

The two radiolabeled preparations were injected i.v. into female BALB/c mice (20–25 g), and blood clearance was assessed by serial retro-orbital eye bleeding of each group of three mice at 5, 10, 15 and 30 minutes, as well as at 1, 2 and 4 hours post-administration. The results of this experiment are shown in FIG. 5, with asialoorosomucoid clearing more rapidly than its orosomucoid counterpart.

Figure 6:
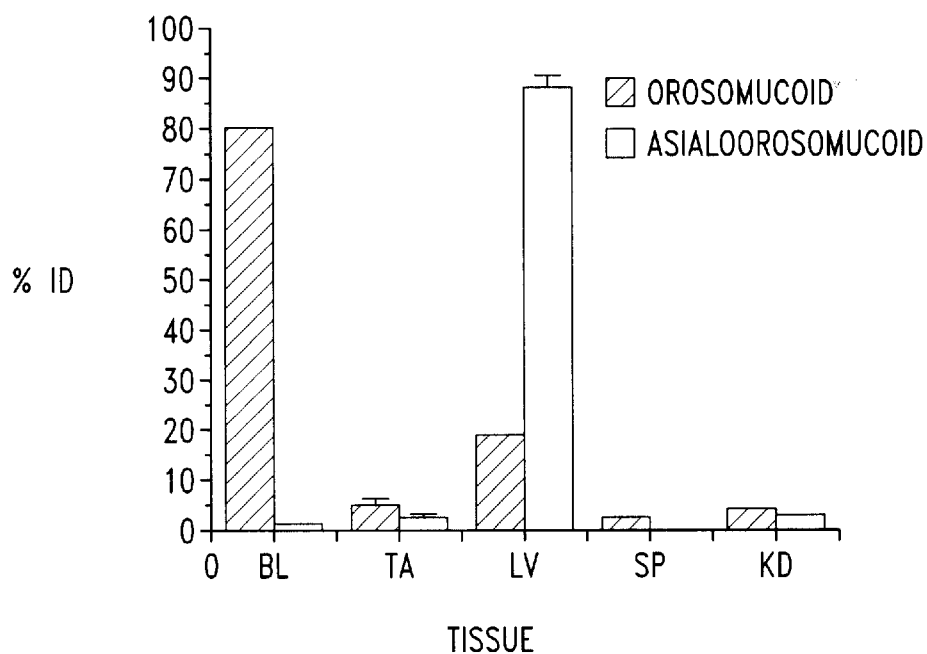
FIG. 6 depicts the 5 minute limited biodistribution of asialoorosomucoid in comparison with orosomucoid in terms of percent injected dose of I-125-labeled protein.

In addition, two animals receiving each compound were sacrificed at 5 minutes post-administration and limited biodistributions were performed. These results are shown in FIG. 6. The most striking aspects of these data are the differences in blood levels (78% for orosomucoid and 0.4% for asialoorosomucoid) and the specificity of uptake of asialoorosomucoid in the liver (86%), as opposed to other tissues.

B. Biotinylation of asialoorosomucoid clearing agent and orosomucoid control. 100 μl of 0.2 M sodium carbonate buffer, pH 9.2, was added to 2 mg (in 1.00 ml PBS) of PIP-125-labeled orosomucoid and to 2 mg PIP-125-labeled asialoorosomucoid. 60 μl of a 1.85 mg/ml solution of NHS-amino caproate biotin in DMSO was then added to each compound. The reaction mixtures were vortexed and allowed to sit at room temperature for 45 minutes. The material was purified by size exclusion column chromatography (PD-10, Pharmacia) and eluted with PBS. 1.2 ml fractions were taken, with fractions 4 and 5 containing the majority of the applied radioactivity (>95%). Streptavidin-agarose beads (Sigma S-1638) or -pellets were washed with PBS, and 20 μg of each biotinylated, radiolabeled protein was added to 400 μl of beads and 400 μl of PBS, vortexed for 20 seconds and centrifuged at 14,000 rpm for 5 minutes. The supernatant was removed and the pellets were washed with 400 μl PBS. This wash procedure was repeated twice more, and the combined supernatants were assayed by placing them in a dosimeter versus their respective pellets. The values are shown below in Table 4.

TABLE 4

| Compound | Supernatant | Pellet |
|---|---|---|
| orosomucoid | 90% | 10% |
| biotin-oroso | 7.7% | 92.% |
| asialoorosomucoid | 92% | 8.0% |
| biotin-asialo | 10% | 90% |

C. Protein-Streptavidin Binding in viva. Biotin-asialoorosomucoid was evaluated for the ability to couple with circulating LU-10-StrAv conjugate in vivo and to remove it from the blood. Female BALB/c mice (20–25 g) were injected i.v. with 200 μg LU-10-StrAv conjugate. Clearing agent (200 μl PBS—group 1; 400 μg non-biotinylated asialoorosomucoid—group 2; 400 μg biotinylated asialoorosomucoid—group 3; and 200 μg biotinylated asialoorosomucoid—group 4) was administered at 25 hours following conjugate administration. A fifth group received PIP-I-131-LU-10-StrAv conjugate which had been saturated prior to injection with biotin—group 5. The 400 μg dose constituted a 10:1 molar excess of clearing agent over the initial dose of LU-10-StrAv conjugate, while the 200 μg dose constituted a 5:1 molar excess. The saturated PIP-I-

131-LU-10-StrAv conjugate was produced by addition of a 10-fold molar excess of D-biotin to 2 mg of LU-10-StrAv followed by size exclusion purification on a G-25 PD-10 column.

Three mice from each group were serially bled, as described above, at 0.17, 1, 4 and 25 hours (pre-injection of clearing agent), as well as at 27, 28, 47, 70 and 90 hours. Two additional animals from each group were sacrificed at 2 hours post-clearing agent administration and limited biodistributions were performed.

Figure 7:
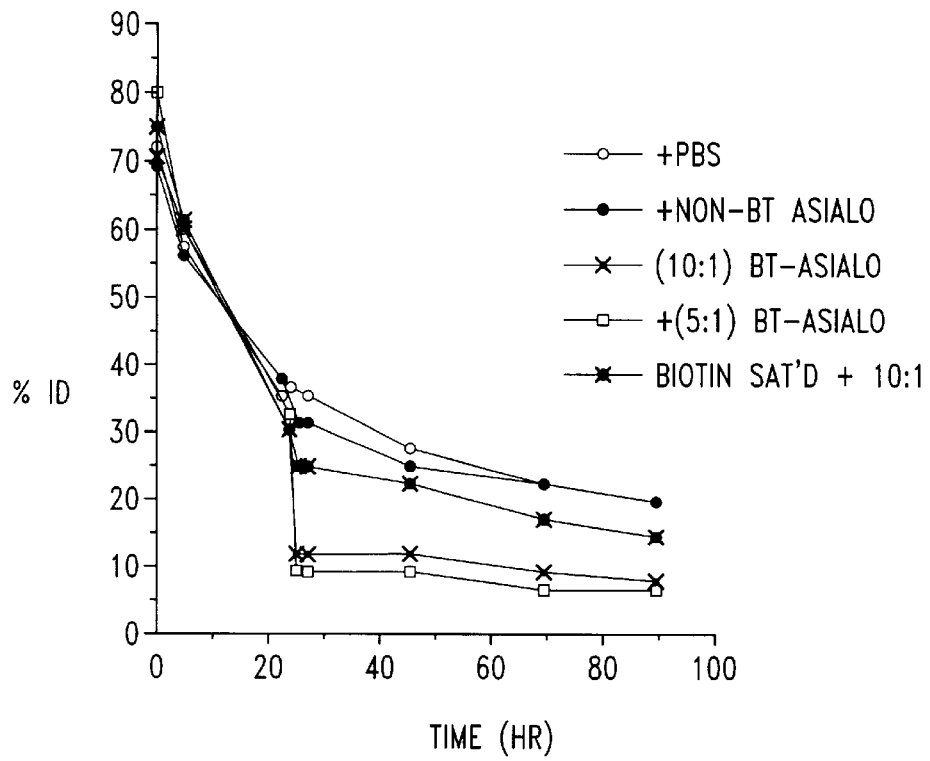
FIG. 7 depicts NR-LU-10-streptavidin conjugate blood clearance upon administration of three controls (○, ●, ■) and two doses of a clearing agent (◇,□) at 25 hours post-conjugate administration.

The blood clearance data are shown in FIG. 7. These data indicate that circulating LU-10-StrAv radioactivity in groups 3 and 4 was rapidly and significantly reduced, in comparison to those values obtained in the control groups 1, 2 and 5. Absolute reduction in circulating antibody-streptavidin conjugate was approximately 75% when compared to controls.

Biodistribution data are shown in tabular form in FIG. 8. The biodistribution data show reduced levels of conjugate for groups 3 and 4 in all tissues except the liver, kidney and intestine, which is consistent with the processing and excretion of radiolabel associated with the conjugate after complexation with biotinylated asialoorosomucoid.

Figure 9:
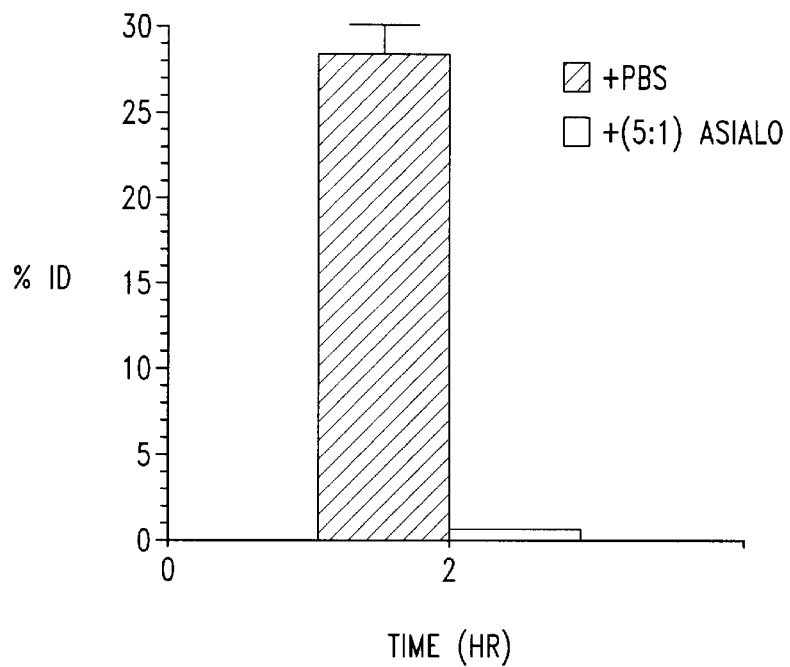
FIG. 9 depicts NR-LU-10-streptavidin conjugate serum biotin binding capability at 2 hours post-clearing agent administration.

Furthermore, residual circulating conjugate was obtained from serum samples by cardiac puncture (with the assays conducted in serum+PBS) and analyzed for the ability to bind biotin (immobilized biotin on agarose beads), an indicator of functional streptavidin remaining in the serum. Group 1 animal serum showed conjugate radiolabel bound about 80% to immobilized biotin. Correcting the residual circulating radiolabel values by multiplying the remaining percent injected dose (at 2 hours after clearing agent administration) by the remaining percent able to bind immobilize biotin (the amount of remaining functional conjugate) leads to the graph shown in FIG. 9. Administration of 200 $\mu$g biotinylated asialoorosomucoid resulted in a 50-fold reduction in serum biotin-binding capacity and, in preliminary studies in tumored animals, has not exhibited cross-linking and removal of prelocalized LU-10-StrAv conjugate from the tumor. Removal of circulating targeting moiety-antiligand without diminishing biotin-binding capacity at target cell sites, coupled with an increased radiation dose to the tumor resulting from an increase in the amount of targeting moiety-anti-ligand administered, results in both increased absolute rad dose to tumor and diminished toxicity to non-tumor cells, compared to what is currently achievable using conventional radioimmunotherapy.

Figure 10:
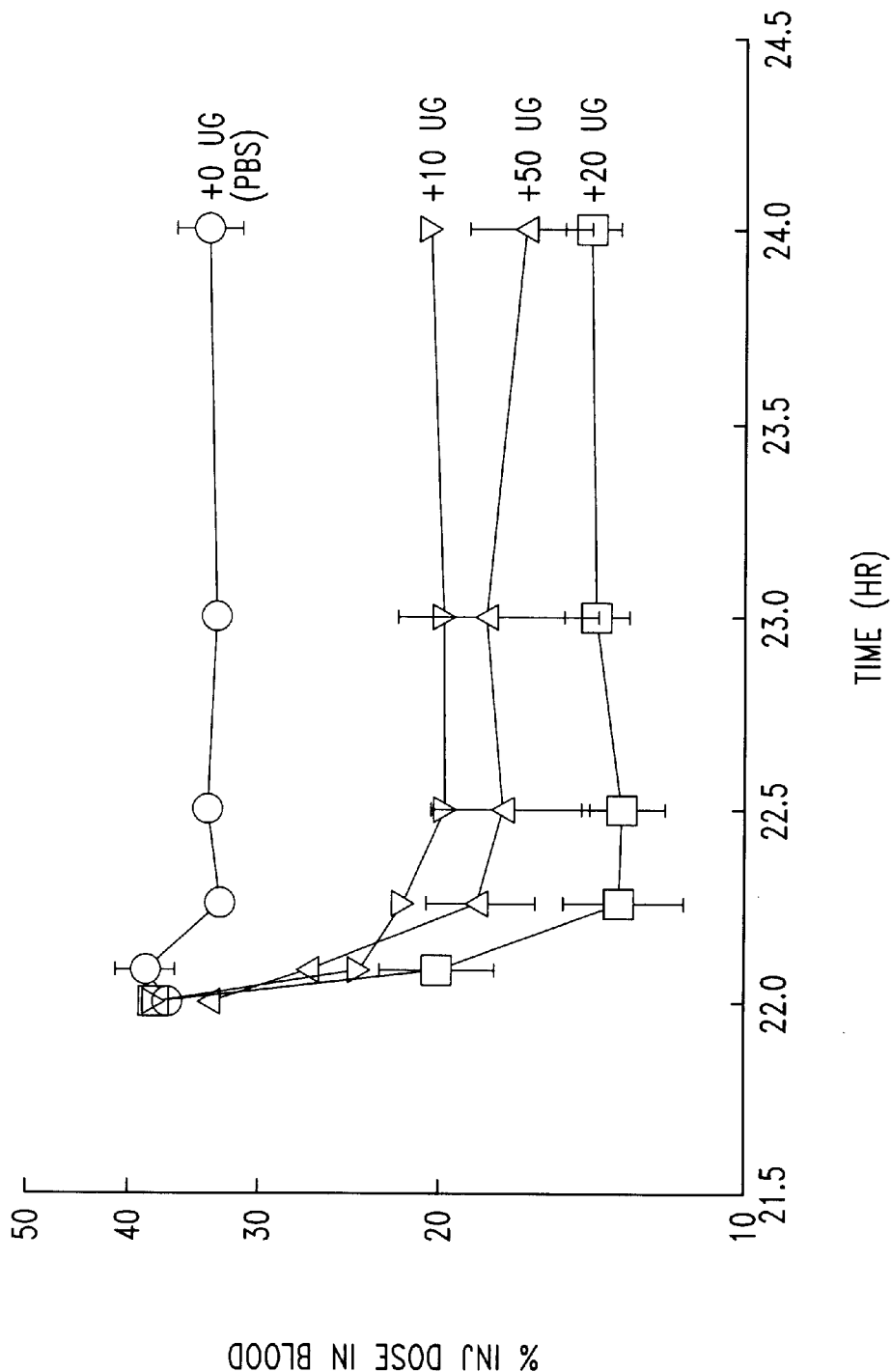
FIG. 10 depicts NR-LU-10-streptavidin conjugate blood clearance over time upon administration of a control (○) and three doses of a clearing agent (◇, □, □) at 24 hours post-conjugate administration.
Figure 11A:
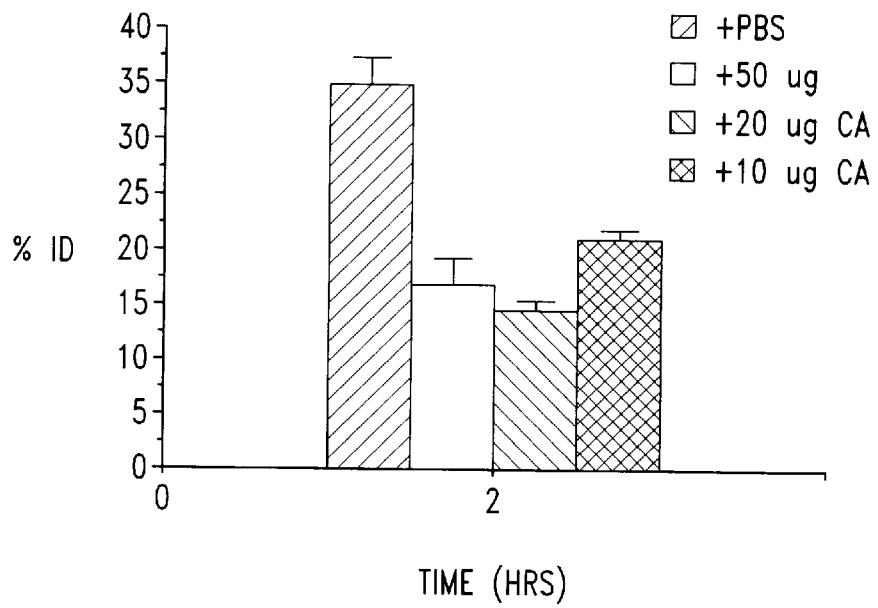
FIG. 11A depicts the blood clearance of LU-10-StrAv conjugate upon administration of a control (PBS) and three doses (50, 20 and 10 μg) of clearing agent at two hours post-clearing agent administration.
Figure 11B:
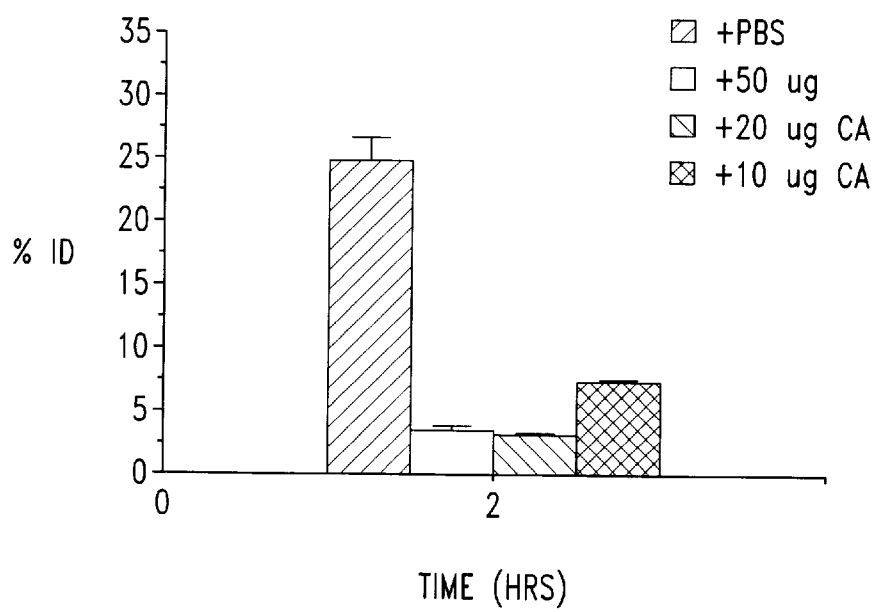
FIG. 11B depicts LU-10-StrAv conjugate serum biotin binding capability upon administration of a control (PBS) and three doses (50, 20 and 10 μg) of clearing agent at two hours post-clearing agent administration.

A subsequent experiment was executed to evaluate lower doses of asialoorosomucoid-biotin. In the same animal model, doses of 50, 20 and 10 $\mu$g asialoorosomucoid-biotin were injected at 24 hours following administration of the LU-10-StrAv conjugate. Data from animals serially bled are shown in FIG. 10, and data from animals sacrificed two hours after clearing agent administration are shown in FIGS. 11A (blood clearance) and 11B (serum biotin-binding), respectively. Doses of 50 and 20 $\mu$g asialoorosomucoid-biotin effectively reduced circulating LU-10-StrAv conjugate levels by about 65% (FIG. 11A) and, after correction for binding to immobilized biotin, left only 3% of the injected dose in circulation that possessed biotin-binding capacity, compared with about 25% of the injected dose in control animals (FIG. 11B). Even at low doses (approaching 1:1 stoichiometry with circulating LU-10-StrAv conjugate), asialoorosomucoid-biotin was highly effective at reducing blood levels of circulating streptavidin-containing conjugate by an in vivo complexation that was dependent upon biotin-avidin interaction.

EXAMPLE XIV

Tumor Uptake of PIP-Biocytin

PIP-Biocytin, as prepared and described in Example VII above, was tested to determine the fate thereof in vivo. The following data are based on experimentation with tumored nude mice (100 mg LS-180 tumor xenografts implanted subcutaneously 7 days prior to study) that received, at time 0, 200 $\mu$g of I-125 labeled NR-LU-10-Streptavidin conjugate (950 pmol), as discussed in Example XI above. At 24 hours, the mice received an i.v. injection of PIP-I-131-biocytin (40 $\mu$Ci) and an amount of cold carrier PIP-I-127 biocytin corresponding to doses of 42 $\mu$g (69,767 pmol), 21 $\mu$g (34,884 pmol), 5.7 $\mu$g (9468 pmol), 2.85 $\mu$g (4734 pmol) or 0.5 $\mu$g (830 pmol). Tumors were excised and counted for radioactivity 4 hours after PIP-biocytin injection.

The three highest doses produced PIP-biocytin tumor localizations of about 600 pmol/g. Histology conducted on tissues receiving the two highest doses indicated that saturation of tumor-bound streptavidin was achieved. Equivalent tumor localization observed at the 5.7 $\mu$g dose is indicative of streptavidin saturation as well. In contrast, the two lowest doses produced lower absolute tumor localization of PIP-biocytin, despite equivalent localization of NR-LU-10-Streptavidin conjugate (tumors in all groups averaged about 40% ID/G for the conjugate).

The lowest dose group (0.5 $\mu$g) exhibited high efficiency tumor delivery of PIP-I-131-biocytin, which efficiency increased over time. A peak uptake of 85.0% ID/G was observed at the 120 hour time point (96 hours after administration of PIP-biocytin). Also, the absolute amount of PIP-biocytin, in terms of % ID, showed a continual increase in the tumor over all of the sampled time points. The decrease in uptake on a % ID/G basis at the 168 hour time point resulted from significant growth of the tumors between the 120 and 168 hour time points.

In addition, the co-localization of NR-LU-10-Streptavidin conjugate (LU-10-StrAv) and the subsequently administered PIP-Biocytin at the same tumors over time was examined. The localization of radioactivity at tumors by PIP-biocytin exhibited a pattern of uptake and retention that differed from that of the antibody-streptavidin conjugate (LU-10-StrAv). LU-10-StrAv exhibited a characteristic tumor uptake pattern that is equivalent to historical studies of native NR-LU-10 antibody, reaching a peak value of 40% ID/G between 24 and 48 hours after administration. In contrast, the PIP-Biocytin exhibited an initial rapid accretion in the tumor, reaching levels greater than those of LU-10-StrAv by 24 hours after PIP-Biocytin administration. Moreover, the localization of PIP-Biocytin continued to increase out to 96 hours, when the concentration of radioactivity associated with the conjugate has begun to decrease. The slightly greater amounts of circulating PIP-Biocytin compared to LU-10-StrAv at these time points appeared insufficient to account for this phenomenon.

The ratio of PIP-Biocytin to LU-10-StrAv in the tumor increased continually during the experiment, while the ratio in the blood decreased continually. This observation is consistent with a process involving continual binding of targeting moiety-containing conjugate (with PIP-Biocytin bound to it) from the blood to the tumor, with subsequent differential processing of the PIP-Biocytin and the conjugate. Since radiolabel associated with the streptavidin conjugate component (compared to radiolabel associated with the targeting moiety) has shown increased retention in organs of metabolic processing, PIP-Biocytin associated with the streptavidin appears to be selectively retained by the tumor cells. Because radiolabel is retained at target cell sites, a greater accumulation of radioactivity at those sites results.

The $AUC_{tumor}/AUC_{blood}$ for PIP-Biocytin is over twice that of the conjugate (4.27 compared to 1.95, where AUC means "area under the curve"). Further, the absolute $AUC_{tumor}$ for PIP-Biocytin is nearly twice that of the conjugate (9220 compared to 4629). Consequently, an increase in radiation dose to tumor was achieved.

EXAMPLE XV

Clearing Agent Evaluation Experimentation

The following experiments conducted on non-tumor-bearing mice were conducted using female BALB/c mice (20–25 g). For tumor-bearing mice experimentation, female nude mice were injected subcutaneously with LS-180 tumor cells, and, after 7 d, the mice displayed 50–100 mg tumor xenografts. The monoclonal antibody used in these experiments was NR-LU-10. When radiolabeled, the NR-LU-10-streptavidin conjugate was radiolabeled with I-125 using procedures described herein. When radiolabeled, PIP-biocytin was labeled with I-131 or I-125 using procedures described herein.

A. Utility of Asialoorosomucoid-Biotin (AO-Bt) in Reducing Circulating Radioactivity from a Subsequently Administered Radiolabeled Biotin Ligand. Mice bearing LS-180 colon tumor xenografts were injected with 200 micrograms NR-LU-10 antibody-streptavidin (MAb-StrAv) conjugate at time 0, which was allowed to prelocalize to tumor for 22 hours. At that time, 20 micrograms of AO-Bt was administered to one group of animals. Two hours later, 90 micrograms of a radioisotope-bearing, ligand-containing small molecule (PIP-biotin-dextran prepared as discussed in part B hereof) was administered to this group of mice and also to a group which had not received AO-Bt. The results of this experiment with respect to radiolabel uptake in tumor and clearance from the blood indicated that tumor-targeting of the radiolabeled biotin-containing conjugate was retained while blood clearance was enhanced, leading to an overall improvement in amount delivered to target/amount located in serum. The AUC tumor/AUC blood with clearing agent was 6.87, while AUC tumor/AUC blood without clearing agent was 4.45. Blood clearance of the circulating MAb-StrAv conjugate was enhanced with the use of clearing agent. The clearing agent was radiolabeled in a separate group of animals and found to bind directly to tumor at very low levels (1.7 pmol/g at a dose of 488 total pmoles (0.35% ID/g), indicating that it does not significantly compromise the ability of tumor-bound MAb-StrAv to bind subsequently administered radiolabeled ligand.

B. Preparation Protocol for PIP-Biotin-Dextran. A solution of 3.0 mg biotin-dextran, lysine fixable (BDLF, available from Sigma Chemical Co., St. Louis, Mo., 70,000 dalton molecular weight with approximately 18 biotins/molecule) in 0.3 ml PBS and 0.15 ml 1 M sodium carbonate, pH 9.25, was added to a dried residue (1.87 mCi) of N-succinimidyl p-I-125-iodobenzoate prepared in accordance with Wilbur, et al., *J. Nucl. Med.*, 30: 216–226, 1989.

C. Dosing Optimization of AO-Bt. Tumored mice receiving StrAv-MAb as above, were injected with increasing doses of AO-Bt (0 micrograms, 20 micrograms, 50 micrograms, 100 micrograms and 200 micrograms). Tumor uptake of I-131-PIP-biocytin (5.7 micrograms, administered 2 hours after AO-Bt administration) was examined. Increasing doses of AO-Bt had no effect on tumor localization of MAb-StrAv. Data obtained 44 hours after AO-Bt administration showed the same lack of effect. This data indicates that AO-Bt dose not crosslink and internalize MAb-StrAv on the tumor surface, as had been noted for avidin administered following biotinylated antibody.

PIP-biocytin tumor localization was inhibited at higher doses of AO-Bt. This effect is most likely due to reprocessing and distribution to tumor of biotin used to derivatize AO-Bt. Optimal tumor to blood ratios (% injected dose of radiolabeled ligand/gram weight of tumor divided by % injected dose of radioligand/gram weight of blood were achieved at the 50 microgram dose of AO-Bt. Biodistributions conducted following completion of the protocols employing a 50 microgram AO-Bt dose revealed low retention of radiolabel in all non-target tissues (1.2 pmol/g in blood; 3.5 pmol/gram in tail; 1.0 pmol/g in lung; 2.2 pmol/g in liver; 1.0 pmol/g is spleen; 7.0 pmol/g in stomach; 2.7 pmol/g in kidney; and 7.7 pmol/g in intestine). With 99.3 pmol/g in tumor, these results indicate effective decoupling of the PIP-biocytin biodistribution from that of the MAb-StrAv at all sites except tumor. This decoupling occurred at all clearing agent doses in excess of 50 micrograms as well. Decreases in tumor localization of PIP-biocytin was the significant result of administering clearing agent doses in excess of 50 micrograms. In addition, the amount of PIP-biocytin in non-target tissues 44 hours after administration was identical to localization resulting from administration of PIP-biocytin alone (except for tumor, where negligible accretion was seen when PIP-biocytin was administered alone), indicating effective decoupling.

D. Further Investigation of Optimal Clearing Agent Dose. Tumored mice injected with MAb-StrAv at time 0 as above; 50 micrograms of AO-Bt at time 22 hours; and 545 microcuries of I-131-PIP-biocytin at time 25 hours. Whole body radiation was measured and compared to that of animals that had not received clearing agent. 50 micrograms of AO-Bt was efficient in allowing the injected radioactivity to clear from the animals unimpeded by binding to circulating MAb-StrAv conjugate. Tumor uptake of I-131-PIP-biocytin was preserved at the 50 microgram clearing agent dose, with AUC tumor/AUC blood of 30:1 which is approximately 15-fold better than the AUC tumor/AUC blood achieved in conventional antibody-radioisotope therapy using this model.

E. Galactose- and Biotin-Derivatization of Human Serum Albumin (HSA). HSA was evaluated because it exhibits the advantages of being both inexpensive and non-immunogenic. HSA was derivatized with varying levels of biotin (1-about 9 biotins/molecule) via analogous chemistry to that previously described with respect to AO. More specifically, to a solution of HSA available from Sigma Chemical Co. (5–10 mg/ml in PBS) was added 10% v/v 0.5 M sodium borate buffer, pH 8.5, followed by dropwise addition of a DMSO solution of NHS-LC-biotin (Sigma Chemical Co.) to the stirred solution at the desired molar offering (relative molar equivalents of reactants). The final percent DMSO in the reaction mixture should not exceed 5%. After stirring for 1 hour at room temperature, the reaction was complete. A 90% incorporation efficiency for biotin on HSA was generally observed. As a result, if 3 molar equivalences of the NHS ester of LC-biotin was introduced, about 2.7 biotins per HSA molecule were obtained. Unreacted biotin reagent was removed from the biotin-derivatized HSA using G-25 size exclusion chromatography. Alternatively, the crude material may be directly galactosylated. The same chemistry is applicable for biotinylating non-previously biotinylated dextran.

HSA-biotin was then derivatized with from 12 to 15 galactoses/molecule. Galactose derivatization of the biotinylated HSA was performed according to the procedure of Lee, et al., *Biochemistry*, 15: 3956, 1976. More specifically, a 0.1 M methanolic solution of cyanomethyl-2,3,4,6-tetra-O-acetyl-1-thio-D-galactopyranoside was prepared and reacted with a 10% v/v 0.1 M NaOMe in methanol for 12 hours to generate the reactive galactosyl thioimidate. The galactosylation of biotinylated HSA began by initial evaporation of the anhydrous methanol from a 300 fold molar excess of reactive thioimidate. Biotinylated HSA in PBS, buffered with 10% v/v 0.5 M sodium borate, was added to the oily residue. After stirring at room temperature for 2 hours, the mixture was stored at 4° C. for 12 hours. The galactosylated HSA-biotin was then purified by G-25 size exclusion chromatography or by buffer exchange to yield the desired product. The same chemistry is exploitable to galactosylating dextran. The incorporation efficiency of galactose on HSA is approximately 10%.

70 micrograms of Galactose-HSA-Biotin (G-HSA-B), with 12–15 galactose residues and 9 biotins, was administered to mice which had been administered 200 micrograms of StrAv-MAb or 200 microliters of PBS 24 hours earlier. Results indicated that G-HSA-B is effective in removing StrAv-MAb from circulation. Also, the pharmacokinetics of G-HSA-B is unperturbed and rapid in the presence or absence of circulating MAb-StrAv.

F. Non-Protein Clearing Agent. A commercially available form of dextran, molecular weight of 70,000 daltons, pre-derivatized with approximately 18 biotins/molecule and having an equivalent number of free primary amines was studied. The primary amine moieties were derivatized with a galactosylating reagent, substantially in accordance with the procedure therefor described above in the discussion of HSA-based clearing agents, at a level of about 9 galactoses/molecule. The molar equivalence offering ratio of galactose to HSA was about 300:1, with about one-third of the galactose being converted to active form. 40 Micrograms of galactose-dextran-biotin (GAL-DEX-BT) was then injected i.v. into one group of mice which had received 200 micrograms MAb-StrAv conjugate intravenously 24 hours earlier, while 80 micrograms of GAL-DEX-BT was injected into other such mice. GAL-DEX-BT was rapid and efficient at clearing StrAv-MAb conjugate, removing over 66% of circulating conjugate in less than 4 hours after clearing agent administration. An equivalent effect was seen at both clearing agent doses, which correspond to 1.6 (40 micrograms) and 3.2 (80 micrograms) times the stoichiometric amount of circulating StrAv conjugate present.

G. Dose Ranging for G-HSA-B Clearing Agent. Dose ranging studies followed the following basic format:

200 micrograms MAb-StrAv conjugate administered;

24 hours later, clearing agent administered; and 2 hours later, 5.7 micrograms PIP-biocytin administered.

Dose ranging studies were performed with the G-HSA-B clearing agent, starting with a loading of 9 biotins per molecule and 12–15 galactose residues per molecule. Doses of 20, 40, 70 and 120 micrograms were administered 24 hours after a 200 microgram dose of MAb-StrAv conjugate. The clearing agent administrations were followed 2 hours later by administration of 5.7 micrograms of I-131-PIP-biocytin. Tumor uptake and blood retention of PIP-biocytin was examined 44 hours after administration thereof (46 hours after clearing agent administration). The results showed that a nadir in blood retention of PIP-biocytin was achieved by all doses greater than or equal to 40 micrograms of G-HSA-B. A clear, dose-dependent decrease in tumor binding of PIP-biocytin at each increasing dose of G-HSA-B was present, however. Since no dose-dependent effect on the localization of MAb-StrAv conjugate at the tumor was observed, this data was interpreted as being indicative of relatively higher blocking of tumor-associated MAb-StrAv conjugate by the release of biotin from catabolized clearing agent. Similar results to those described earlier for the asialoorosomucoid clearing agent regarding plots of tumor/blood ratio were found with respect to G-HSA-B, in that an optimal balance between blood clearance and tumor retention occurred around the 40 microgram dose. Because of the relatively large molar amounts of biotin that could be released by this clearing agent at higher doses, studies were undertaken to evaluate the effect of lower levels of biotinylation on the effectiveness of the clearing agent. G-HSA-B, derivatized with either 9, 5 or 2 biotins/molecule, was able to clear MAb-StrAv conjugate from blood at equal protein doses of clearing agent. All levels of biotinylation yielded effective, rapid clearance of MAb-StrAv from blood.

Comparison of these 9-, 5-, and 2-biotin-derivatized clearing agents with a single biotin G-HSA-B clearing agent was carried out in tumored mice, employing a 60 microgram dose of each clearing agent. This experiment showed each clearing agent to be substantially equally effective in blood clearance and tumor retention of MAb-StrAv conjugate 2 hours after clearing agent administration. The G-HSA-B with a single biotin was examined for the ability to reduce binding of a subsequently administered biotinylated small molecule (PIP-biocytin) in blood, while preserving tumor binding of PIP-biocytin to prelocalized MAb-StrAv conjugate. Measured at 44 hours following PIP-biocytin administration, tumor localization of both the Mab-StrAv conjugate and PIP-biocytin was well preserved over a broad dose range of G-HSA-B with one biotin/molecule (90 to 180 micrograms). A progressive decrease in blood retention of PIP-biocytin was achieved by increasing doses of the single biotin G-HSA-B clearing agent, while tumor localization remained essentially constant, indicating that this clearing agent, with a lower level of biotinylation, is preferred. This preference arises because the single biotin G-HSA-B clearing agent is both effective at clearing MAb-StrAv over a broader range of doses (potentially eliminating the need for patient-to-patient titration of optimal dose) and appears to release less competing biotin into the systemic circulation than the same agent having a higher biotin loading level.

Another way in which to decrease the effect of clearing agent-released biotin on active agent-biotin conjugate binding to prelocalized targeting moiety-streptavidin conjugate is to attach the protein or polymer or other primary clearing agent component to biotin using a retention linker. A retention linker has a chemical structure that is resistant to agents that cleave peptide bonds and, optionally, becomes protonated when localized to a catabolizing space, such as a lysosome. Preferred retention linkers of the present invention are short strings of D-amino acids or small molecules having both of the characteristics set forth above. An exemplary retention linker of the present invention is cyanuric chloride, which may be interposed between an epsilon amino group of a lysine of a proteinaceous primary clearing agent component and an amine moiety of a reduced and chemically altered biotin carboxy moiety (which has been discussed above) to form a compound of the structure set forth below.

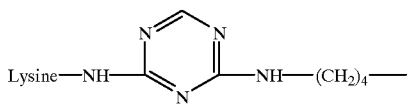

When the compound shown above is catabolized in a catabolizing space, the heterocyclic ring becomes protonated. The ring protonation prevents the catabolite from exiting the lysosome. In this manner, biotin catabolites containing the heterocyclic ring are restricted to the site(s) of catabolism and, therefore, do not compete with active-agent-biotin conjugate for prelocalized targeting moiety-streptavidin target sites.

Comparisons of tumor/blood localization of radiolabeled PIP-biocytin observed in the G-HSA-B dose ranging studies showed that optimal tumor to background targeting was achieved over a broad dose range (90 to 180 micrograms), with the results providing the expectation that even larger clearing agent doses would also be effective. Another key result of the dose ranging experimentation is that G-HSA-B with an average of only 1 biotin per molecule is presumably only clearing the MAb-StrAv conjugate via the Ashwell receptor mechanism only, because too few biotins are present to cause cross-linking and aggregation of MAb-StrAv conjugates and clearing agents with such aggregates being cleared by the reticuloendothelial system.

H. Tumor Targeting Evaluation Using G-HSA-B. The protocol for this experiment was as follows:

Time 0: administer 400 micrograms MAb-StrAv conjugate;

Time 24 hours: administer 240 micrograms of G-HSA-B with one biotin and 12–15 galactoses and Time 26 hours: administer 6 micrograms of was acidified with glacial acetic acid, evaporated and chromatographed on a 27 mm column packed with 50 g silica, eluting with 30% MeOH/EtOAc 1% HOAc to give the product as a white solid (383 mg) in 66% yield.

H-NMR (DMSO): 1.18–1.25 (m, 6H, $(CH_2)_3$), 2.15, 2.35 (2 t's, 2H, $CH_2CO$), 2.75 (m, 2H, $SCH_2$), 2.80, 3.00 (2 s's, 3H, $NCH_3$), 3.05–3.15 (m, 1H, SCH), 3.95, 4.05 (2 s's, 2H, $CH_2N$), 4.15, 4.32 (2 m's, 2H, 2CHN's), 6.35 (s, NH), 6.45 (s, NH).

2. Preparation of [(N-methyl-N-biotinyl)glycyl] aminobenzyl-DOTA. N-hydroxysuccinimide (10 mg, 0.08 mmol) and EDCI (15 mg, 6.08 mmol) were added to a solution of (N-methylglycyl biotin (24 mg, 0.08 mmol) in DMF (1.0 ml). The solution was stirred at 23° C. for 64 hours. Pyridine (0.8 ml) and aminobenzyl-DOTA (20 mg, 0.04 mmol) were added. The mixture was heated in an oil bath at 63° C. for 10 minutes, then stirred at 23° C. for 4 hours. The solution was evaporated. The residue was purified by preparative HPLC to give the product as an off white solid (8 mg, 0.01 mmol) in 27% yield.

H-NMR ($D_2O$): 1.30–1.80 (m, 6H), 2.40, 2.55 (2 t's, 2H, $CH_2CO$), 2.70–4.2 (complex multiplet), 4.35 (m, CHN), 4.55 (m, CHN), 7.30 (m, 2H, benzene hydrogens), 7.40 (m, 2H, benzene hydrogens).

Efficient delivery of the Lu-177-DOTA-biotin small molecule was observed, 20–25% injected dose/gram of tumor. These values are equivalent with the efficiency of the delivery of the MAb-StrAv conjugate. The AUC tumor/AUC blood obtained for this non-optimized clearing agent dose was 300% greater than that achievable by comparable direct MAb-radiolabel administration. Subsequent experimentation has resulted in AUC tumor/AUC blood over 1000% greater than that achievable by comparable conventional MAb-radiolabel administration. In addition, the HSA-based clearing agent is expected to exhibit a low degree of immunogenicity in humans.

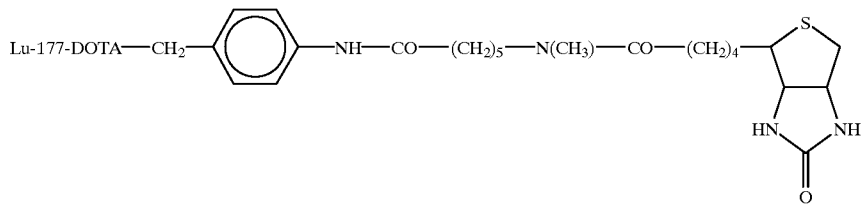

Lu-177 is complexed with the DOTA chelate using known techniques therefor, and the DOTA chelate is prepared in accordance with the following procedure. N-methyl-glycine (trivial name sarcosine, available from Sigma Chemical Co.) was condensed with biotin-NHS ester in DMF and triethylamine to obtain N-methyl glycyl-biotin. N-methyl-glycyl biotin was then activated with EDCI and NHS. The resultant NHS ester was not isolated and was condensed in situ with DOTA-aniline preparable using known techniques (e.g., McMurry et al., *Bicconjugate Chem.*, 3: 108–117, 1992) and excess pyridine. The reaction solution was heated at 60° C. for 10 minutes and then evaporated. The residue was purified by preparative HPLC to give [(N-methyl-N-biotinyl)-N-glycyl]-aminobenzyl-DOTA.

1. Preparation of (N-methyl)glycyl biotin. DMF (8.0 ml) and triethylamine (0.61 ml, 4.35 mmol) were added to solids N-methyl glycine (182 mg, 2.05 mmol) and N-hydroxysuccinimidyl biotin (500 mg, 1.46 mmol). The mixture was heated for 1 hour in an oil bath at 85° C. during which time the solids dissolved producing a clear and colorless solution. The solvents were then evaporated. The yellow oil residue

EXAMPLE XVI

Palytoxin-Containing Conjugates

A. Palytoxin-mono-oxyacetyl-LC-biotin.

Trichloroethyl carbamate-NH-palytoxin (troc-NH-palytoxin). Trichloroethyl-chloroformate (available from Aldrich Chemical Co., Milwaukee, Wis.) is added to a solution of palytoxin (available from Hawaii Biotechnology Group, Inc., Aiea, Hi.) in pyridine. The solution is stirred at 23° C. for 6 hours, and the solvents are evaporated under reduced pressure. The residue is dissolved in water and washed with $CH_2Cl_2$. The aqueous fraction is lyophilized, and the product is purified by CM-Sephadex D-25 chromatography.

(Trichloroethyl carbamate (Troc)-NH)-palytoxin-oxyacetyl-LC-biotin. 1.0 equivalent of sodium hydride is added to a solution of troc-NH-palytoxin in DMF followed by 1.0 equivalent of iodoacetyl-LC-biotin. The suspension is stirred at 23° C. for 24 hours, then quenched by the addition of water; acidified to pH 7 by the addition of 0.1M HCl; and troc-deprotected (zinc in aqueous THF in a phosphate buffer, pH 5.5) to afford the final product.

B. Palytoxin-mono-oxo-N-acetamido-ethyldiamine-N'-(N-methyl)-glycyl-biotin.

N-methyl-glycyl-biotin. N-methyl-glycine (trivial name sarcosine, available from Sigma Chemical Co.) was condensed with biotin-NHS ester in DMF and triethylamine to obtain N-methyl glycyl-biotin.

More specifically, DMF (8.0 ml) and triethylamine (0.61 ml, 4.35 mmol) were added to solids N-methyl glycine (182 mg, 2.05 mmol) and N-hydroxy-succinimidyl biotin (500 mg, 1.46 mmol). The mixture was heated for 1 hour in an oil bath at 85° C. during which time the solids dissolved producing a clear and colorless solution. The solvents were then evaporated. The yellow oil residue was acidified with glacial acetic acid, evaporated and chromatographed on a 27 mm column packed with 50 g silica, eluting with 30% MeOH/EtOAc 1% HOAc to give the product as a white solid (383 mg) in 66% yield.

H-NMR (DMSO): 1.18–1.25 (m, 6H, $(CH_2)_3$), 2.15, 2.35 (2 t's, 2H, $CH_2CO$), 2.75 (m, 2H, $SCH_2$), 2.80, 3.00 (2 s's, 3H, $NCH_3$), 3.05–3.15 (m, 1H, SCH), 3.95, 4.05 (2 s's, 2H, $CH_2N$), 4.15, 4.32 (2 m's, 2H, 2CHN's), 6.35 (s, NH), 6.45 (s, NH).

Palytoxin-mono-oxo-N-acetamido-ethyldiamine-N'-(N-methyl)-glycyl-biotin. N-methyl-glycyl-biotin is esterified in refluxing methanol containing gaseous HCl to give the methylester, methyl-(N-methyl)glycyl-biotin. This methyl ester is dissolved in ethylene diamine and stirred at 23° C. for 14 hours to afford biotinyl-N-methyl-glycyl-ethylene diamine monoamide. The solvent (ethylene diamine) is evaporated under vacuum. The amino group of biotinyl-N-methyl-glycyl-ethylene diamine monoamide is acylated with N-hydroxysuccinimidyl iodoacetate (prepared from iodoacetic acid available from Aldrich Chemical Co., N-hydroxysuccinimide and dicyclohexylcarbodiimide (DCC)) in DMF with triethylamine to form an acylated iodinated biotin derivative. Troc-NH-palytoxin prepared as set forth above is deprotonated with 1.0 equivalents of sodium hydride and O-alkylated with the iodo-biotin derivative, N-(iodoacetyl)-ethylene-diamine-N'-(N-methyl) glycylbiotin, to afford the ether, N-(trichloroethoxycarbonyl)-palytoxin-mono-oxo-N-acetamido-ethylenediamine-N'-(N-methyl)glycylbiotin. The trichloro-carbamate group of the ether is cleaved with zinc in aqueous THF, pH 5.5–7.2, to afford the final product.

C. Carboxy-liberated palytoxin-N(Me)-glycyl-biotin.

The two amide bonds of Troc-amine protected palytoxin (troc-NH-palytoxin) are cleaved with peptidase (available from Sigma Chemical Company), a compound that selectively cleaves amide bonds under mild conditions, at pH 7.1 and 37° C. to afford a palytoxin molecule with a free carboxy group. This product is purified by preparative HPLC—reverse phase C-18 chromatography. The free carboxy group is activated with EDCI and coupled to biotinyl-N-methyl-glycyl-ethylene diamine monoamide to give N-(trocNH)-palytoxinamido-ethylenediamine-N'-(N-methyl)-glycyl-biotin. The troc group is cleaved with zinc in aqueous THF to afford the final product.

D. C-55 palytoxin-biotin conjugate.

Trichloroethyl carbamate-NH-palytoxin (troc-NH-palytoxin). Trichloroethyl-chloroformate (available from Aldrich Chemical Co.) is added to a solution of palytoxin in pyridine. The solution is stirred at 23° C. for 6 hours, and the solvents are evaporated under reduced pressure. The residue is dissolved in water and washed with $CH_2Cl_2$. The aqueous fraction is lyophilized, and the product is purified on CM-Sephadex D-25 chromatography.

Troc-NH-palytoxin-$C_{55}$-NH-$(CH_2)_5$-NH-biotin. To a solution containing 1.0 equivalent of troc-NH-palytoxin and 1.0 equivalent of biotinylpentylamine (available from Pierce Chemical Co., Rockford, Ill.) in methanol (adjusted to pH 6 by addition of 5N HCl/methanol) is added 1.0 equivalent of $NaCNBH_3$. This reaction mixture is stirred for 24 hours at 23° C. to afford the biotinylated palytoxin product.

E. Palytoxin-streptavidin conjugation.

The amide bond at carbon 17 of Troc-amine protected palytoxin is cleaved with peptidase (available from Sigma Chemical Company), a compound that selectively cleaves amide bonds under mild conditions, at pH 7.1 and 37° C. to afford a palytoxin molecule with a free carboxy group. This product is purified by preparative HPLC—reverse phase C-18 chromatography. The free carboxy group is activated with EDCI and coupled to streptavidin (available from Sigma Chemical Company) to give N-troc-palytoxinamido-streptavidin. The troc group is cleaved with zinc in aqueous THF (>5:1 $H_2O$:THF) to afford the final product.

EXAMPLE XVII

Polymer-Ligand Conjugation

Polylysine (approximately 10,000 Dal. molecular weight, available from Sigma Chemical Co., St. Louis, Mo.) and dextran (lysine fixable, available from Sigma Chemical Co.) were derivitized with SPDP and purified from unreacted SPDP using size exclusion chromatography (using a PD-10 column available from Pharmacia, Piscataway, N.J.). The resultant SPDP-derivitized adducts were reduced with DTT in pH 4.7 0.2 M NaOAc buffer to generate free reactive thiols. Reduced Tc-99m, generated from stannous gluconate as described, for example, by Carlsson et al., *Biochem. J.,* 173: 723–737, 1978, was added. A 90% incorporation of Tc-99m was obtained for the polylysine adduct within 15 min, as measured by ITLC. 96% of the radioactivity coeluted with the dextran using size exclusion (PD-10) chromatography. These results are indicative of chelation.

EXAMPLE XVIII

Synthesis of Toxin-Polymer-Ligand Conjugates

Trichothecene-Polymer-Ligand Conjugation

Experimentation involving the use of a biotin-dextran-trichothecene conjugate in a pretargeting approach included:

trace labeling using an I-125 PIP NHS ester of an available lysine of a 70,000 dalton dextran molecule that had been biotinylated in accordance with techniques discussed herein in Example XVII, yielding radiotagged dextran biotin (represented as dextran*-biotin);

trichothecene drug conjugation to the remaining lysines using an NHS activated trichothecene;

demonstration of binding of the drug-dextran*-biotin molecule to immobilized avidin; and assessment of serum clearance in mice.

Biotinylated dextran having a molecular weight of 70,000 daltons, with 18 moles of biotin covalently bound thereto and 18 additional lysine epsilon amino groups, was purchased from Sigma Chemical Co. (St. Louis, Mo.). To radiolabel the material, 4 mC of I-125 PIP NHS ester of specific activity of 2200 mCi/mmole (New England Nuclear, Boston, Mass.) in acetonitrile in a 2 ml glass vial was blown down to dryness in a nitrogen stream. 10 mg of biotinylated, lysine-derivatized dextran lyophilizate, reconstituted with 0.650 ml of 1.0M sodium borate, pH 9.0, was added to the iodinating compound and incubated at room temperature for 10 minutes. Following reaction, the radioiodinated dextran moiety was purified by size exclusion chromatography using a PD-10 column (Pharmacia, Uppsala, Sweden) equilibrated in phosphate buffered saline (i.e., 6.2M sodium phosphate, 150 mM NaCl, pH 7.2) containing 1% molecusol (Pharmatec, Alachua, Fl.). The biotin-dextran* eluted from the column in the 2.4–4.8 ml fractions at a specific activity of 0.2 mCi/mg and a concentration of 3.5 mg/ml.

To derivatize the biotin-dextran* with trichothecene, 0.9 ml of biotin-dextran* was diluted with 1.3 ml of sodium borate buffer, 0.3M, Ph 8.5, containing 1% molecusol followed by addition, with stirring of 1.2 ml of DMSO containing 1.2 mg of 2'-Desoxy-2'-alpha-(N-hydroxysuccinimidyl-3-dithiopropanoic acid)-Roridin A (i.e., 2:1 drug to available lysine molar ratio). After incubation for 1.5 hours at room temperature, each 1 ml aliquot of reaction mixture was purified as noted above with a PD-10 column equilibrated in PBS. Yields exceeded 85%.

To establish that the biotin-dextran*-trichothecene molecule was able to bind to avidin or streptavidin, 1 microgram of biotin-dextran* and 1 microgram of biotin-dextran*-trichothecene were incubated for 15 minutes at room temperature with 1 unit of avidin insolubilized on agarose beads (Sigma Chemical Co., St. Louis, Mo.) in 0.2 ml of 0.2 M Pi buffer, pH 6.3 containing 150 mM NaCl. Following this incubation, the percent radioactivity bound to the agarose beads was assessed after dilution with 1.4 ml buffer, centrifugation of the agarose suspension and three washings of the pellets with 1.4 ml buffer. 100% binding was observed for both biotin-dextran* and biotin-dextran*-trichothecene.

Serum clearance studies of biotin-dextran* and biotin-dextran*-trichothecene were also performed in Balb C mice. Serial blood samplings revealed that he two molecules exhibited substantially similar serum clearance upon injection of 2 $\mu$Ci thereof.

EXAMPLE XIX

PEGylation of Streptavidin

The purpose of this experiment was to determine if PEGylation (wherein "PEGylation" refers to the attachment of polyethylene glycol residues to a particular moiety, e.g., protein or polypeptide) of streptavidin at different molar offerings, i.e., mole ratios, results in differential PEG derivatization and streptavidin biotin binding capacity.

In the following example, TresylPEG, molecular weight of 5000 daltons, (Sigma Chemical, St. Louis, Mo.) was the activated form of PEG used for derivitization of streptavidin. The TresylPEG alkylates the amine groups on the SA protein, thereby providing for PEG derivatized SA. This reaction scheme, and the reaction by which Sigma produced TresylPEG, is shown below.

Scheme 1.

$$CH_3(OCH_2CH_2)_nOH + ClSO_2CH_2CF_3 \longrightarrow CH_3(OCH_2CH_2)_nOSO_2CH_2CF_3 + HCl$$

MPEG    tyresyl chloride    tresylated MPEG $F_3CCH_2SO_2OH$ $H_2N$—Protein—$NH_2$, $NH_2$, $NH_2$ PEG—NH
PEG—NH—Protein—$NH(CH_2CH_2O)_nCH_3$
PEG—NH MPEG-modified protein Reactions involved in the activation of MPEG with tresyl chloride and the subsequent coupling of the activated polymer to amino groups in a protein (from Delgado et al., Id.).

Protocol for Attachment of Polyethylene Glycol Moieties to Streptavidin

The experimental protocol was effected as follows:

Two reactions were effected, each using 2.96 mg streptavidin (SA; 49 n mol) in 0.5 mL. 50 $\mu$l of 1 M carbonate at pH 10 was added to each solution followed by tresylPEG at two molar ratios relative to streptavidin: 12 and 40 times (×). In the 12× reaction, 2.95 mg TresylPEG (0.59 $\mu$mol) in dH$_2$O was added to the SA solution. In the 40× reaction 9.8 mg (1.96 $\mu$mol) TresylPEG in dH$_2$O was added. Both reactions were complete in ten minutes after all the components of the reaction were mixed. Residual tresylPEG and its hydrolysis products were subsequently removed using an S-200 (Pharmacia, Uppsala Sweden) size exclusion column equilibrated in PBS. The results were as follows. The 12× reaction recovery after concentration was 0.5 ml at 3.51 mg/ml or 1.76 mg. The 40× reaction recovery after concentration was 0.5 ml at 3.71 mg/ml or 1.85 mg.

After these reactions were completed, the PEGylation ratio was determined by proton Nuclear Magnetic Resonance (NMR). The four repeating ethylene protons/PEG subunit gave a singlet at approximately 3.6 ppm. The signal was integrated and compared to an internal standard of toluene sulfonic acid (TSA). The three methyl protons/TSA molecule gave a singlet at approximately 2.3 ppm. A relative assessment of PEGylation was also done using size exclusion chromatography (SEC) with a GF-250 Zorbax (Du Pont, Wilmington, Del.) column. The results of these experiments are as follows.

NMR 12x:

53 Mg (0.15 ml) conjugate was roto-evaporated to dryness, and then resuspended in 0.5 ml of $D_2O$. The final protein concentration ($A_{280}$) was 1.0 mg/ml, hence, the sample contained 0.5 mg or 8.3 m mol SA. For the internal standard, 8.76 mg (45.6 μmol) TSA was dissolved in $D_2O$ and added to the SA solution. The final sample volume, containing both SA and TSA, was 0.8 mL. The quantity of TSA was calculated to provide a signal whose integral was three times the area that the PEG signal would have been if SA derivatization were 100% efficient.

NMR 40x:

0.52 mg (0.14 ml) of the conjugate was roto-evaporated to dryness and then resuspended in 0.5 ml $D_2O$. The final protein concentration ($A_{280}$) was 1.03 mg/ml, hence, the sample contained 0.51 mg or 8.5 m mol conjugate. For the internal standard 4.92 mg TSA (25.84 μmol) was dissolved in $D_2O$ and added to the conjugate solution. The final volume was 0.8 mL. The quantity of TSA was calculated to provide a signal whose integral was 0.5 times the integral that the PEG signal would have been if SA derivatization were 100% efficient.

Biotin Binding Capacity

Biotin binding capacity of the PEG derivatized streptavidin molecule was then determined using the displacement of 2-(4'-hydroxy-azobenzene)benzoic acid (HABA) from streptavidin by biotin. When HABA is bound to streptavidin there is a spectral shift at 500 nm which is proportional to the amount of bound HABA. HABA is quantitatively displaced from streptavidin by biotin. This enables the titration of the HABA-SA complex with biotin to be monitored directly by 500 nm absorbance, thereby providing a molar concentration of biotin binding sites. The ratio of binding site concentration to modified streptavidin concentration provides an indication of how the modification has disturbed biotin binding ability. (Unmodified streptavidin binds four biotin molecules.) The experimental protocol is as follows:

HABA assay on PEG modified and unmodified SA:

The protein of interest was diluted to 0.25 mg/ml in PBS, then used to blank the spectrophotometer at 500 nm. 25 μl of a 10 mM solution of HABA in 10 mN NaOH was added to the solution and the $A_{500}$ was measured. Successive 5 μl aliquots of a 500 μM biotin solution were added and the $A_{500}$ measured after each addition. Biotin additions were continued until there was no further change in $A_{500}$. The inflection point is equal to the concentration of biotin binding sites present in the sample solution. The concentration of biotin binding sites divided by the concentration of conjugate is equal to the binding site/SA ratio.

Results

NMR and SEC Results

The proton NMR plots from the 12x and 40x PEG derivatized SA samples, respectively, were then analyzed. The results show that the streptavidin derivatized at the 12x offering ratio actually derivatized at an average of 7.4 PEG's/SA molecule. The SA derivatized at the 40x offering ratio actually derivatized at an average of 18.8 PEG's/SA molecule. The difference in derivatization level was also reflected by the GF-250 chromatographic traces, the results of which are summarized in the table below.

TABLE 5

| SAMPLE | RETENTION TIME |
|---|---|
| SA Control | 9.68 |
| 12X Offering | 7.57 |
| 40X offering | 7.22 |

Retention time in minutes

The results of these experiments indicate that PEG derivatized samples elute relative to their PEG loading levels with the higher derivatized streptavidin (40x) eluting earlier than the non- or lower-derivatized streptavidin sample (12x). The peak width for each derivatized streptavidin sample is also broader than the streptavidin control. This was most obvious in the 12x offering sample. This broadening is believed to be due to a combination of chromatographic behavior and heterogeneity and serves as a reminder that the quantitative tests represent average values for the molecular population.

Biotin Binding Assay Results

The HABA assay was used to determine the biotin binding capacity of the SA control and PEG:SA conjugates. The table below summarizes these assay results:

TABLE 6

| Cumulative μl 500 μM biotin soln | 0.32 mg SA Control, $A_{500}$ | 0.25 mg SA + 7.4 PEG's $A_{500}$ | 0.25 mg SA + 18.8 PEG's, $A_{500}$ |
|---|---|---|---|
| 0 | 0.718 | 0.234 | 0.186 |
| 5 | 0.660 | 0.198 | 0.158 |
| 10 | 0.602 | 0.166 | 0.152 |
| 15 | 0.546 | 0.158 | 0.151 |
| 20 | 0.490 | 0.158 | |
| 25 | 0.442 | | |
| 30 | 0.382 | | |
| 35 | 0.325 | | |
| 40 | 0.269 | | |
| 45 | 0.217 | | |
| 50 | 0.161 | | |
| 55 | 0.157 | | |
| 60 | 0.164 | | |

SA Control (0.32 mg SA/60K g/mol)×1000=5.3 nmol of streptavidin

50 μl of 500 μM solution of biotin=25 nmol biotin

Biotin/SA: 25 nmol biotin/5.3 nmol SA=4.7 biotin bound/streptavidin

Theoretical is 4.0 biotin/streptavidin so this is about 15% higher than theoretical.

12x Offering (0.25 mg (PEG)$_{7.4}$SA/60K g/mol)×1000=4.2 nmol PEG::streptavidin. Although the addition of PEG on the streptavidin increases its mass, it was confirmed by BCA and A-280 protein assays that PEG does not interfere with protein mass measurement. Therefore, 60 Kd used in the above calculations was found to be acceptable in these PEG derivatization experiments.

15 μl of 500 μM biotin solution=7.5 nmol biotin

Biotin/PEG:SA=7.5 nmol biotin/4.2 nmol PEG:SA=1.79 biotin bound/PEG:SA

40x Offering (0.25 mg (PEG)$_{18.8}$:SA/60K g/mol)×1000=4.2 nmol PEG:SA

10 μl of 500 μM biotin solution - 5.0 nmol biotin

Biotin/PEG:SA=5.0 nmol biotin/5.0 nmol PEG:SA—1.19 biotin bound/PEG:SA

The biotin binding data is summarized in Table 7 shown below:

TABLE 7

| Sample | Biotin/SA |
|---|---|
| SA Control | 4.70 |
| (PEG)$_{7.4}$:SA | 1.79 |
| (PEG)$_{18.8}$:SA | 1.19 |

These results indicate that there is loss of biotin binding capacity with increasing PEG derivatization. To overcome this problem, it was hypothesized by the present inventors that the biotin binding sites should be protected during the PEGylation process. However, it first needed to be determined if PEGylation resulted in a conformational change in the protein's structure which caused the loss of biotin binding capability. To determine whether this was occurring, the following experiment was done.

Evaluation of Conformational Effects of PEG Derivitization on Streptavidin

Procedure

SA was mixed with $^{125}$I (14 µCi) labeled N-(p-iodobenzoyl)biocytin (PIB-biocytin) and allowed to incubate for about 15 minutes. A 5 molar excess of biotin over the biotin binding sites was then added to the streptavidin-PIB-biocytin complex. If PIP-biocytin was displaced by PEGylation and the binding site on streptavidin was still reactive, then a biotin molecule would occupy the binding site, leaving the PIB-biocytin free in solution.

Streptavidin was then reacted with a 40× Molar excess of tresylPEG at pH 10.0 using the same methods described in the previous experiments.

There were 2 control reactions also prepared at the same time. These include a non-PEGylated streptavidin sample and a $^{125}$PIB-Biocytin sample.

Following confirmation of the completion of the PEGylation reaction by GF-250 SEC, all three samples were exhaustively centrifuged in ultrafiltration devices with a 30 Kd cut-off (Amicon Inc., Beverly, Mass.) and the total, filtrate, and retentate radioactivity measured by a Squibb CRC-6A Radioisotope Calibrator (Squibb, Princeton, N.J.). The following table summarizes the centricon results:

TABLE 8

| Measured | Microcuries of $^{125}$I | | |
|---|---|---|---|
| Sample | Total | Filtrate | Retentate |
| $^{125}$PIB-Biocytin | 15.9 | 14.4 (91%) | 1.4 (9%) |
| SA + $^{125}$PIB-Biocytin | 13.4 | 1.8 (14%) | 11.2 (86%) |
| PEG:SA + $^{125}$PIB-Biocytin | 13.1 | 1.4 (11%) | 11.4 (89%) |

The SEC trace of the PEGylated SA:$^{125}$PIB-biocytin complex showed a retention time of 7.32 minutes, which is similar to what was observed in earlier PEGylation experiments (see Table 1).

The $^{125}$PIB-Biocytin Control indicate that greater than 90% of the activity flowed through the centricon membrane, which is consistent with a small molecule (<1000 daltons MW) not interacting with the larger macromolecular SA molecule. 86% of the SA+$^{125}$PIB-Biocytin remained in the retentate following ultrafiltration. This is the expected result if the $^{125}$PIB-Biocytin is bound to the 60 MW protein. The PEG:SA+$^{125}$PIB-Biocytin sample also showed stable biotin binding characteristics where 89% of the activity remained in the retentate similar to the SA+$^{125}$PIB-Biocytin control.

Thus, these results provide evidence that polyethylene glycol derivatized streptavidin may be obtained which retains good biotin binding capacity based on the fact that there is apparently no substantial conformational change to the protein structure attributable to PEGylation. More particularly, the results further indicate that there is no significant conformational change in the streptavidin molecule that results in reduced biotin binding capacity of streptavidin. It is hypothesized that the PEG derivatized streptavidins which bound biotin poorly probably do so because of steric hinderance problems. Therefore, protection of the biotin binding sites of streptavidin prior to PEGylation should obviate such steric constraints. Such protection may be effected by the attachment of moieties which reversibly bind to biotin binding sites. Therefore, an experiment was next effected which exploited the reversible streptavidin binding characteristics of iminobiotin as a blocking agent during the PEGylation procedure. This experiment was effected to demonstrate that occupation of biotin binding sites prior to PEGylation by iminobiotin followed by release of iminobiotin after PEGylation preserves the biotin binding capacity of the streptavidin.

Iminobiotin Protection of Streptavidin Prior to PEGylation

Iminobiotin (IB) was chosen as a biotin binding site blocking agent because of the avid, reversible binding of this molecule to streptavidin. At pH's approaching the pKa of 11–12, the guanidino group of IB becomes partially to totally deprotonated resulting in increased binding affinity for SA. Moreover, following PEGylation, the bound and unbound IB can be removed from the reaction mixture by gel filtration at low pH (4.0). However, other low affinity biotin analogs may be substituted for iminobiotin. These observations form the basis for the following experiment.

Experimental Protocol

To 2.0 mg SA (=48 nmol) in 0.5 ml buffer was added 50 µl 1.0 M carbonate, pH 10.0

48 nmol SA×4 binding sites/SA×5 (excess)=0.96 µmol of iminobiotin (IB) (243.3 MW) to add to reaction mixture.

0.96 µmol×0.2433=0.23 mg IB (1000 µl/ml×0.23 mg)/1.4 mg/ml IB soln=164 µl IB solution in dH$_2$O.

Reaction proceeded 15 minutes TresylPEG: 48 nmol SA×40 (excess) TresylPEG=1.93 µmol TresylPEG 1.93 µmol TresylPEG×5K g/mol=9.7 mg TresylPEG The reaction was monitored by Zorbax SEC and was complete in 10 minutes.

The pH was lowered to pH 3.0 with 1 M acetic acid following completion of reaction and purified over a S-200 SEC (Pharmacia, Uppsala, Sweden) column equilibrated in 0.1% acetic acid to remove both PEG byproducts and displaced IB.

Ultrafiltration and buffer exchange into PBS was then done on the final PEG:SA conjugate for further characterization.

SEC, HABA and NMR assays were done as previously described. The results of these experiments are presented below.

The Zorbax SEC traces of SA control and the SA:PEG conjugate prepared as described above were overlaid. The retention time was 7.37 minutes for the PEGylated SA which is between the 12× and 40× offering retention times observed previously (see Table 1). The proton NMR spectra indicated there to be 10.92 PEG/SA molecule which is lower than the derivatization level observed with the 40× loading in the previous experiments, but significantly higher than what was observed in the 12× offering. This is consistent with the SEC data. The following table summarizes the HABA assay results for the preparation of PEG:SA conjugate.

TABLE 9

| Cumulative μl 500 μM Biotin | $A_{500}$ |
|---|---|
| 0 | 0.394 |
| 5 | 0.355 |
| 10 | 0.317 |
| 15 | 0.279 |
| 20 | 0.241 |
| 25 | 0.203 |
| 30 | 0.168 |
| 35 | 0.163 |

The 0.25 mg SA:PEG in the HABA assay corresponds to 4.2 nmol. Thirty μl of 500 μM solution (15 nmol) were required to displace the bound HABA. Therefore, the Biotin/SA Ratio was 15/4.2 or 3.6 biotin bound per SA:PEG conjugate molecule. These results are a significant improvement over what was observed in the non-blocked SA:PEG conjugates. Thus, these results demonstrate that blocking of biotin binding sites prior to PEGylation substantially alleviates the loss of biotin binding capability. It is expected that similar results can be obtained using other biotin binding site protecting groups, e.g., low affinity biotin analogs, peptide mimetics which bind to biotin binding sites, antibodies to biotin binding sites and fragments and recombinant forms thereof. Many low affinity biotin analogs are known and available and are identified elsewhere in this application. These results are summarized as follows.

The inventors initially hypothesized that, because tresylPEG derivatization of proteins yields a modification in which the charge of the modified amino group is retained, this form of PEGylation of streptavidin would cause minimal disturbance of the biotin binding capacity. Unexpectedly, it was found that direct conjugation of streptavidin with TresylPEG derivatives using procedures reported in the literature resulted in a substantial loss in its ability to bind the small molecule biotin. Also, it was demonstrated that when streptavidin to which labeled biotin had been previously complexed was derivatized with TresylPEG, no biotin was released. This provided strong evidence that PEGylation does not destroy the integrity of the protein and that pre-blocking the biotin binding sites on streptavidin with a displaceable biotin analog effectively protects the biotin binding capacity of the streptavidin after modification (PEGylation).

Iminobiotin is an analog of biotin that has a graduated affinity for streptavidin depending on the pH of the solution. At high pH's iminobiotin is strongly bound to the streptavidin molecule and therefore provides good blocking characteristics. PEGylation of this streptavidin-iminobiotin complex followed by subsequent removal of iminobiotin by lowering the pH of the reaction mixture and running the sample over a gel filtration column, equilibrated at low pH results in a SA:PEG conjugate that retains its biotin binding ability.

Subsequent experiments validated the utility of this method and the inventors' initial hypotheses. In vivo and in vitro experiments showed that streptavidin modified with PEG in the manner described herein reduced its immunogenicity to background levels. Also, the streptavidin derivatized with PEG in this manner was readily conjugated to antibody for antigen mediated targeting. Thus, these results demonstrate that polyethylene glycol derivatized ligands and anti-ligands, e.g., streptavidin and avidin, are useful in the preparation of conjugates for use in pretargeting methods. Such PEG derivatized ligands and anti-ligands are especially suitable for therapeutic pretargeting methods where immunogenicity may be a potential concern.

It is further expected that the administration of a clearing agent should further alleviate a potential antigenic reaction to the administered therapeutic agent conjugate as described supra, since it will further reduce the time the therapeutic agent is in contact with the immune system. Also, it is expected that these results can be extrapolated to other ligands or anti-ligands, as well as targeting moieties or active agents used in pretargeting protocols.

EXAMPLE XX

Superantigen Pretargeting

A patient presents with colon cancer. A monoclonal antibody (MAb) directed to a colon cancer cell antigen, e.g., NR-LU-10, is conjugated to streptavidin to form a MAb-streptavidin conjugate. The MAb-streptavidin conjugate is administered to the patient in an amount sufficient to substantially saturate the available antigenic sites at the target (which amount is at least sufficient to allow the capture of a therapeutically effective active agent dose at the target and which amount may be in excess of the maximum tolerated dose of conjugate administrable in a conventional targeted, chelate-labeled molecule protocol, such as administration of monoclonal antibody-chelate-radionuclide conjugate). The MAb-streptavidin so administered is permitted to localize to target cancer cells for 24 to 44 hours, preferably 48–72 hours.

A biotin-active agent, e.g., toxin or cytokine or radionuclide, conjugate prepared as described above is dispersed in a pharmaceutically acceptable diluent and administered to the patient in a therapeutically effective dose (e.g., a dose sufficient to induce a cytotoxic effect at the target cell site). The biotinylated superantigen localizes to the targeted MAb-streptavidin at the tumor or is metabolized or excreted from the patient via the renal pathway.

EXAMPLE XXI

Proposed Synthesis of Biotinamido-N methylglycyl-seryl-O-succinamido-benzyl-DOTA The synthesis of biotinamido-N-methylglycyl-seryl-O-succinamido-benzyl-DOTA is effected by the following synthesis scheme:

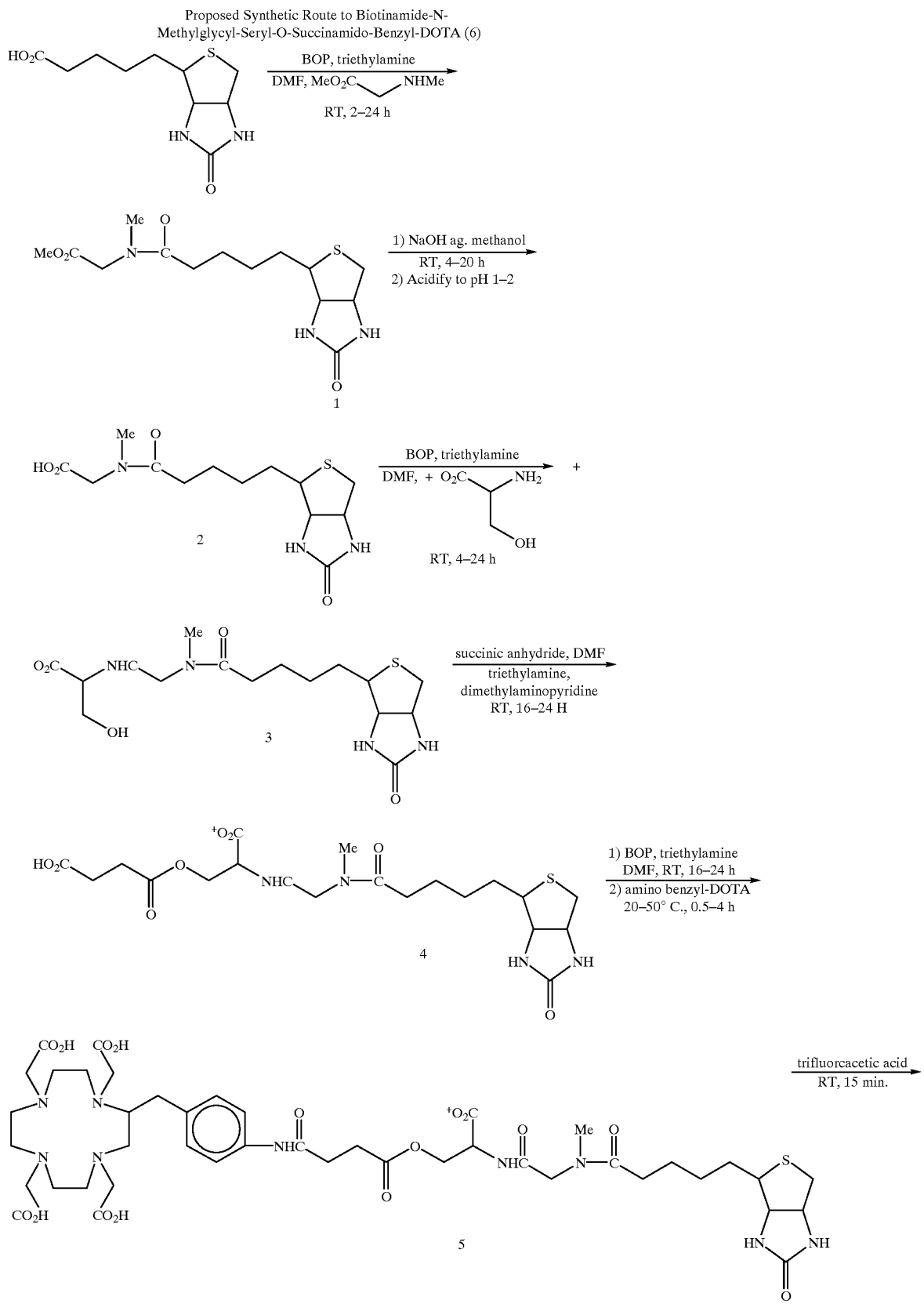

-continued

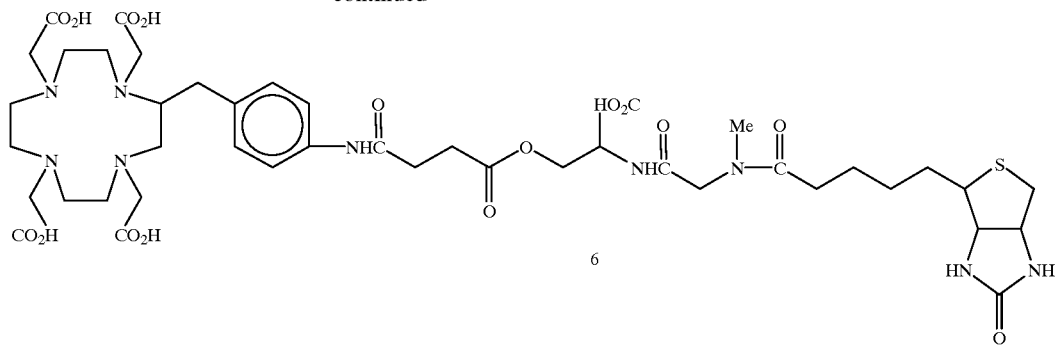

Synthesis of Biotinamido-N-methylglycine Methyl Ester (4)

To a solution of biotin in anhydrous dimethylformamide is added 1.1 equivalents of N-methylglycine methyl ester and 3 equivalents of triethylamine followed by the addition of 1.05 equivalents of BOP (benzotriazol-1-yloxy-tris (dimethylamine)phosphonium hexafluorophosphate). The mixture is stirred at 0–25° C. for 2–24 h and then concentrated. The residue is diluted with ethyl acetate and the resulting solution is washed with 1 N aqueous hydrochloric acid and then with saturated aqueous sodium bicarbonate. The organic phase is dried over magnesium sulfate, filtered and then concentrated via reduced pressure rotary evaporation. The residue is chromatographed on silica gel, eluting with 5–15% methanol/ethyl acetate. Chromatographic fractions containing product are combined and concentrated to afford the final product (4).

Synthesis of Biotinamido-N-methylalvcine (5)

To a solution of biotinamido-N-methyl-glycine methyl ester in methanol is added 1.5–2.0 equivalents of 1 N aqueous sodium hydroxide. The mixture is stirred at 15–45° C. for 4–24 h and then concentrated via reduced pressure rotary evaporation. The residue is diluted with deionized water and the pH of the solution is adjusted to 1–2 by addition of 6 N aqueous hydrochloric acid. The mixture is again concentrated via reduced pressure rotary evaporation. The residue is chromatographed on reverse phase C-18 silica gel, and eluted with methanol/water. The fractions containing the product are combined and concentrated to afford the final product (5).

Synthesis of Biotinamido-N-methylalycvl-Serine t-Butyl Ester (6)

To a solution of biotinamido-N-methylglycine (5) in anhydrous dimethylformamide is added 1.1 equivalents of serine t-butyl ester and 3 equivalents of triethylamine followed by 1.05 equivalents of BOP. The mixture is stirred at 0–25° C. for 2–24 h and then concentrated via reduced pressure rotary evaporation. The residue is diluted with ethyl acetate and the resulting solution is washed with 1 N aqueous hydrochloric acid followed by saturated aqueous sodium bicarbonate. The organic phase is dried over magnesium sulfate, filtered and concentrated. The residue is chromatographed on silica gel, and eluted with methanol/ ethyl acetate. The fractions containing product are combined and concentrated to afford the final product (5).

Synthesis of Biotinamido-N-methylglycyl-Seryl-t-butyl Ester-O-Succinate (7)

To a solution of biotinamido-N-methylglycyl-serine t-butyl ester (6) in anhydrous dimethylformamide is added 3 equivalents of triethylamine, 0.01–0.1 equivalents of 4-dimethylaminopyridine and 1.1 equivalents of succinic anhydride. The mixture is stirred at 0–25° C. for 20–24 h and then concentrated via reduced pressure rotary evaporation. The residue is diluted with ethyl acetate and 1 N aqueous hydrochloric acid. The organic phase is then dried over magnesium sulfate, filtered and concentrated. The residue is chromatographed on reverse phase C-18 silica gel, eluting with methanol/water. The fractions containing the product are combined and concentrated to give the final product (4).

Synthesis of Biotinamido-N-methylglycyl-Seryl t-Butyl Ester-O-Succinamido-benzyl-DOTA (8)

To a solution at biotinamido-N-methylglycyl-seryl t-butyl ester-O-succinate (7) in anhydrous dimethylformamide is added 10 equivalents of triethylamine and 0.9–1.0 equivalents of BOP. The mixture is stirred at 15–25° C. for 16–24 h and then aminobenzyl-DOTA in anhydrous dimethylformamide is added. The mixture is stirred at 20–50° C. for 0.5–4 h and then concentrated. The residue is purified by chromatography to afford the final product (8).

Synthesis of Biotinamido-N-methylglycyl-Seryl-O-Succinamide-Benzyl-DOTA (6)

To trifluoroacetic acid is added biotinamido-N-methylglycyl-seryl t-butyl ester-O-succinamido-benzyl-DOTA(8). The mixture is stirred at 15–25° C. for 15 minutes and then concentrated via reduced pressure rotary evaporation. The residue is purified by ion exchange chromatography to afford the final product (9).

This reaction scheme is shown schematically supra.

Kits containing one or more of the components described above are also contemplated. For instance, radiohalogenated biotin may be provided in a sterile container for use in pretargeting procedures. A chelate-biotin conjugate provided in a sterile container is suitable for radiometallation by the consumer; such kits would be particularly amenable for use in pretargeting protocols. Alternatively, radiohalogenated biotin and a chelate-biotin conjugate may be vialed in a non-sterile condition for use as a research reagent.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. Biotinamido-N-methylglycyl-seryl-O-succinamido-benzyl DOTA.

* * * * *